(12) United States Patent
Cole et al.

(10) Patent No.: US 10,737,038 B2
(45) Date of Patent: Aug. 11, 2020

(54) CATHETER INSERTION DEVICE AND METHOD OF INSERTING A CATHETER

(71) Applicant: Becton, Dickinson and Company, Franklin Lakes, NJ (US)

(72) Inventors: Russell Cole, River Vale, NJ (US); John Prudden, Manchester, MA (US); J. Richard Gyory, Sudbury, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 742 days.

(21) Appl. No.: 15/306,365

(22) PCT Filed: Apr. 23, 2015

(86) PCT No.: PCT/US2015/027367
§ 371 (c)(1),
(2) Date: Oct. 24, 2016

(87) PCT Pub. No.: WO2015/164653
PCT Pub. Date: Oct. 29, 2015

(65) Prior Publication Data
US 2017/0043101 A1 Feb. 16, 2017

Related U.S. Application Data

(60) Provisional application No. 61/983,976, filed on Apr. 24, 2014.

(51) Int. Cl.
| | |
|---|---|
| *A61M 5/32* | (2006.01) |
| *A61M 25/06* | (2006.01) |
| *A61M 5/142* | (2006.01) |
| *A61M 5/172* | (2006.01) |
| *A61M 5/168* | (2006.01) |

(52) U.S. Cl.
CPC ...... *A61M 5/3287* (2013.01); *A61M 5/14248* (2013.01); *A61M 5/1723* (2013.01);
(Continued)

(58) Field of Classification Search
CPC ............ A61M 5/3287; A61M 25/0606; A61M 5/14244; A61M 5/14248; A61M 5/158;
(Continued)

(56) References Cited

U.S. PATENT DOCUMENTS

| | | | |
|---|---|---|---|
| 4,755,173 A | 7/1988 | Konopka et al. | |
| 6,572,586 B1 * | 6/2003 | Wojcik .................. | A61M 5/158 128/DIG. 6 |

(Continued)

FOREIGN PATENT DOCUMENTS

| | | |
|---|---|---|
| CA | 2826096 A1 | 8/2012 |
| JP | 2009-516572 A | 4/2009 |

(Continued)

*Primary Examiner* — Kevin C Sirmons
*Assistant Examiner* — Leah J Swanson
(74) *Attorney, Agent, or Firm* — Dickinson Wright, PLLC

(57) ABSTRACT

An insulin infusion system is provided with a manual insertion device having a dual retraction spring (230) configuration for automatic introducer needle (222) retraction. A button (200) of the insertion device is used to insert the introducer needle (222) and catheter (202), and once the introducer needle (222) and catheter (202) have been fully inserted, a rotating engagement releases the dual retraction springs (230) such that the introducer needle (222) automatically retracts, leaving the catheter (202) in the body of the user. An end of the introducer needle (222) remains in the inserted catheter (202) and/or in the septum (206) of the inserted catheter (202) to provide an uninterrupted fluid path.

30 Claims, 66 Drawing Sheets

(52) U.S. Cl.
CPC .... *A61M 25/0606* (2013.01); *A61M 25/0631* (2013.01); *A61M 2005/14252* (2013.01); *A61M 2005/16863* (2013.01); *A61M 2205/50* (2013.01); *A61M 2205/8206* (2013.01)

(58) Field of Classification Search
CPC ............... A61M 5/162; A61M 5/32; A61M 2005/14252; A61M 2005/14256; A61M 2005/1426; A61M 2005/1581; A61M 2005/1583; A61M 2005/1585; A61M 2005/206; A61M 2005/3201; A61M 2005/3289

See application file for complete search history.

(56) References Cited

U.S. PATENT DOCUMENTS

| | | |
|---|---|---|
| 2004/0087912 A1 | 5/2004 | Swenson |
| 2007/0005017 A1* | 1/2007 | Alchas .............. A61M 5/14244 604/117 |
| 2007/0078432 A1 | 4/2007 | Halseth et al. |
| 2007/0185516 A1* | 8/2007 | Schosnig .......... A61B 5/150022 606/181 |
| 2007/0191772 A1 | 10/2007 | Wojcik |
| 2007/0233001 A1 | 10/2007 | Burroughs et al. |
| 2012/0108955 A1 | 5/2012 | Razzaque et al. |
| 2013/0150680 A1 | 6/2013 | Larson et al. |
| 2013/0237918 A1 | 9/2013 | Gyrn |
| 2014/0058353 A1 | 2/2014 | Politis et al. |
| 2014/0088509 A1 | 3/2014 | Sonderegger et al. |

FOREIGN PATENT DOCUMENTS

| | | | |
|---|---|---|---|
| JP | 2010-533525 A | 10/2010 | |
| JP | 2011-115345 A | 6/2011 | |
| WO | WO-2012108955 A2 * | 8/2012 | ........ A61M 5/14248 |
| WO | WO-2012134588 A1 * | 10/2012 | ............ A61M 25/02 |
| WO | WO-2013016376 A2 | 1/2013 | |

* cited by examiner

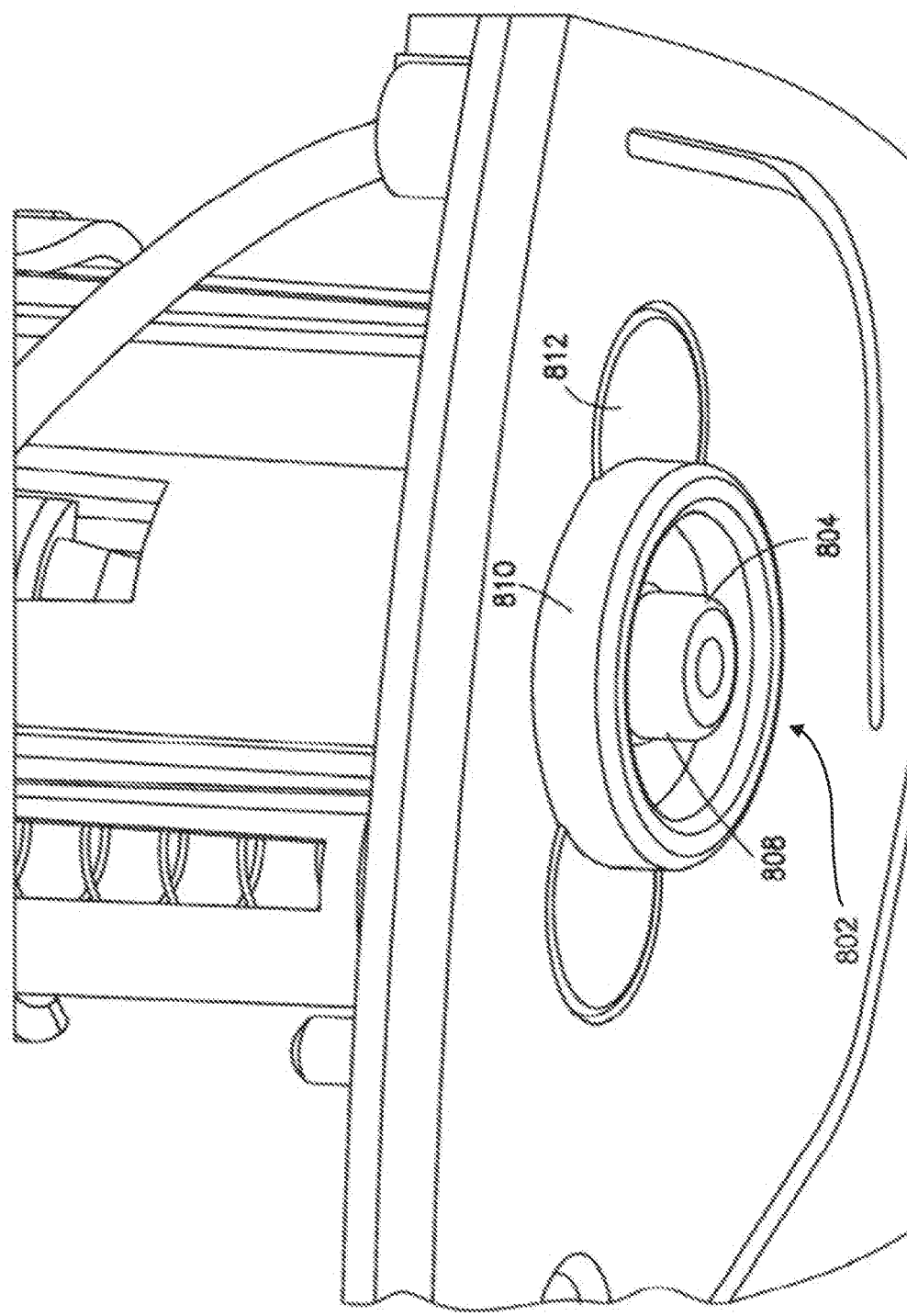

CATHETER INSERTION DEVICE AND METHOD OF INSERTING A CATHETER

CROSS-REFERENCE TO RELATED APPLICATION

This application claims priority under 35 USC § 119(e) from U.S. Provisional Patent Application Ser. No. 61/983,976 filed on Apr. 24, 2014, the entire contents of which is incorporated herein by reference in its entirety.

FIELD OF THE INVENTION

The present invention relates generally to medical infusion systems, such as an insulin infusion device or insertion device, where simple, low-profile and low-part count manual insertion device is provided with a dual retraction spring configuration for automatic introducer needle retraction. The dual retraction spring configuration is implemented using multiple barrel-shaped guides and bosses in the insertion device housing which allows for much smaller retraction springs to be used than in a single-barrel configuration.

BACKGROUND OF THE INVENTION

Diabetes is a group of diseases characterized by high levels of blood glucose resulting from the inability of diabetic patients to maintain proper levels of insulin production when required. Persons with diabetes will require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

For the treatment of type 1 diabetes, there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs.

Infusion pump therapy requires an infusion cannula, typically in the form of an infusion needle or a flexible catheter, that pierces the diabetic patient's skin and through which, infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter extends. The base typically has an adhesive that retains the base on the skin surface during use. The cannula can be inserted onto the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained.

Such devices are replaced on a frequent basis, such as every three days, when the insulin reservoir is exhausted or complications may otherwise occur, such as restriction in the cannula or the infusion site.

As patch pumps are designed to be a self-contained unit that is worn by the diabetic patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced as much as possible. One such part is the insertion mechanism for automatically inserting the cannula into the user's skin.

In order to minimize the height of the insertion mechanism, some conventional insertion mechanisms are configured to insert the cannula at an acute angle from the surface of the skin, e.g. 30-45 degrees. However, it may be preferable to insert the cannula perpendicular or close to the perpendicular from the surface of the skin, since this would require the minimum length of cannula insertion. In other words, with the minimum length of cannula being inserted into the user's skin, the user can experience greater comfort and fewer complications, such as premature kinking of the cannula. But one problem with configuring the insertion mechanism to insert the cannula perpendicular to the surface of the skin is that this may increase the overall height of the insertion mechanism, and therefore of the patch pump itself.

Accordingly, a need exists for an improved insertion mechanism for use in a limited space environment, such as in the patch pump, that can cost-effectively insert a cannula vertically or close to perpendicularly into the surface of a user's skin, while minimizing or reducing its height, in order to reduce the overall height of the device the insertion mechanism is incorporated into, such as a patch pump.

SUMMARY OF THE INVENTION

An object of the present invention is to substantially address the above and other concerns, and provide advanced, improved, and novel components and elements of an insertion device that facilitates insertion of the in-dwelling or soft catheter and retract the introducer needle, while reducing the number of components required for the construction and use of the insertion device.

Another object of the present invention is to provide a manual insertion device with at least automatic introducer needle retraction, such that the part count of the exemplary embodiments is lowered and which serves to keep part production costs low and simplify device assembly. Automatic retraction also simplifies the user interface by minimizing the number of user steps for activation. There is only one step for the user which is pushing the button.

Another object of the present invention is to provide a manual insertion device with at least automatic introducer needle retraction using a dual retraction spring configuration that is implemented using multiple barrel-shaped guides and bosses in the insertion device housing which allows for much smaller retraction springs to be used, such that the device is smaller and more compact.

Another object of the present invention is to provide a manual insertion device with at least automatic introducer needle retraction and activation button locking to provide needle shielding and maintain insertion of the catheter.

These and other objects are substantially achieved by providing an insertion device with a dual retraction spring configuration for automatic introducer needle retraction. The dual retraction spring configuration is implemented using multiple barrel-shaped guides and bosses in the insertion device housing which allows for much smaller retraction springs to be used than in a single-barrel configuration. A button of the insertion device is used to insert the introducer needle and catheter, and once the introducer needle and catheter have been fully inserted, a rotating engagement releases the dual retraction springs such that the introducer needle automatically retracts, leaving the catheter in the body of the user. An end of the introducer needle remains in the inserted catheter or wedge that holds the catheter and/or in the septum of the inserted catheter to provide an uninterrupted fluid path.

Additional and/or other aspects and advantages of the present invention will be set for in the description that follows, or will be apparent from the description, or may be learned by the practice of the invention. The present invention may comprise a method or apparatus or system having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The various objects, advantages and novel features of the exemplary embodiments of the present invention will be more readily appreciated from the following detailed description when read in conjunction with the appended drawings, in which:

FIG. 60 is a view of the insertion device of FIG. 51 showing a skin-contacting surface in accordance with an embodiment of the present invention;

Throughout the drawings, like reference numerals will be understood to refer to like parts, components and structures.

DETAILED DESCRIPTION OF THE EXEMPLARY EMBODIMENTS

The exemplary embodiments of the present invention described below provide novel means of providing one or more infusion device elements that are configured to insert catheter up to 8 mm into a skin surface, but embodiments are not limited thereto. The insertion device is configured to perform a manual insertion of the catheter which allows the insertion device to be smaller, simpler and cheaper than automatic or spring-assisted insertion devices.

Exemplary embodiments of the present invention described below, utilize a manual insertion device and include a dual retraction spring configuration for automatic introducer needle retraction that also allows for a very small device size. The dual retraction spring configuration is implemented using a plurality of cylindrical or barrel-shaped guides. In an exemplary embodiment, one barrel guides a button and catheter, and adjacent barrels house retraction springs, one on each side of the button and catheter. Having the springs in separate barrels allows for much smaller springs than a single-barrel configuration in which the spring is coaxial with the catheter. A single coaxial spring creates access to the button assembly since spring design limitations require the spring to extend nearly from the bottom of the housing to the top. Access is required for features like the locking arm and if the features are implemented inside the spring, the entire mechanism must grow to accommodate them increasing the mechanism foot print.

Figure 1:
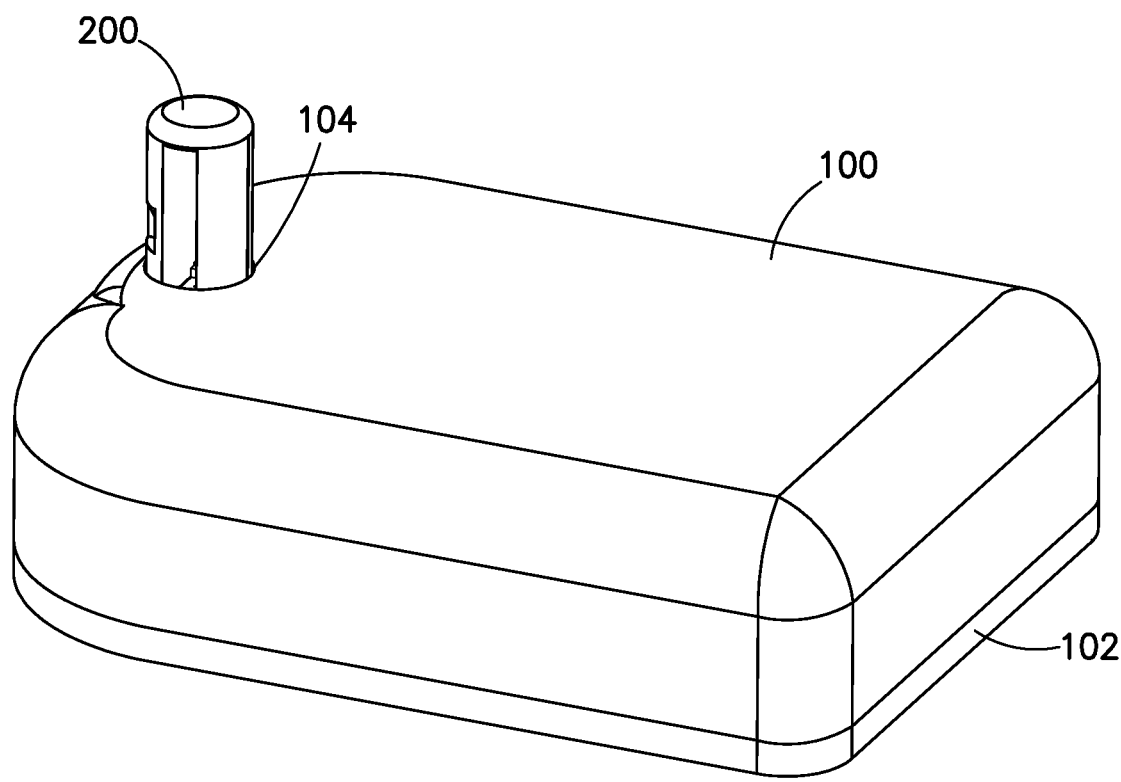
FIG. 1 is an isometric view of an exemplary insertion device in a pre-activation state in accordance with an embodiment of the present invention.
Figure 2:
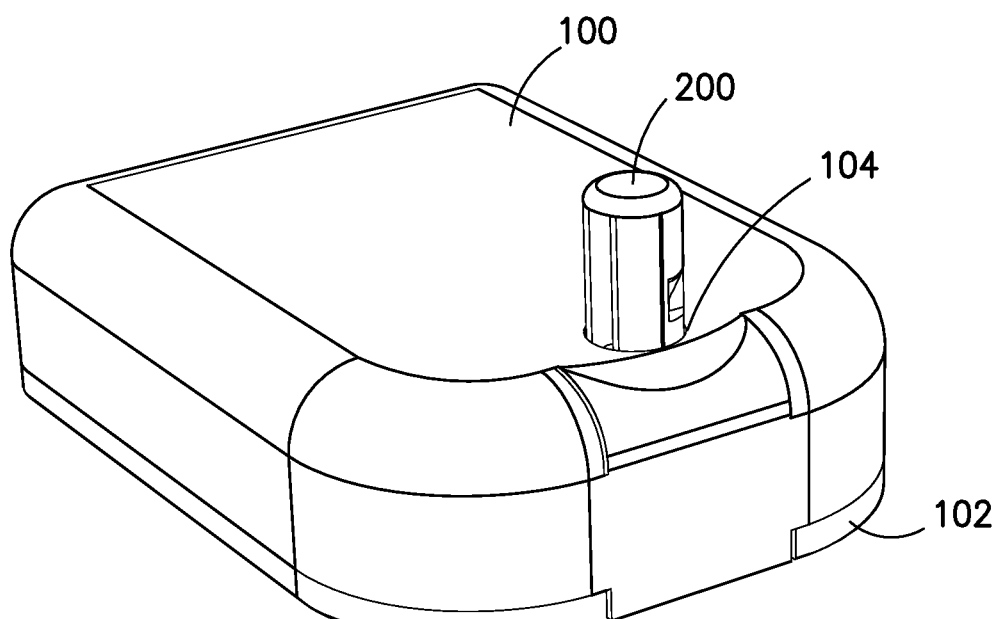
FIG. 2 is another isometric view of the insertion device of FIG. 1 in a pre-activation state in accordance with an embodiment of the present invention.
Figure 3:
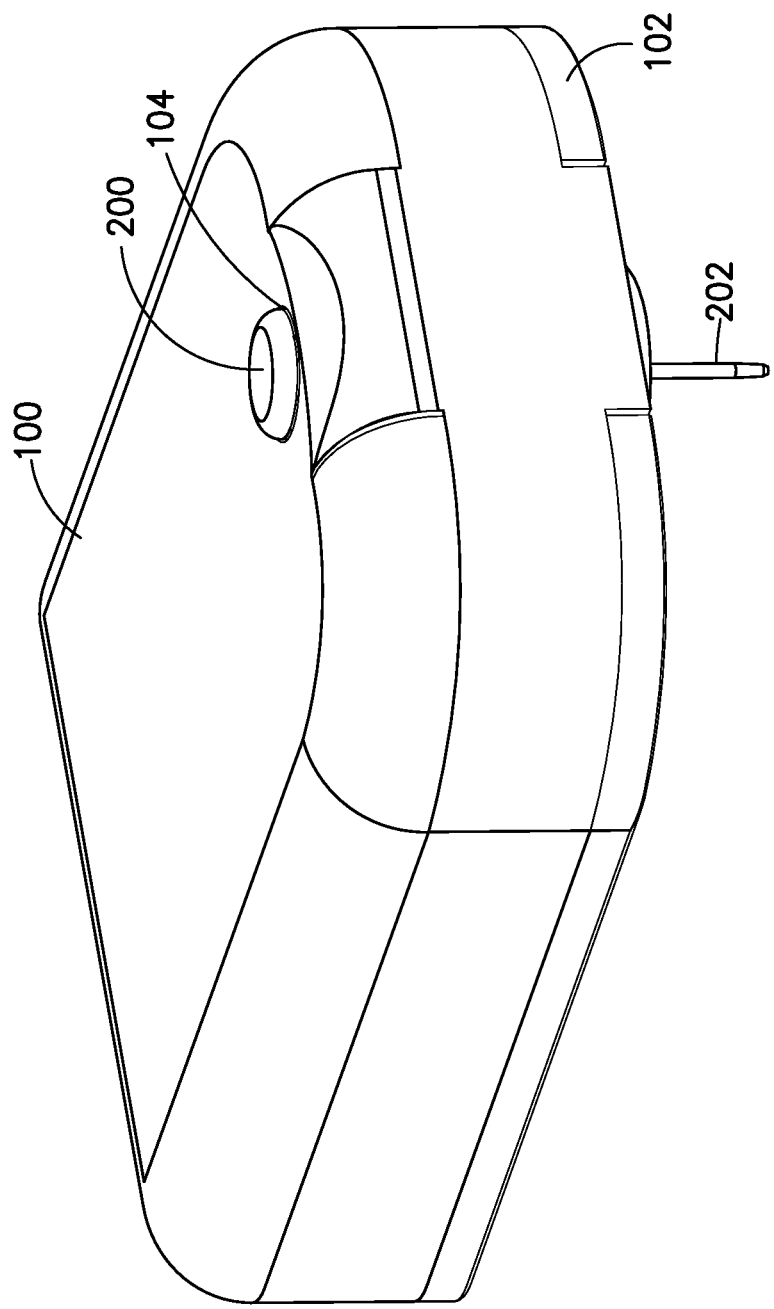
FIG. 3 is a view of the insertion device of FIG. 1 in a post-activation state in accordance with an embodiment of the present invention.

FIGS. 1 and 2 show the insertion device before use and FIG. 3 shows the device after deployment of the cannula. As shown in FIGS. 1-3, the insertion device includes a top housing 100 and a base 102. The top housing 100 is shown having an opening 104 through a top surface from which a user-accessible, and user-acutatable button 200 slidably extends. The content of the insertion device, including the mechanism housing 300, is shown in greater detail in FIG. 4. The top housing 100, button 200, and mechanism housing 300 can be manufactured from ABS, and the base 102 can be manufactured from PETG, but embodiments are not limited thereto.

Figure 4:
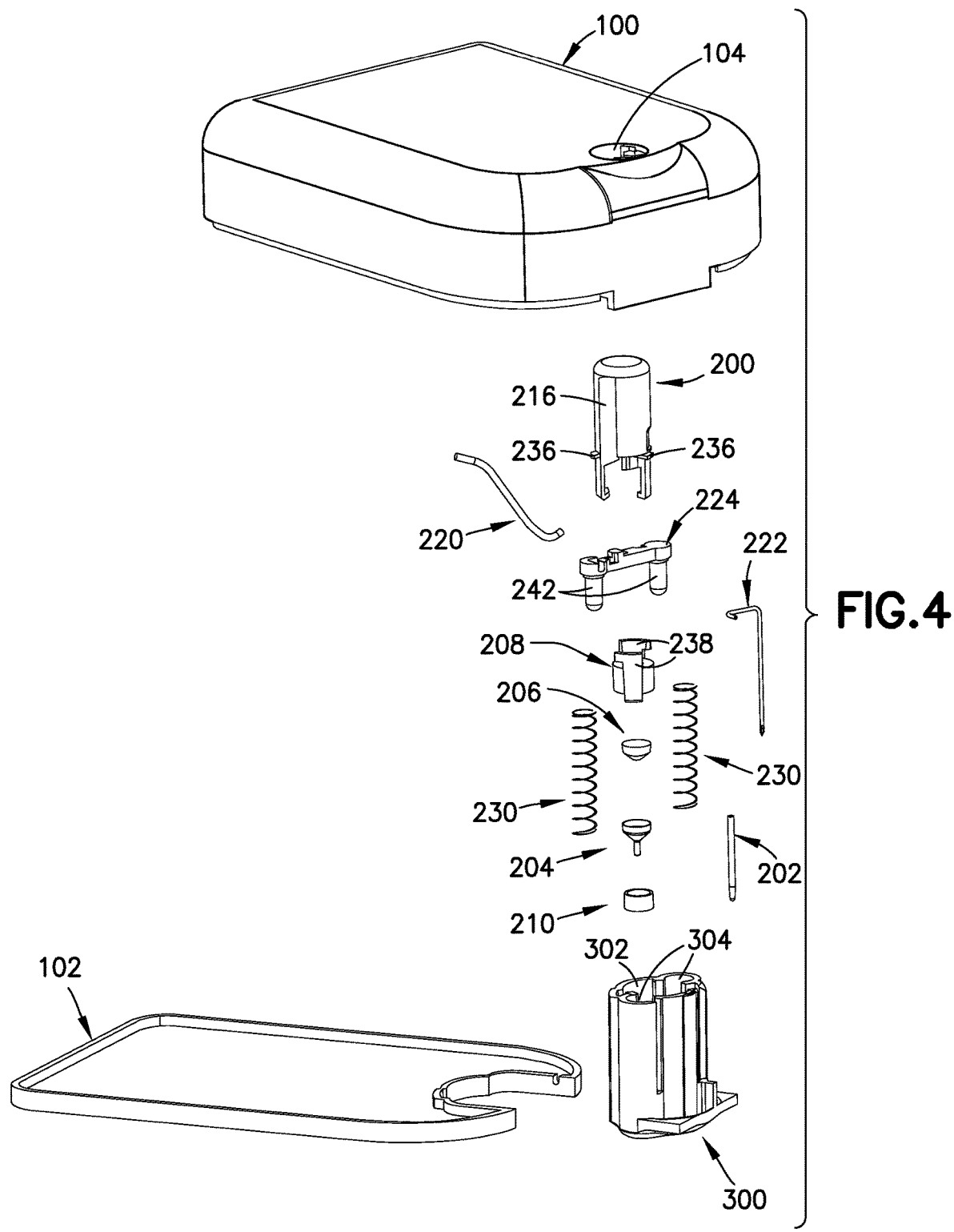
FIG. 4 is an exploded view of the insertion device of FIG. 1 in accordance with an embodiment of the present invention.

As shown in FIG. 4, the exemplary insertion device is assembled by stacking together a number of subassemblies which are trapped between the top housing 100 and the mechanism housing 300. FIG. 4 is a view of the insertion device of FIG. 1 in accordance with an embodiment of the present invention. The subassemblies of FIG. 4 and discussed in greater detail below include a catheter/septum subassembly, an introducer needle subassembly, and a button subassembly. Other features and functions of the insertion device that are well-known to those skilled in the art are omitted from the figures and discussion for clarity.

Figure 5:
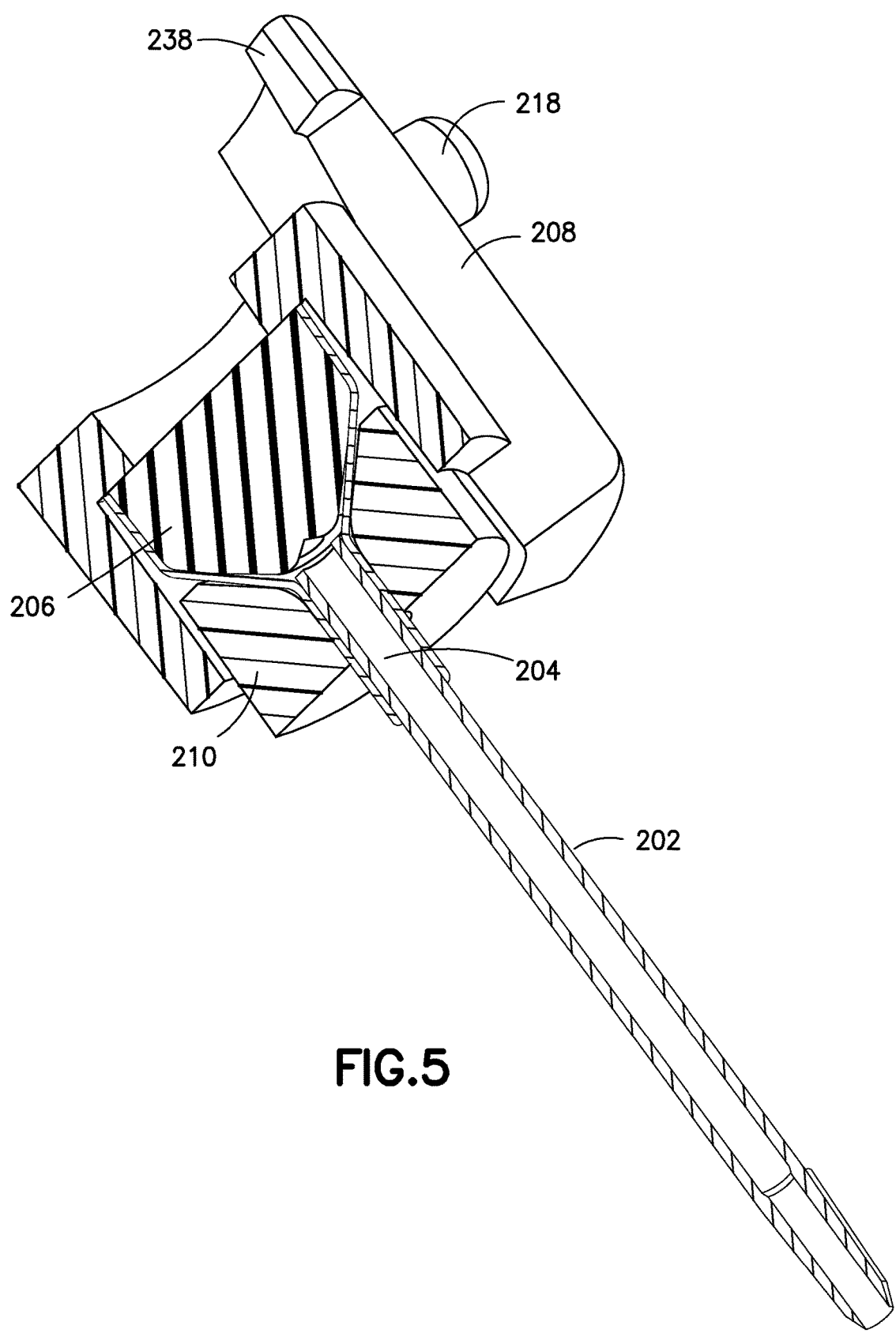
FIG. 5 is a sectional view of a catheter/septum subassembly of the insertion device of FIG. 1 in accordance with an embodiment of the present invention.

An exemplary catheter/septum subassembly is shown in FIG. 5. FIG. 5 is a sectional view of a catheter/septum subassembly of the insertion device of FIG. 1 in accordance with an embodiment of the present invention. As shown in FIG. 5, the catheter/septum subassembly is assembled by attaching a catheter 202 on a metal wedge 204, then inserting a septum 206 in the wedge and trapping it between a release collar 208 and a catheter wedge cap 210. The septum 206 is radially compressed by the wedge 204 and axially compressed by the release collar 208 to create a seal between the septum 206 and wedge 204. The catheter 202 can be a 24 G plastic catheter manufactured using FEP, and the release collar 208 and catheter wedge cap 210 can be manufactured using PTEG, but embodiments are not limited thereto. The wedge 204 can be manufactured using 305 stainless steel, and the septum 206 can be manufactured using isoprene, but embodiments are not limited thereto.

Figure 6:
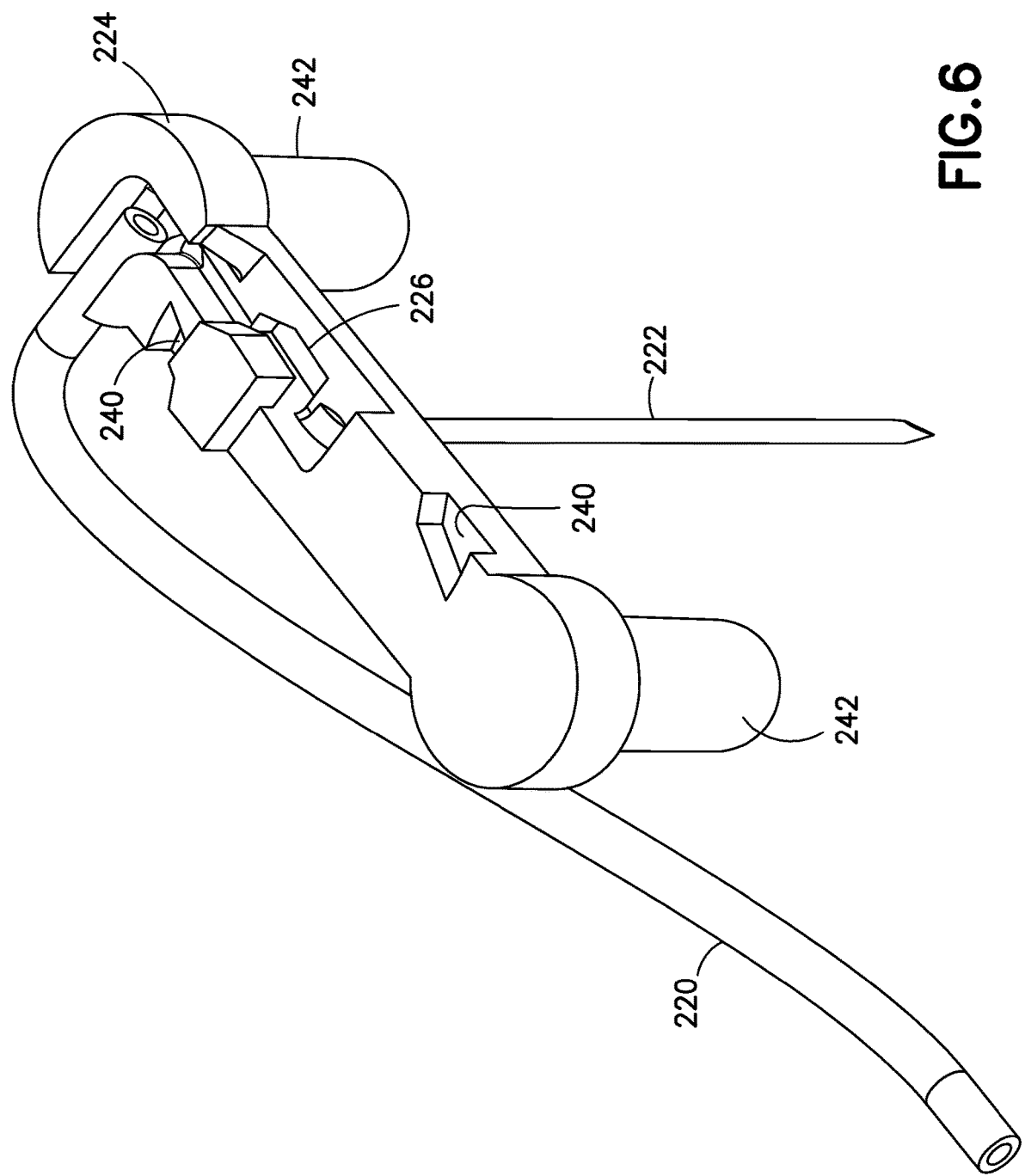
FIG. 6 is a view of an introducer needle subassembly, assembled from the top with plastic tubing, of the insertion device of FIG. 1 in accordance with an embodiment of the present invention.
Figure 7:
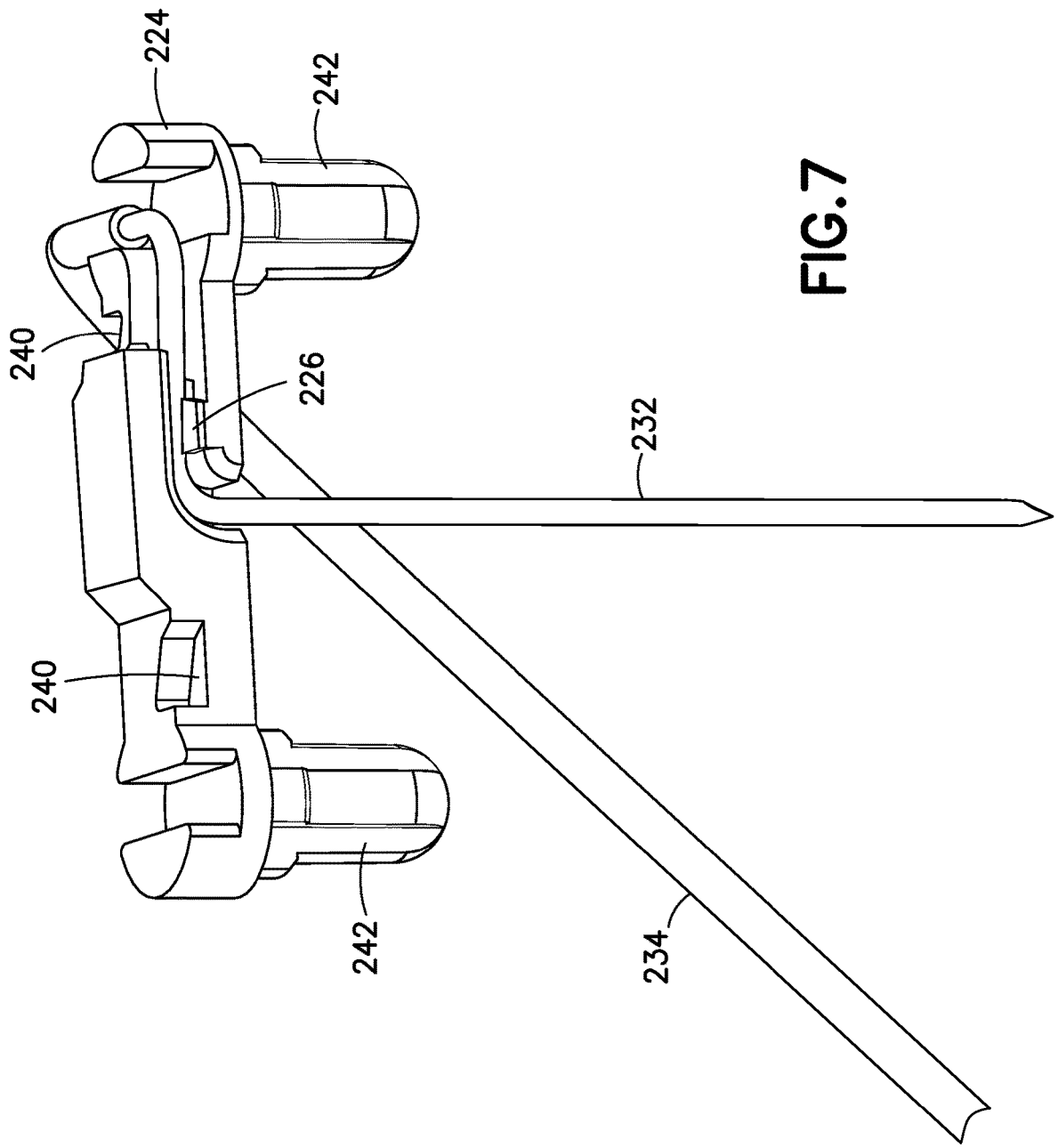
FIG. 7 is a view of another introducer needle subassembly, assembled from the side with no plastic tubing, of the insertion device of FIG. 1 in accordance with an embodiment of the present invention.

Exemplary introducer needle subassemblies are shown in FIGS. 6 and 7. FIG. 6 is a view of an introducer needle subassembly, assembled from the top with plastic tubing, and FIG. 7 is a view of another introducer needle subassembly, assembled from the side with no plastic tubing, of the insertion device of FIG. 1 in accordance with an embodiment of the present invention. The introducer needle subassembly of FIG. 6 and used in the following discussion is assembled by gluing or press-fitting tubing 220 on the non-patient end of the cannula or introducer needle 222, then placing the introducer needle through an introducer needle hub 224 and snapping it in place using any number of grooves, slots or detents 226 provided on a top surface of the introducer needle hub 224. The introducer needle 222 can be a hollow, 24 G needle or cannula manufactured using 304 stainless steel, and the introducer needle hub 224 can be manufactured using PETG, but embodiments are not limited thereto.

An alternative embodiment of the introducer needle subassembly of FIG. 7 is assembled using an introducer needle 232 with a long proximal end 234 that connects directly to the pump or reservoir (not shown). Eliminating the flexible plastic tubing in this embodiment makes assembly of the insertion device easier and reduces the risks associated with attaching the two parts, but requires a large loop on the proximal end 234 of the cannula to reduce the force needed to bend the cannula during insertion and retraction.

Figure 34:
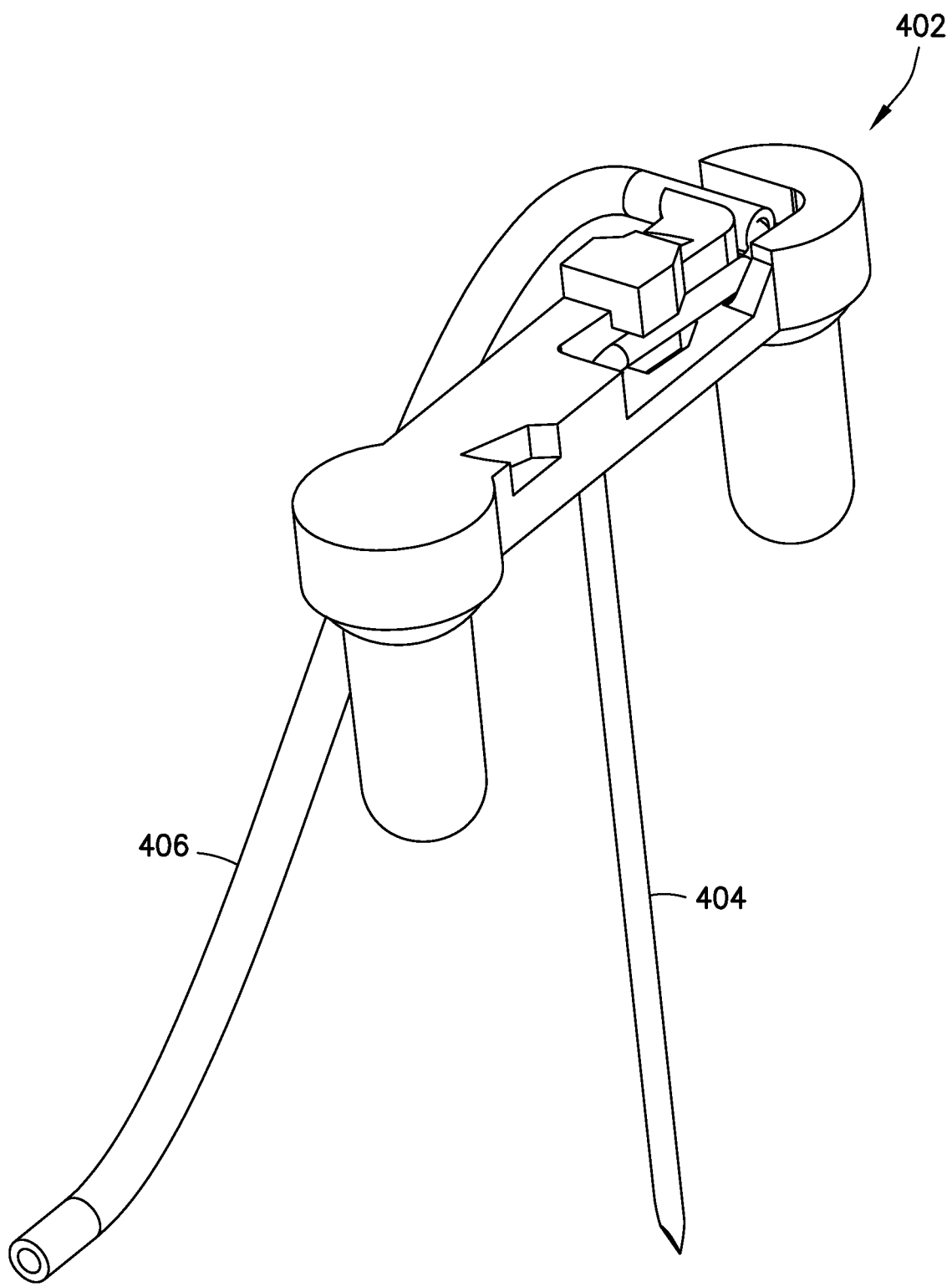
FIG. 34 is a view of another introducer needle subassembly of the insertion device of FIG. 1, wherein the needle is assembled from the top with plastic tubing in accordance with an embodiment of the present invention.
Figure 35:
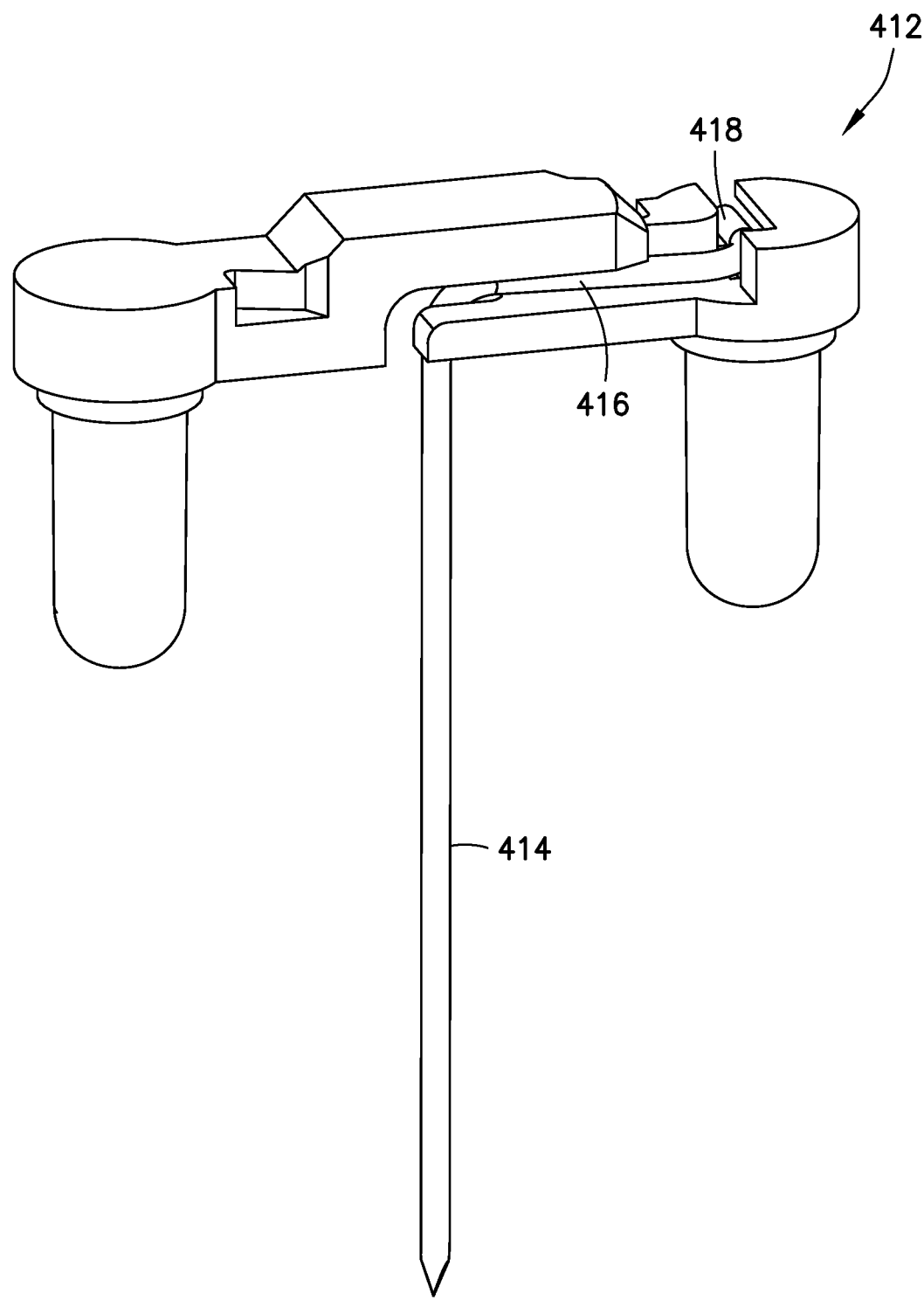
FIG. 35 is a view of another introducer needle subassembly of the insertion device of FIG. 1, wherein the needle is assembled from the side with no plastic tubing in accordance with an embodiment of the present invention.

Other alternate embodiments of the introducer needle subassembly are shown in FIGS. 34-47. Such alternate introducer needle subassembly embodiments make assembly of the parts in high speed manufacture easier. FIGS. 34 and 35 illustrate two introducer hub subassembly embodiments. As noted above, the introducer hub pushes the introducer needle during insertion, loads the compression springs during insertion and retracts the introducer needle after the plastic catheter is inserted FIG. 34 is an view of an introducer needle subassembly 402 of the insertion device of FIG. 1, wherein the needle 404 is assembled from the top with plastic tubing 406, and FIG. 35 is an view of an introducer needle subassembly 412 of the insertion device of FIG. 1, wherein the needle 414 is assembled from the side with no plastic tubing.

In the embodiments of FIGS. 34 and 35, the introducer hub 402, 412 is small in order to keep the insertion mechanism small, which presents challenges in molding the part and assembling the introducer needle 404, 414. Standard straight needle cannulation and gluing processes are not possible due to the size limitations, so the needle 404, 414 must include a bend and be attached to the introducer hub 402, 412 by some method. Further, the handling and assembling such a small needle 404, 414 can be difficult and the following assemblies are provided to simplify the manufacturing of such subassemblies.

Figure 36:
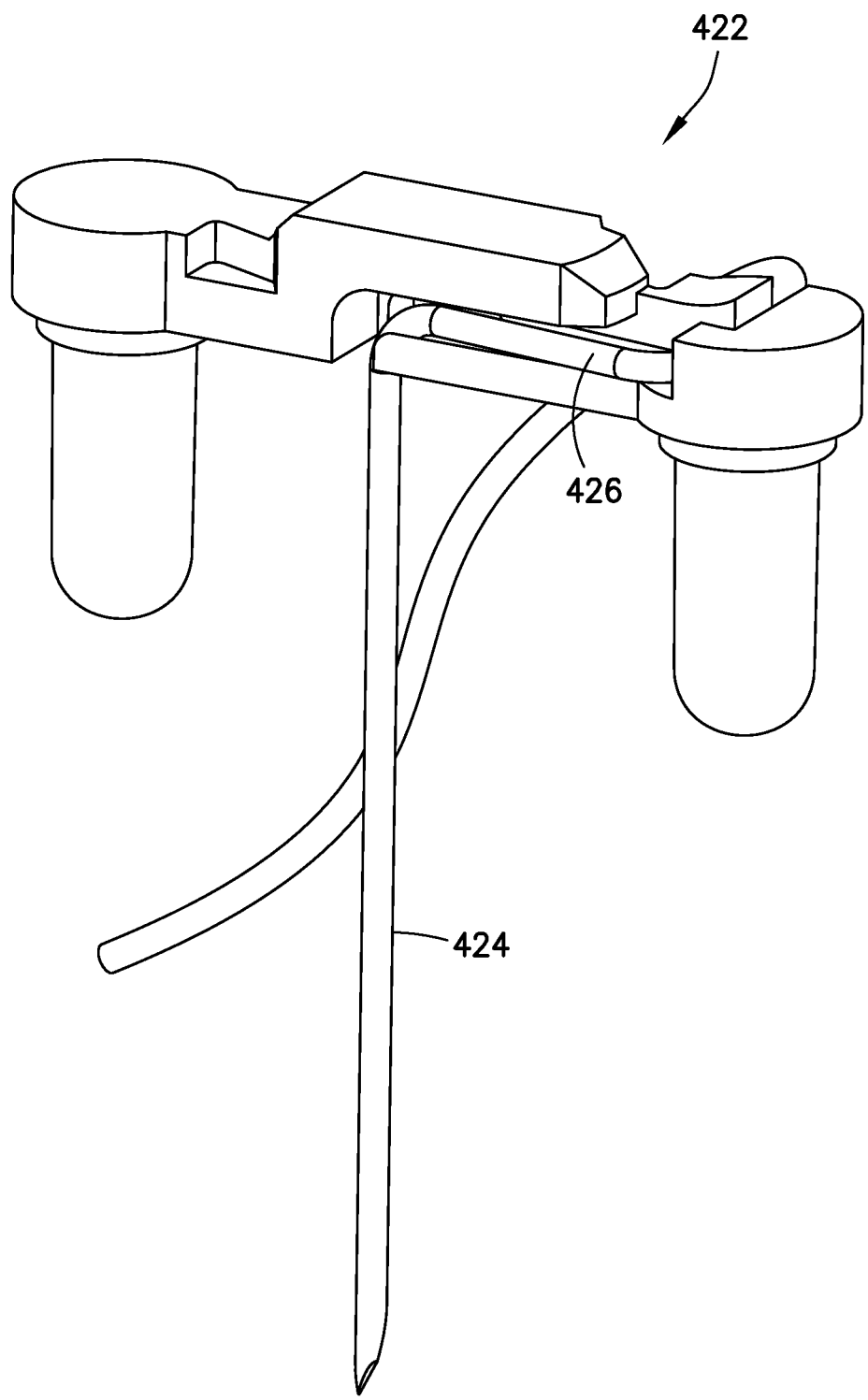
FIG. 36 is a view of a unidirectional introducer needle subassembly of the insertion device of FIG. 1 in accordance with an embodiment of the present invention.
Figure 37:
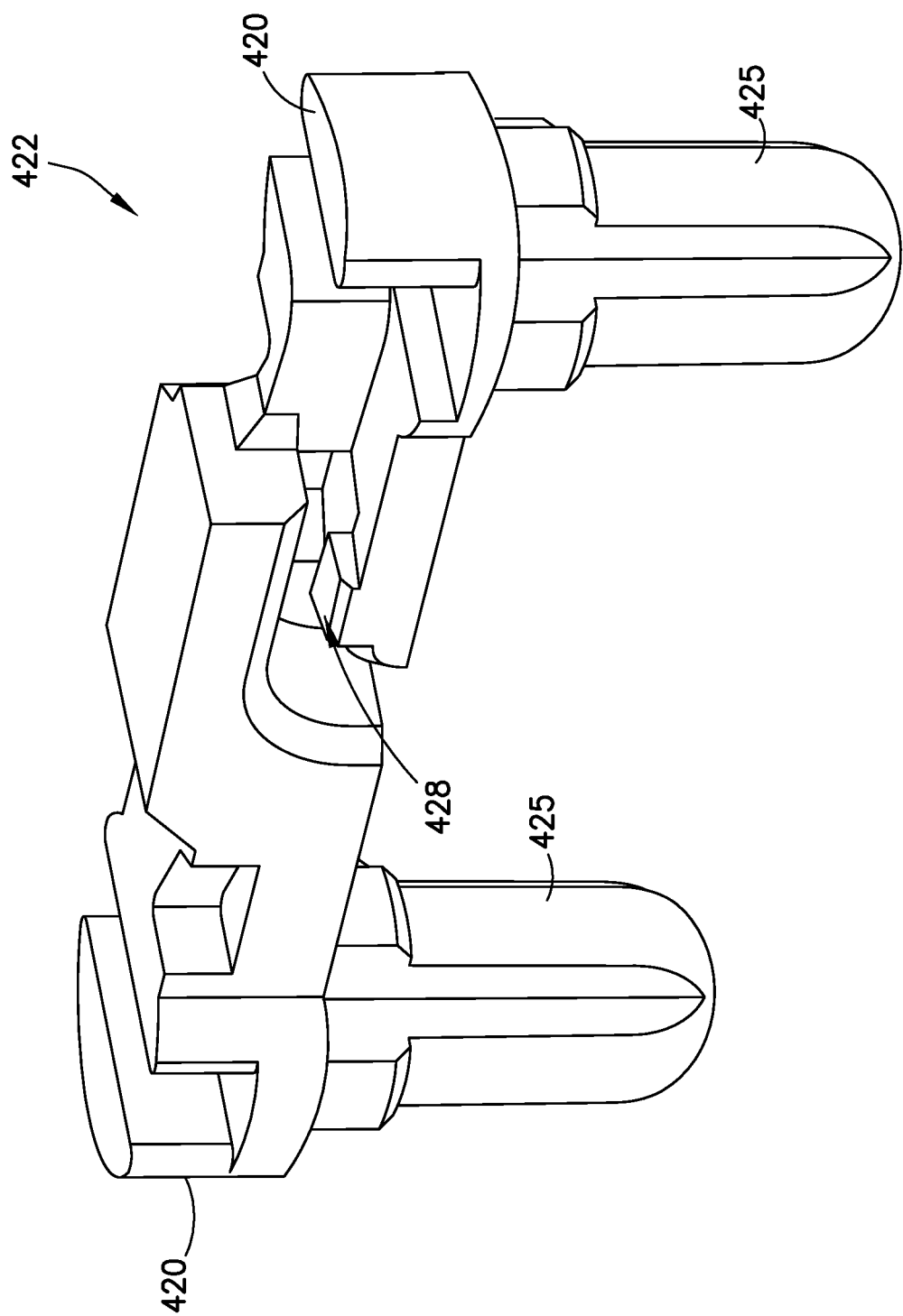
FIG. 37 is another view of the unidirectional introducer needle subassembly of FIG. 36 in accordance with an embodiment of the present invention.
Figure 38:
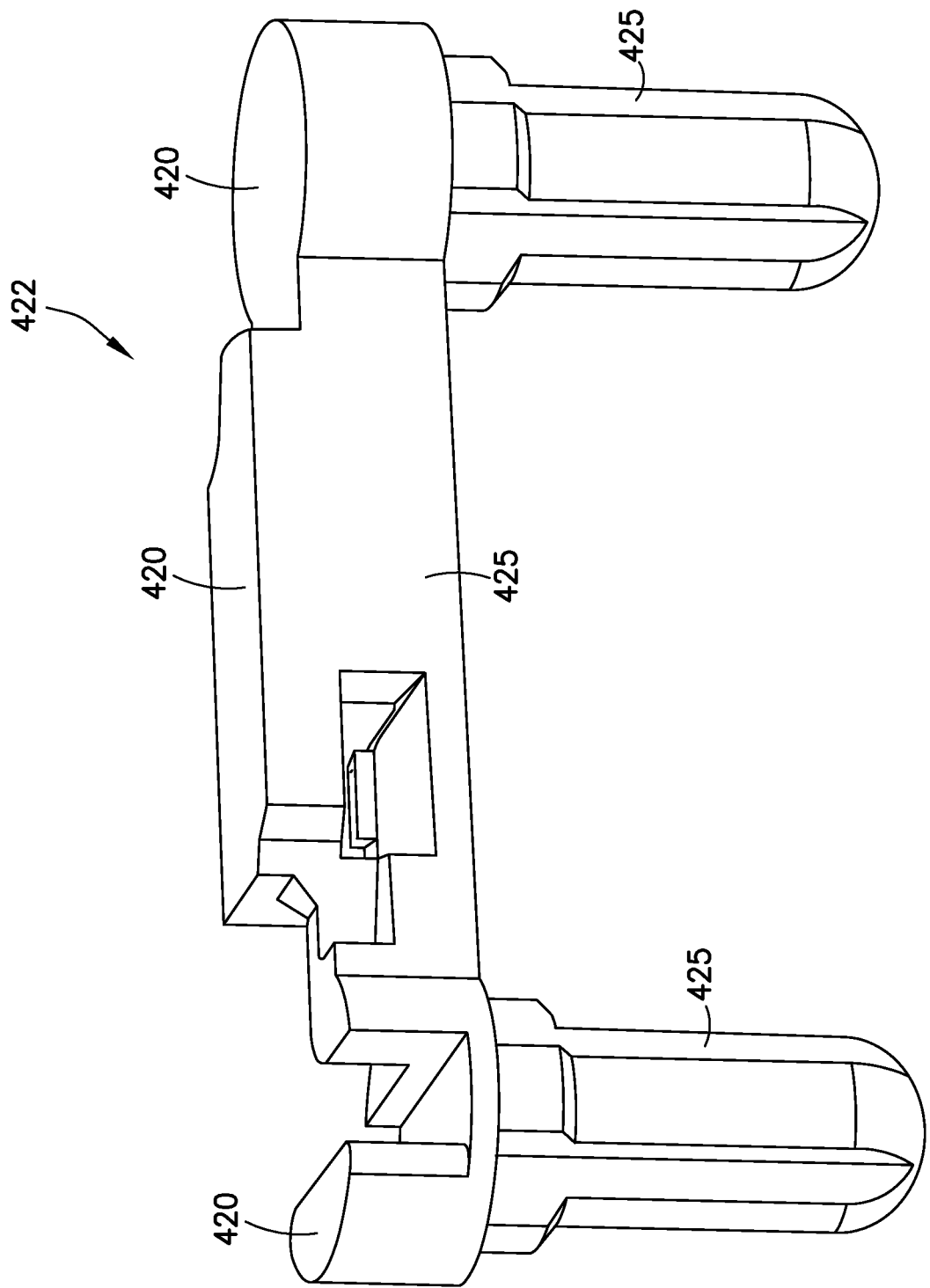
FIG. 38 is a view of another introducer needle subassembly of the insertion device of FIG. 1, with an insert molded introducer hub with a post-processed introducer needle bend in accordance with an embodiment of the present invention.
Figure 39:
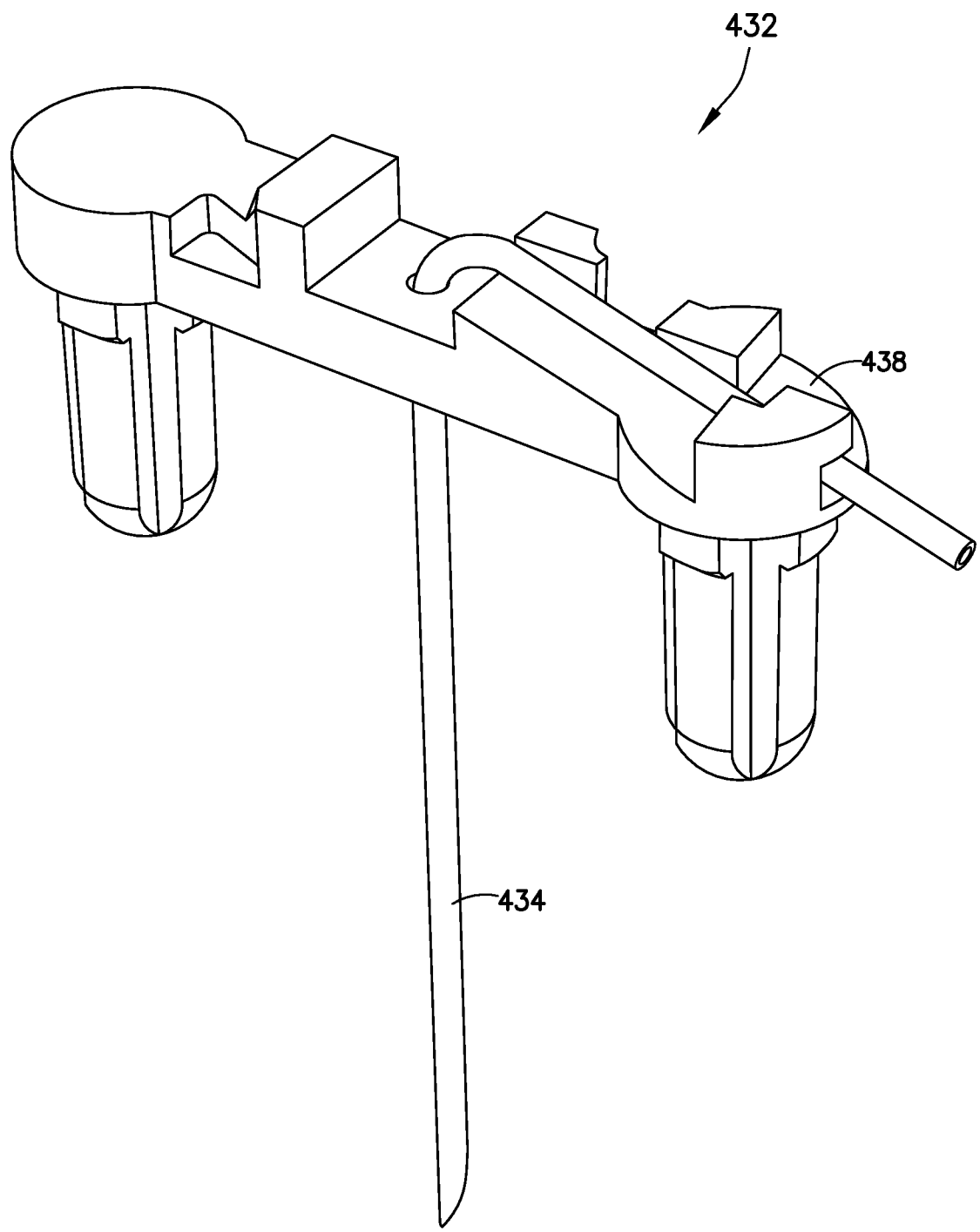
FIG. 39 is another view of the introducer needle subassembly of FIG. 38 showing the inserter mold post-process introducer needle bend in accordance with an embodiment of the present invention.

FIGS. 36-38 show a unidirectional assembly introducer hub embodiment 422 that is similar to the embodiment of FIG. 35. The needle 424 is assembled into the introducer hub 422 from the side. The embodiment of FIG. 35 assembly requires multiple complex motions of the introducer needle 414; the 90° bend portion of the needle 414 is inserted into the receiving slot 416 in the introducer hub 412 then the short arm 418 is rotated while bending it away from the distal end and snaped into place. The unidirectional assembly intorducer hub 422 of FIG. 36 below is assembled by translating the introducer needle 424 into the slot 426 in the introducer hub 422. This single motion makes automated assembly easier. The long distal straight section of the introducer needle 424 is, for example, held between plates (not shown) to translate the needle 424 during assembly and prevent rotation. The introducer hub 422 can be molded using, for example, an A-B mold. The snap 428 in the introducer hub 422 that retains the introducer needle 424 is molded by a shut off. As shown in FIGS. 37 and 38, a front or left side structure 420 corresponds to one side of the mold, and a rear or right side structure 425 corresponds to the other side of the mold.

Figure 40:
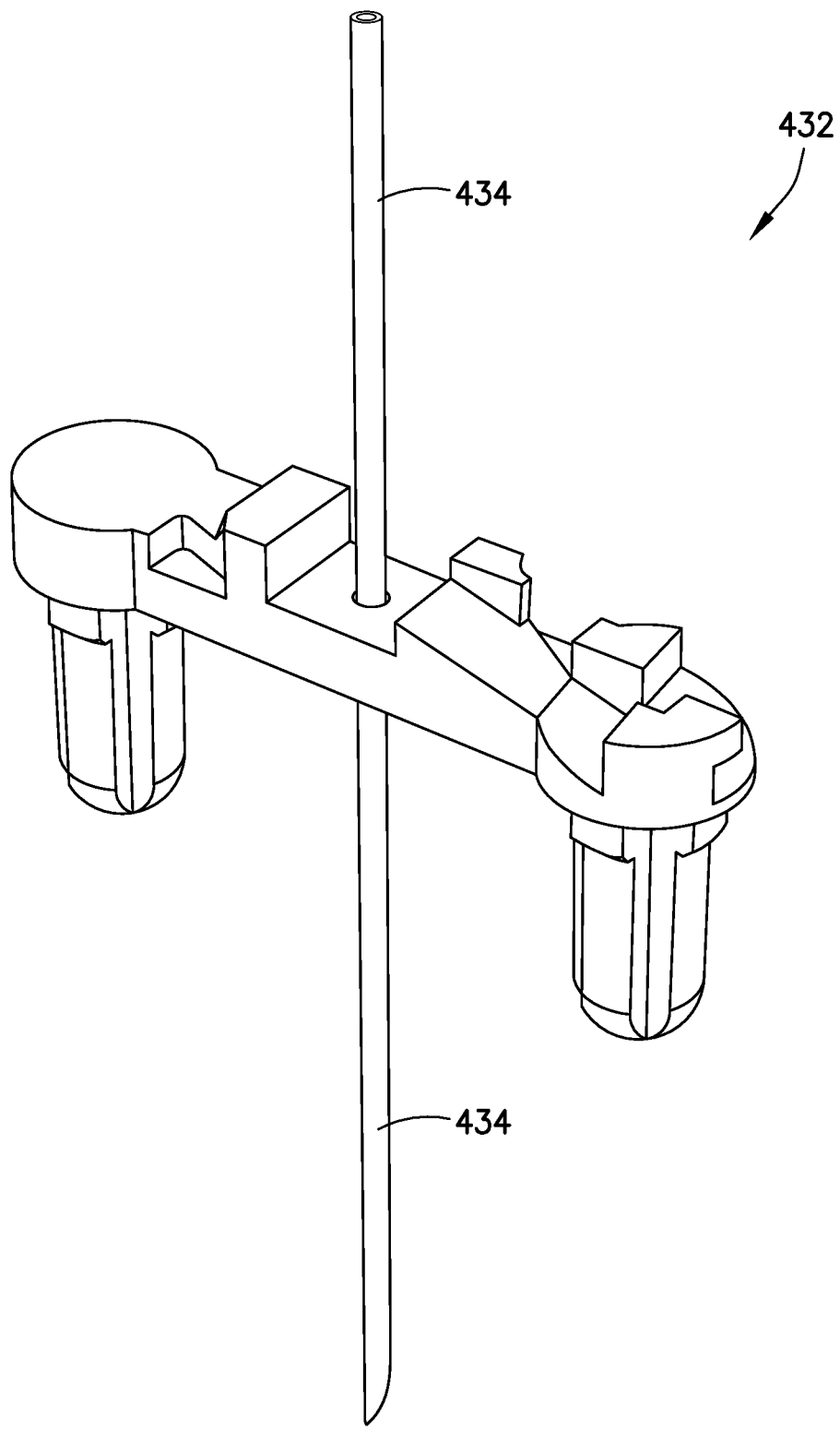
FIG. 40 is another view of the introducer needle subassembly of FIG. 38 showing the insert molded needle in accordance with an embodiment of the present invention.
Figure 41:
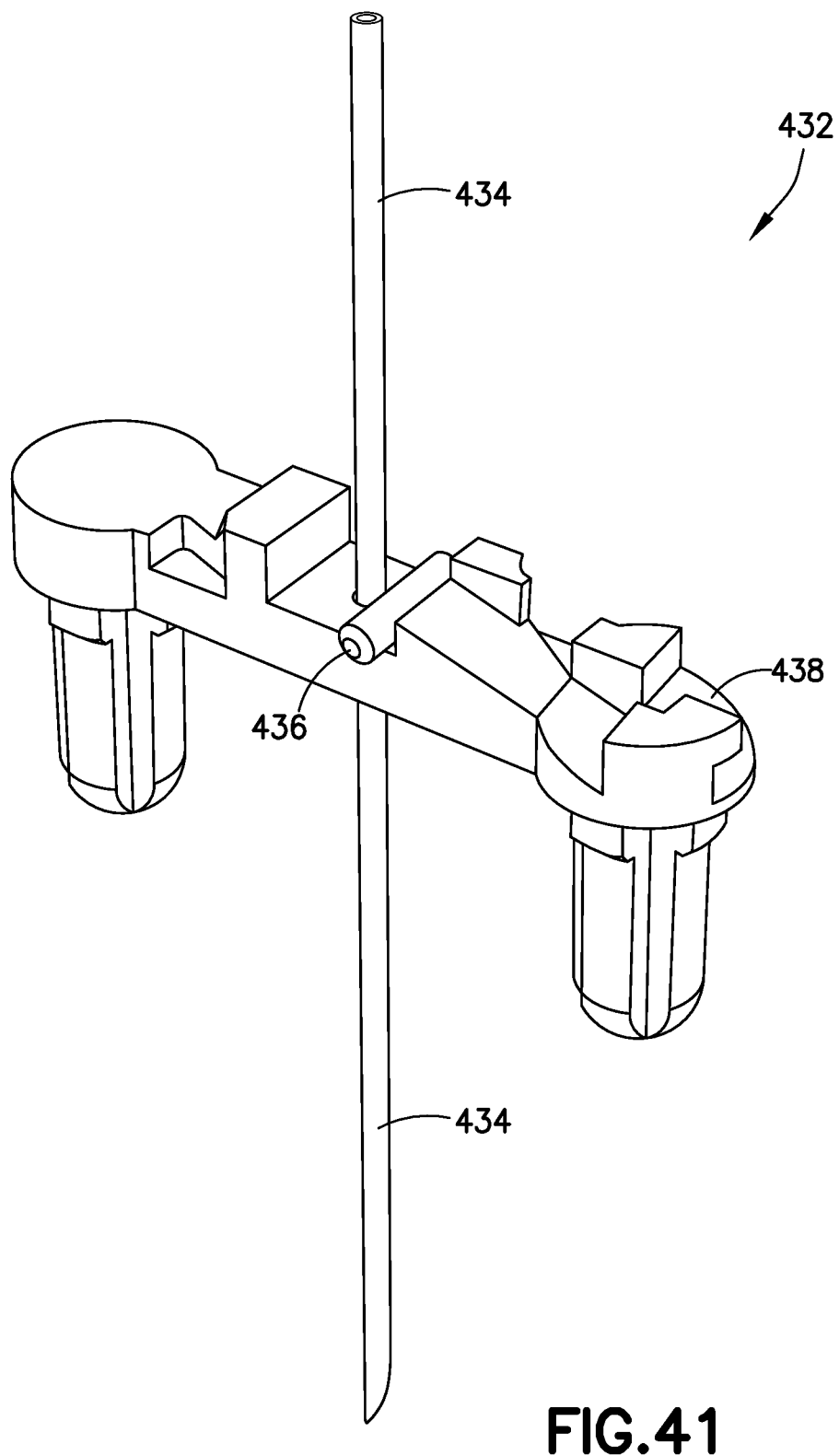
FIG. 41 is another view of the introducer needle subassembly of FIG. 38 showing the insertion of a steel dowel rod during the needle bending step after the needle is insert molded in accordance with an embodiment of the present invention.
Figure 42:
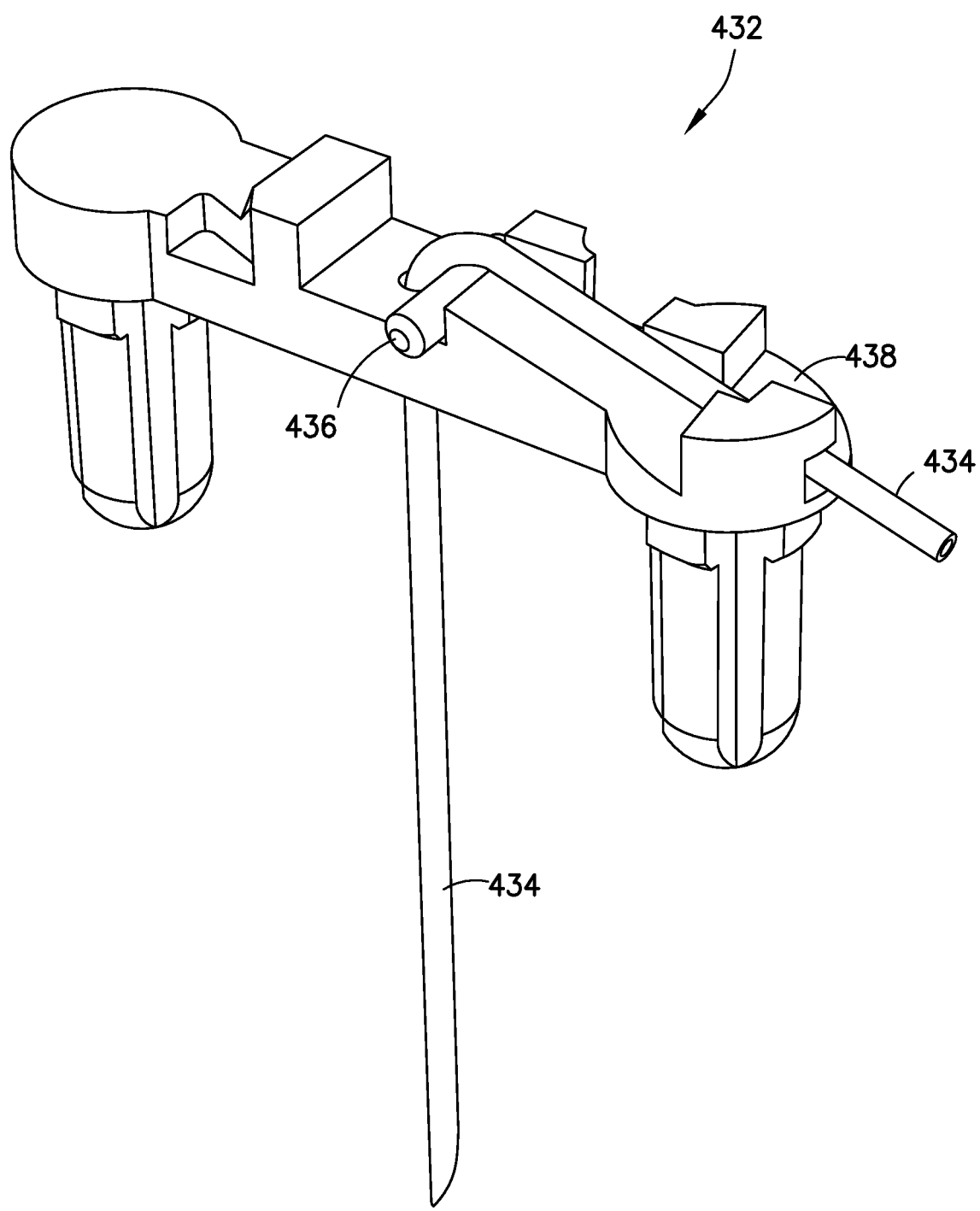
FIG. 42 is another view of the introducer needle subassembly of FIG. 38 showing the bend of the straight introducer needle over the steel dowel rod during assembly in accordance with an embodiment of the present invention.
Figure 43:
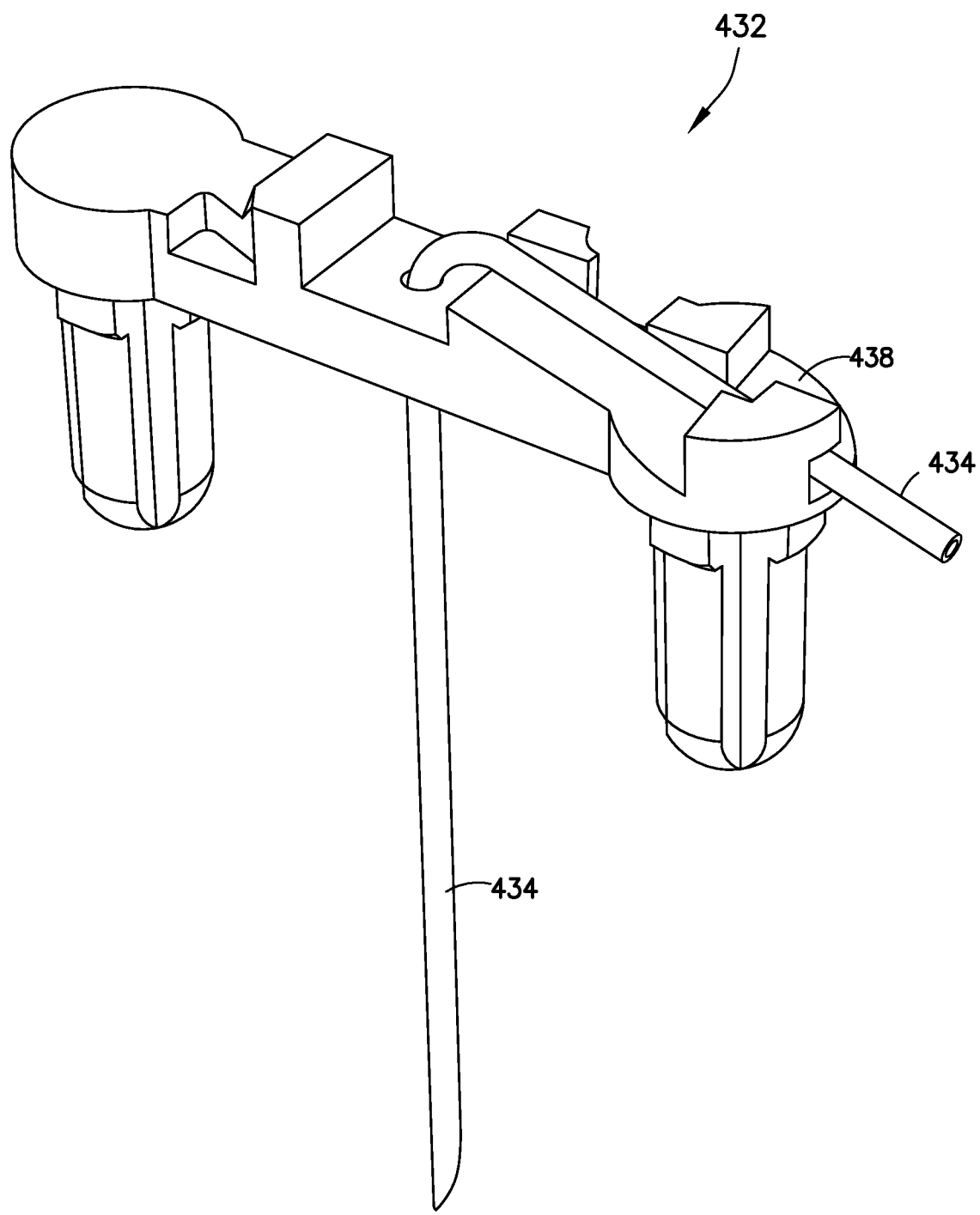
FIG. 43 is another view of the introducer needle subassembly of FIG. 38 showing the removal of the steel dowel rod during assembly in accordance with an embodiment of the present invention.
Figure 44:
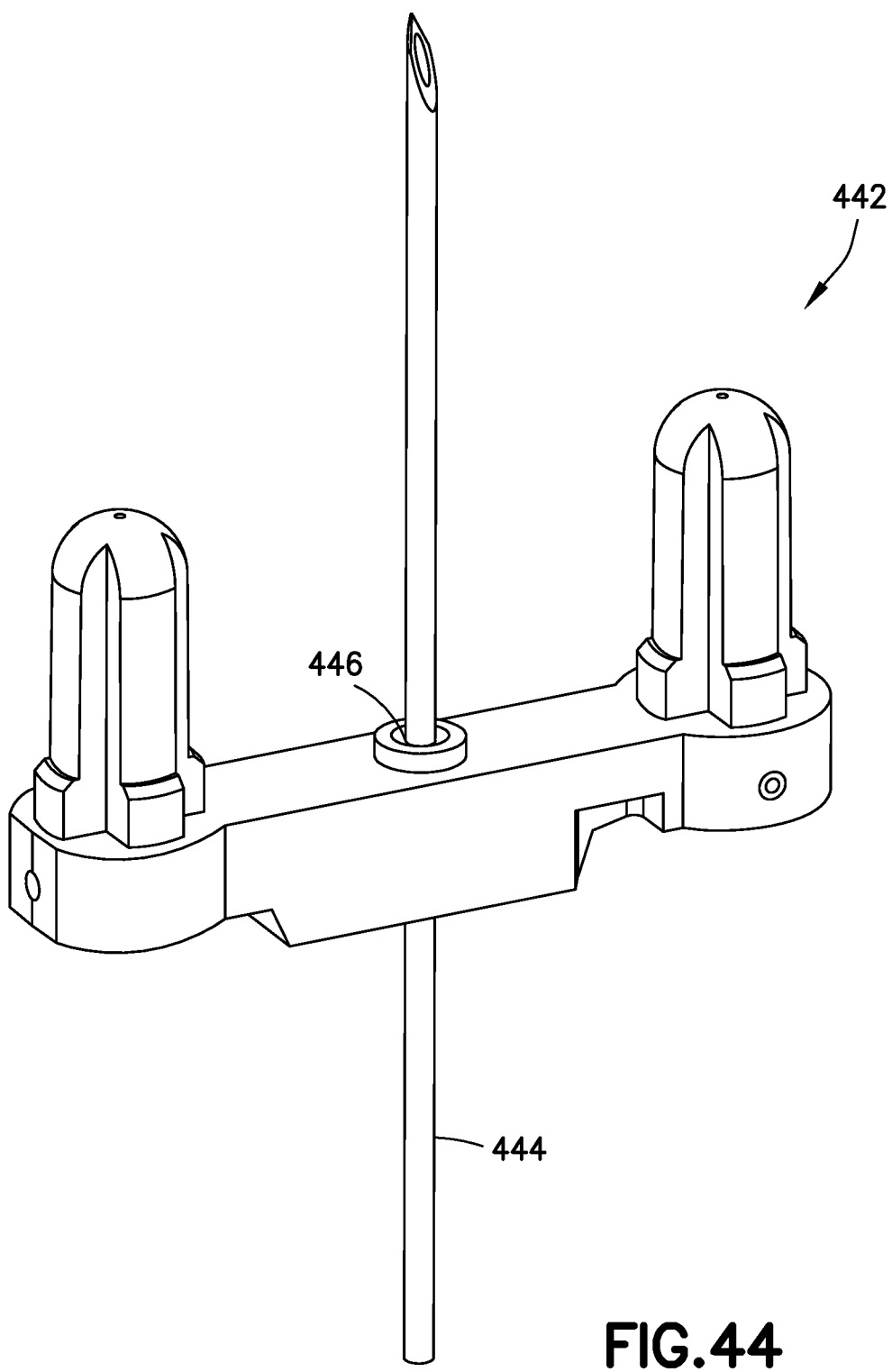
FIG. 44 is a bottom view of another introducer needle subassembly of the insertion device of FIG. 1 showing the insertion of a straight introducer needle during assembly in accordance with an embodiment of the present invention.

FIGS. 39-43 show an insert molded introducer hub 432 with a post-processed introducer needle 434 bend. A straight introducer needle 434 is insert molded with the introducer hub 432 as shown in FIG. 40, and a post-process fixture with a steel dowel rod 436 is located on an upper surface of the introducer hub 432 as shown in FIG. 41. As shown in FIG. 42, the introducer needle 434 is then bent over the dowel rod 436 and snapped into the introducer hub 432 using snap 438 to prevent the needle 434 from springing back. The exemplary snap geometry is for illustration purposes and the invention is mot limitede thereto. The material, location, and diameter of the dowel rod (if necessary) 436 is sufficient to keep the bent portion of the needle 434 open and to avoid crimping for fluid flow after the bend process. Then, as shown in FIG. 43, the dowler fixture or rod 436 is removed and the subassembly 432 is ready for tubing assembly.

Figure 45:
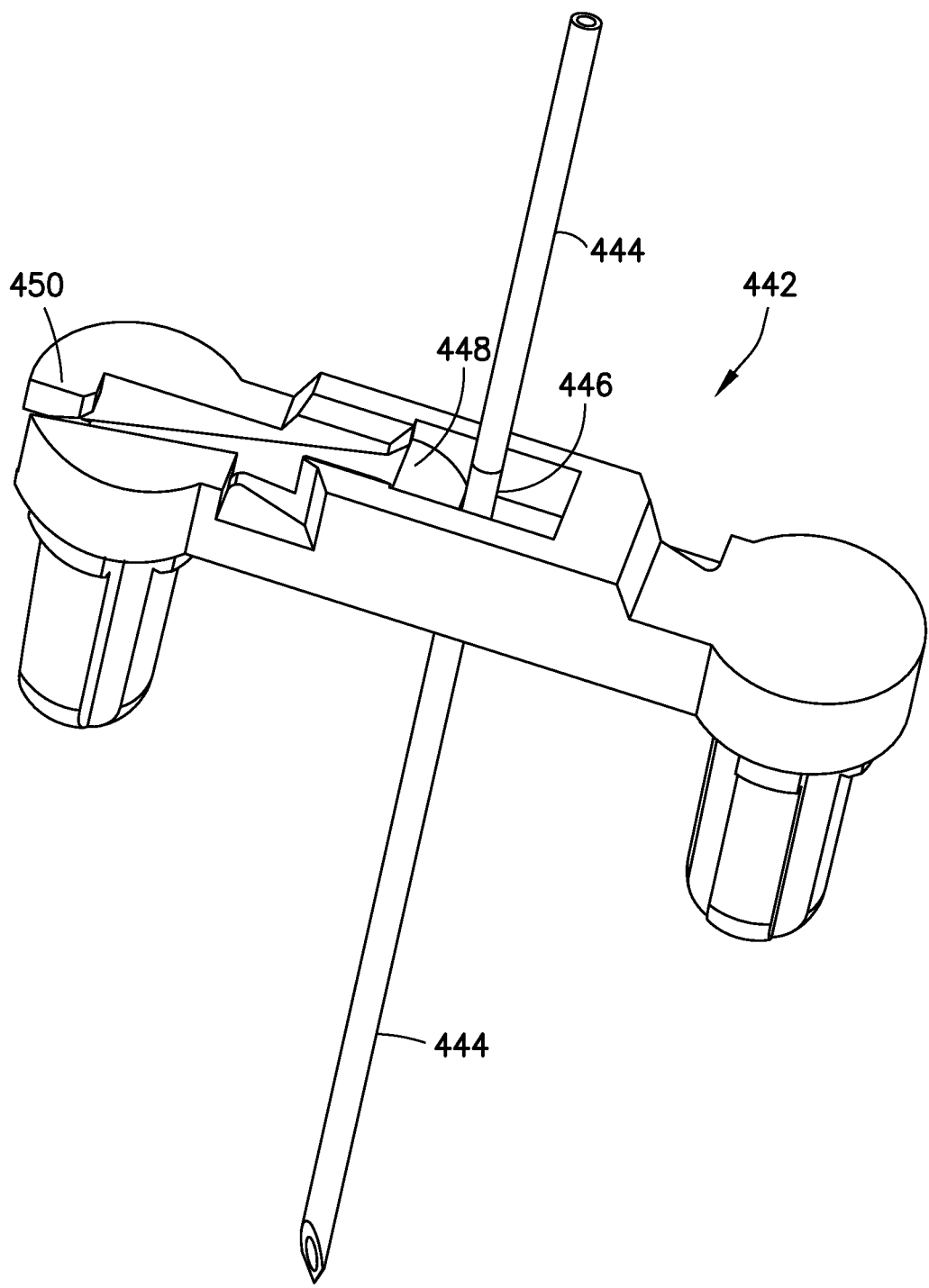
FIG. 45 is a top view of the introducer needle subassembly of FIG. 44 showing the insertion of a straight introducer needle during pre-bend assembly in accordance with an embodiment of the present invention.
Figure 46:
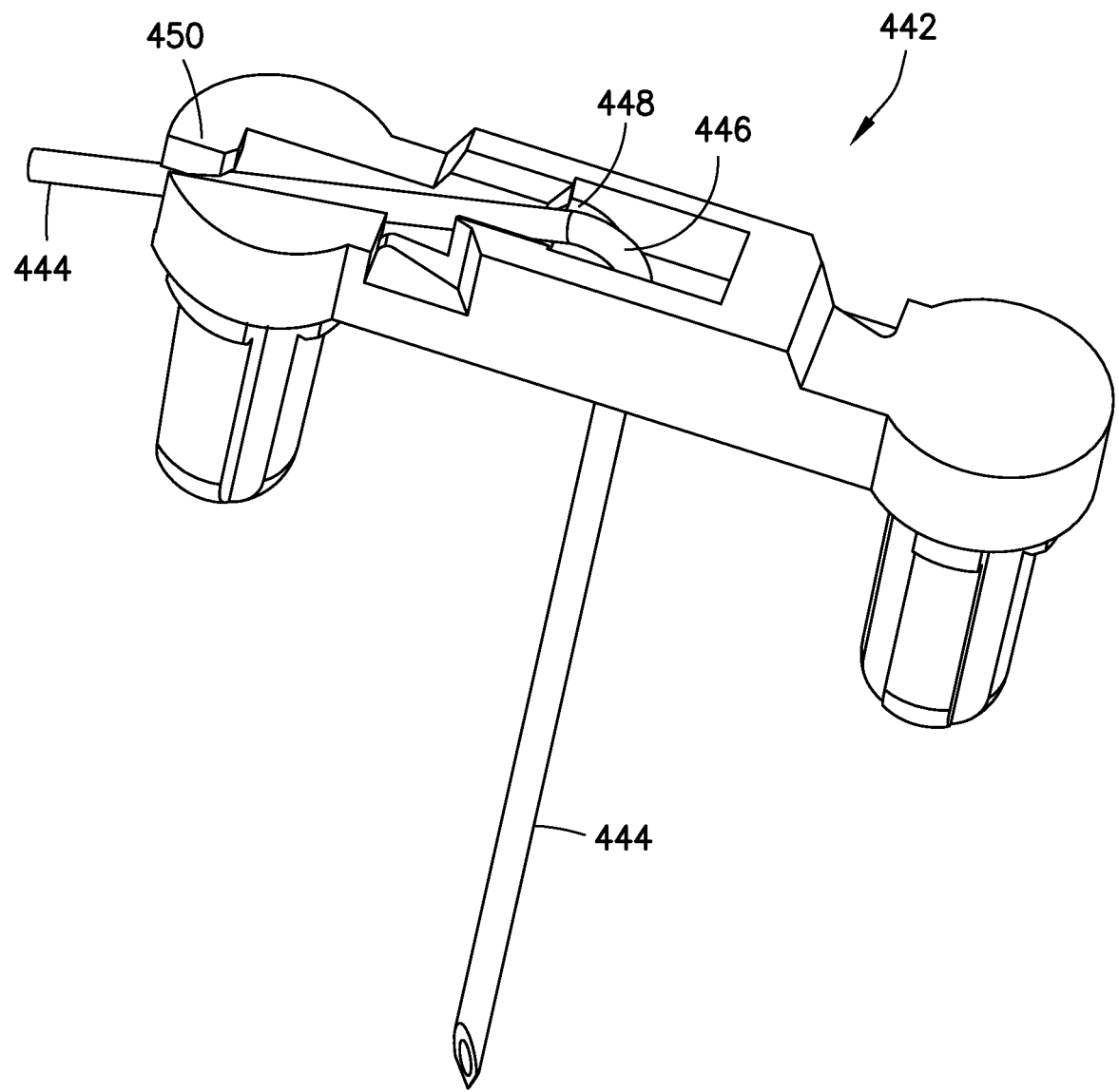
FIG. 46 is a top view of the introducer needle subassembly of FIG. 44 showing the straight introducer needle during post-bend assembly in accordance with an embodiment of the present invention.
Figure 47:
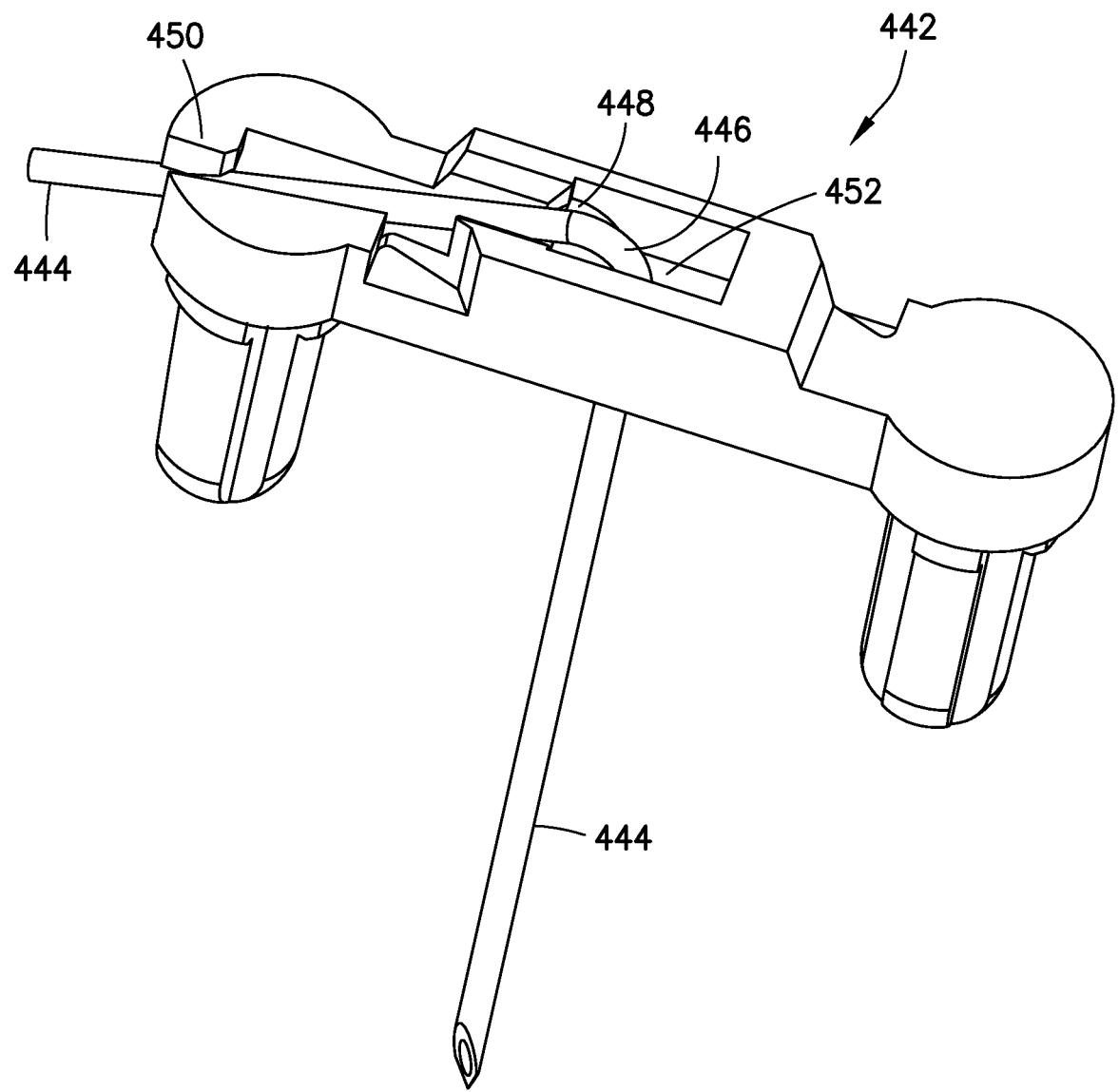
FIG. 47 is a top view of the introducer needle subassembly of FIG. 44 showing the straight introducer needle during glue fill assembly in accordance with an embodiment of the present invention.

FIGS. 44-47 show a cannulated straight needle introducer hub 442 with an introducer needle 444 that is glued and bent post-process. A straight introducer needle 444 is cannulated using standard processes by inserting the dull end of the needle 444 through a chamfered hole 446 in the introducer hub 442 as shown in FIG. 45. The distance from the hub to the tip can be be set using, for example, a vision system and camera or other suitable measurement system. As shown in FIG. 46, the dull side of the needle 444 is then bent over a rounded feature or shoulder 448 on the introducer hub 442 and snapped into into the introducer hub 442 using snap 450 to prevent the needle 444 from springing back.

The radius of the rounded feature or shoulder 448 is sufficiently large to avoid crimping or otherwise reducing the inner diameter of the needle 444 and ensure that fluid could flow through the bend in the needle 444. The clearance in the introducer hub through hole 446 required for assembly and the spring-back from bending process, prevents the needle from meeting the tolerance for the 90° bend angle after the first bend, so a second distal end bend would be required to correct the angle without the provision of the rounded feature or shoulder 448. This second bend however, would release the spring force exerted by the introducer needle on the introducer hub capturing snaps caused by the spring back from the first bend. Alternately, the through hole 446 can be molded at an angle to the insertion direction so the needle would meet the 90° bend tolerance after the first bend process which would eliminate the need for a secondary bend. However, this solution would require a more complicated mold since the through hole 446 mold pull direction would be different from the primary mold pull directions.

Accordingly, the exemplary embodiment provides that rounded feature or shoulder 448, such that the dull side of the needle 444 is then bent over a rounded feature or shoulder 448 on the introducer hub 442 and snapped into into the introducer hub 442 using snap 450 to prevent the needle 444 from springing back. In a final assembly step, glue is then dispensed in the glue well 452 shown in FIG. 47. The glue would secure the needle 444 from moving relative to the introducer hub 442 and catheter during insertion.

Figure 8:
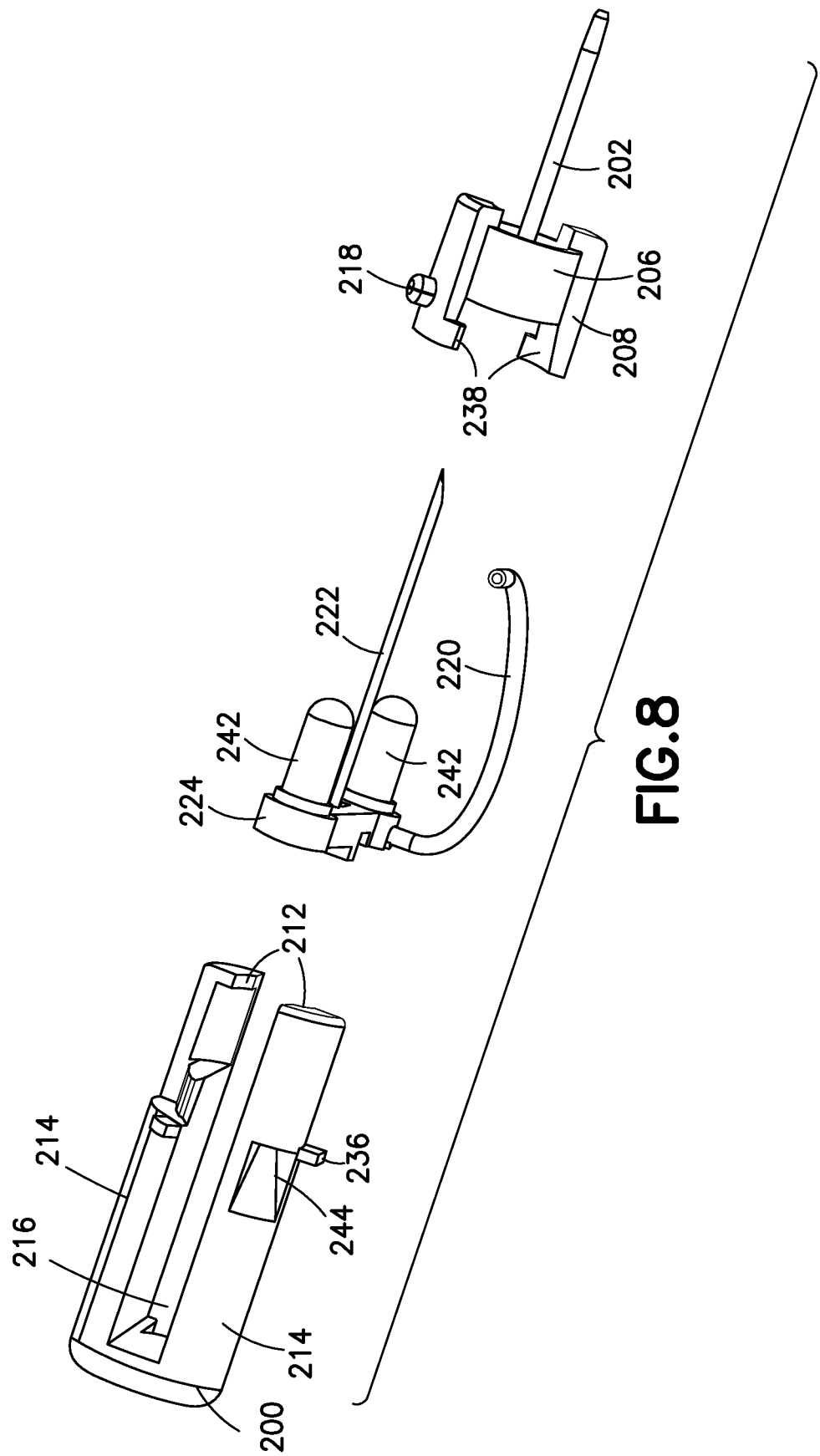
FIG. 8 is a view of the assembly of the button subassembly of the insertion device of FIG. 1, including the catheter/septum subassembly of FIG. 5 and introducer needle subassembly of FIG. 6, in accordance with an embodiment of the present invention.
Figure 9:
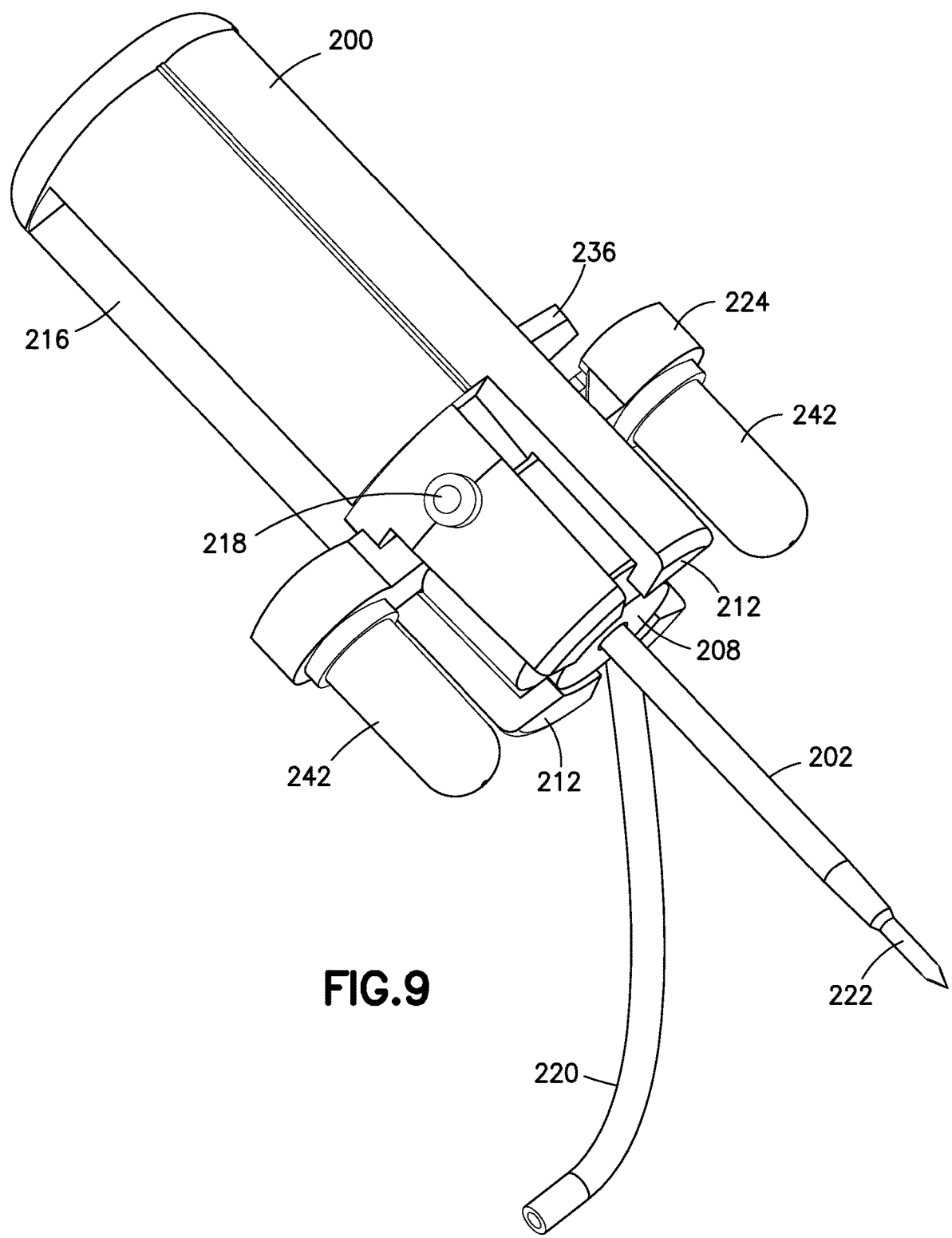
FIG. 9 is a view of the completed button subassembly of the insertion device of FIG. 1 in accordance with an embodiment of the present invention.

An exemplary button subassembly is shown in FIG. 8. FIG. 8 is a view of the assembly of the button subassembly of the insertion device of FIG. 1, including the catheter/septum subassembly and introducer needle subassembly, and FIG. 9 is a view of the completed button subassembly of the insertion device of FIG. 1 in accordance with an embodiment of the present invention. The button subassembly is built by combining the catheter/septum subassembly and introducer needle subassembly with the button 200. As described in greater detail below, once assembled, the introducer needle subassembly cannot be rotated in the button 200. The catheter/septum subassembly can be rotated in the button 200 and in doing so, can be rotated from a position secured with the introducer needle subassembly, to a position freed from the introducer needle subassembly.

Specifically, the button subassembly is built by inserting the introducer needle 222 of the introducer needle subassembly through the septum 206 and catheter 202 of the catheter/septum subassembly. The catheter/septum subassembly is then secured to the introducer needle subassembly by rotating the catheter/septum subassembly up to 20 degrees or more to lock the detents or teeth 238 on the release collar 208 into grooves or slots 240 on the top surface of the introducer needle hub 224, which couples the introducer needle hub 224 and catheter/septum subassembly. In this position the teeth 238 are locked over the top the introducer needle hub 224 so as the button 200 is pressed down, the introducer needle hub 224 also moves down. This results in the introducer needle 222 and catheter 202 being moved simultaneously for insertion into a user skin surface (not shown).

The button subassembly is then completed by snapping the release collar 208 into the button 200 to secure the introducer needle subassembly and the catheter/septum subassembly in place. To do so, the button 200 can include detents 212 on deflectable arms 214 to deflect and then capture therebetween the lower edge of the release collar 208 as shown in FIG. 9. Between the deflectable arms 214, slots 216 are provided in the button 200 to allow linear travel of the introducer needle hub 224 relative to the button 200, but prohibit rotational movement of the introducer needle hub relative to the button 200. The slots 216 in the button 200 also allow rotational movement of the radial operation pin 218 of the release collar 208 relative to the button 200 as described in greater detail below. In the exemplary embodiment, a substantially cylindrical-shaped pin 218 is shown on an outer circumference of the release collar 208. However, in this or other embodiments of the present invention, any detent or projection of the release collar which can operate with the helical pathway can be provided as the radial operation pin.

Figure 10:
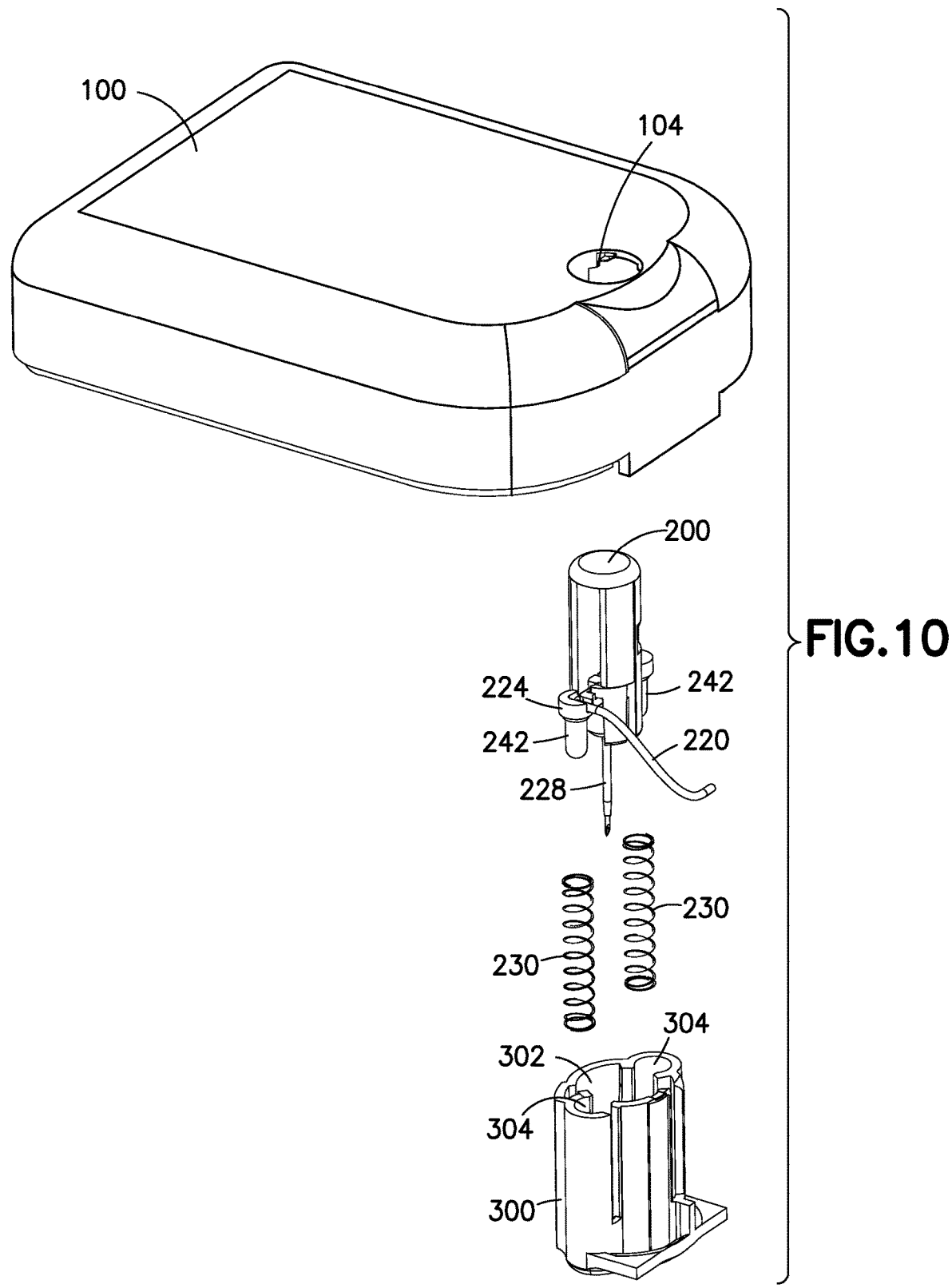
FIG. 10 is a view of the assembly of the button subassembly and springs into the housing of the insertion device of FIG. 1 and illustrating the use of temporary protective tubing on the catheter in accordance with an embodiment of the present invention.
Figure 11:
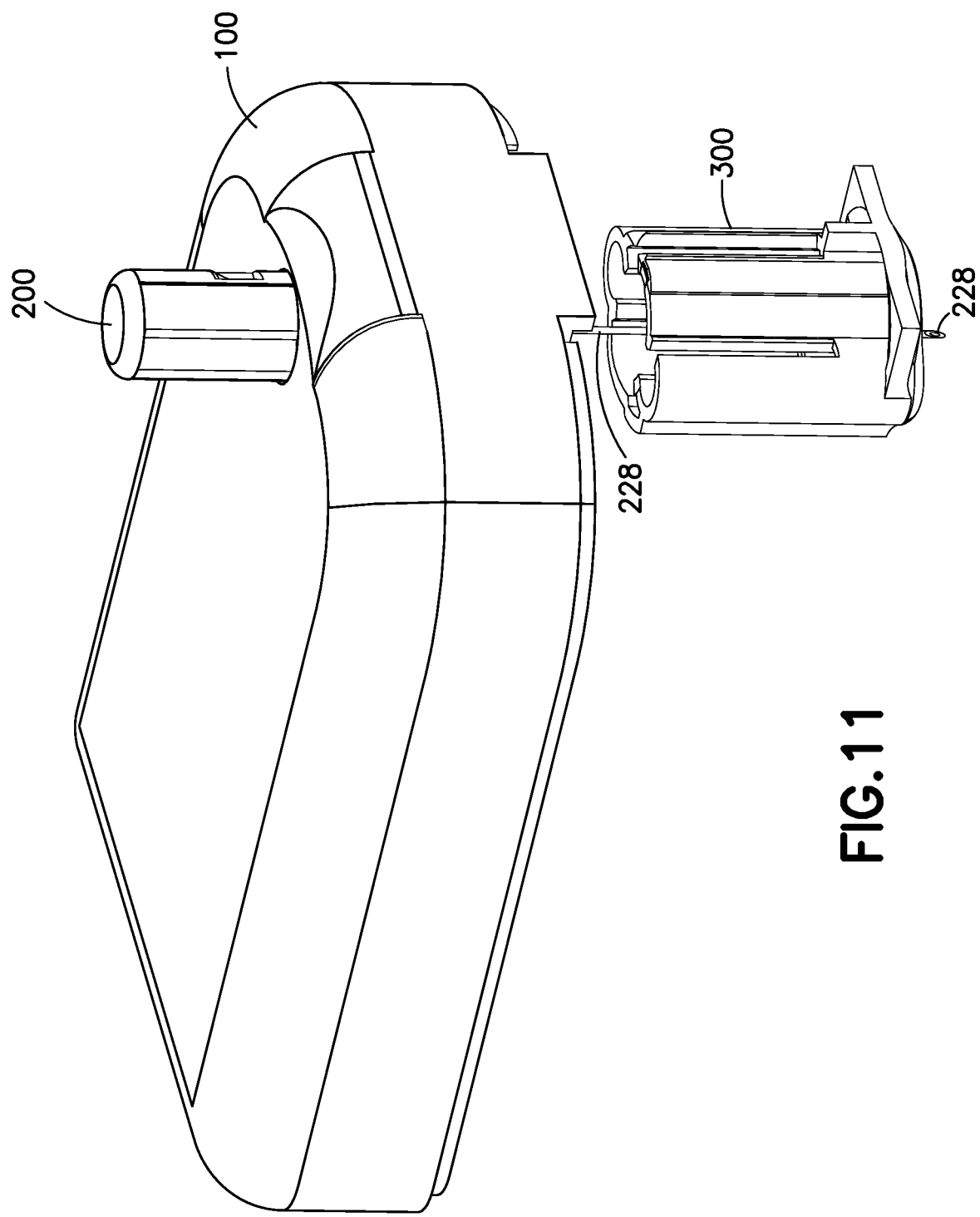
FIG. 11 is a view of the partially complete assembly of the button subassembly and springs into the housing of the insertion device of FIG. 1 and illustrating the use of temporary protective tubing on the catheter in accordance with an embodiment of the present invention.
Figure 12:
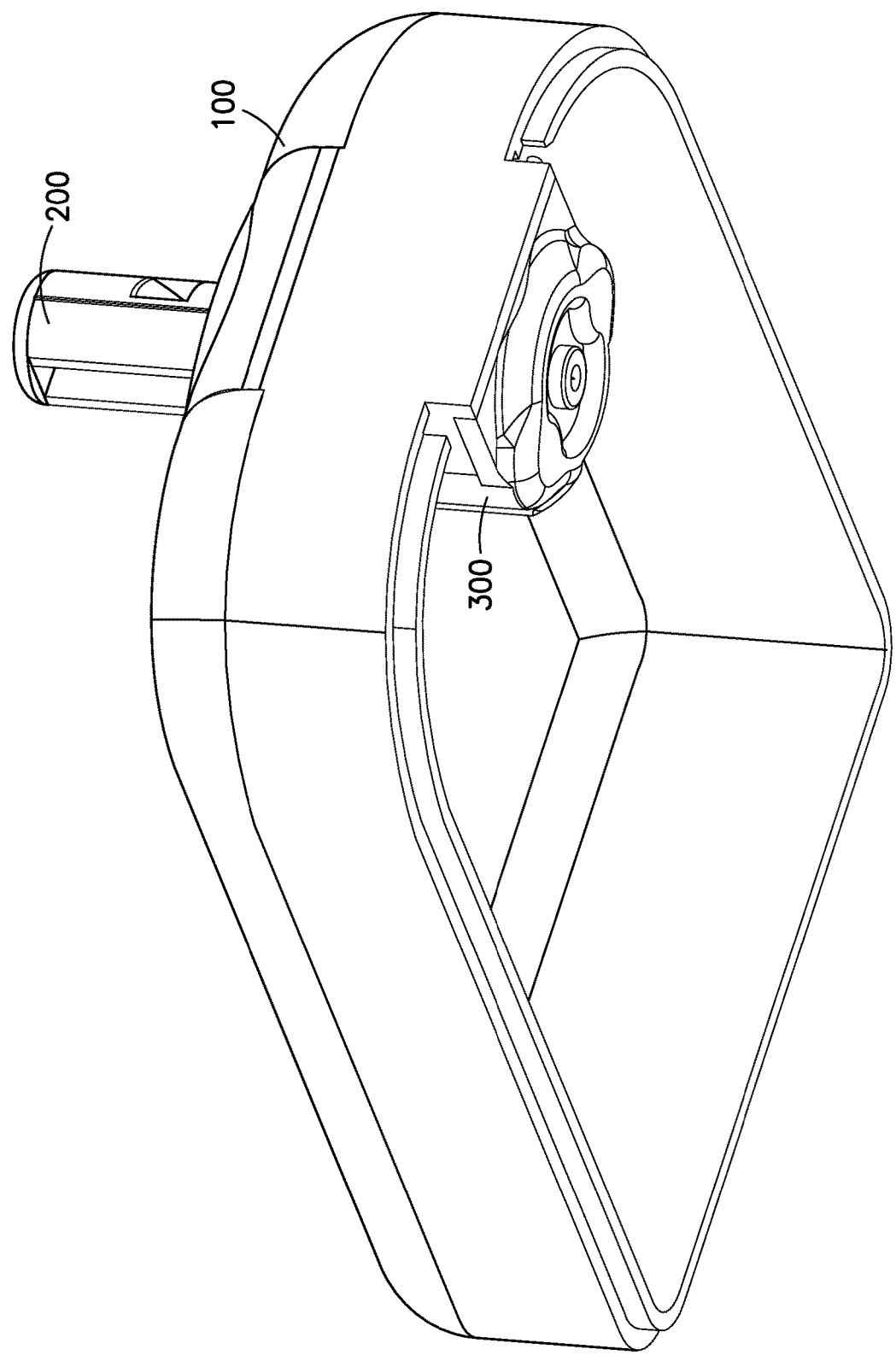
FIG. 12 is a view of the completed assembly of the insertion device of FIG. 1 wherein the base is omitted for illustration purposes in accordance with an embodiment of the present invention.

The button subassembly can then be assembled with the housing top 100 and mechanism housing 300. FIG. 10 is a view of the assembly of the button subassembly and springs into the housing of the insertion device of FIG. 1 and illustrating the use of temporary protective tubing on the catheter, and FIG. 11 is a view of the partially complete assembly of the button subassembly and springs into the housing of the insertion device of FIG. 1. FIG. 12 is a view of the completed assembly of the insertion device of FIG. 1 wherein the base is omitted for illustration purposes in accordance with an embodiment of the present invention.

Figure 13:
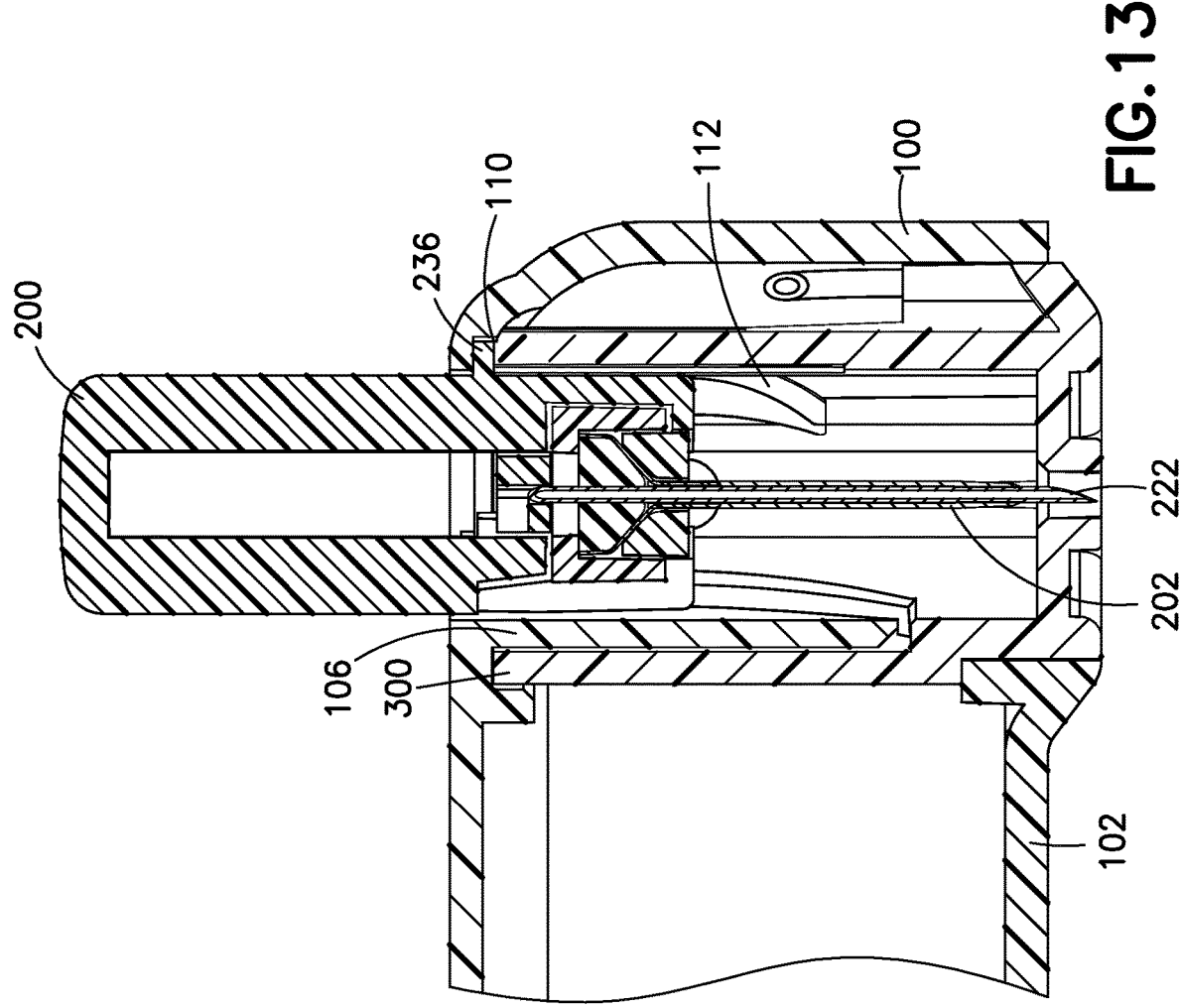
FIG. 13 is a sectional view of the insertion device of FIG. 1 in a pre-activation state in accordance with an embodiment of the present invention.

To complete assembly, the button 200 and assembly thereof is slidably assembled with a projection 106 extending from an inner surface of the top housing 100 as shown in greater detail in FIG. 13. FIG. 13 is a sectional view of the fully assembled insertion device of FIG. 1 in a pre-activation state in accordance with an embodiment of the present invention. A button lock arm 112 of the top housing 100 retains the button subassembly in place during the next assembly step which is placing the mechanism housing 300 into the top housing 100 thereby trapping the other subassemblies therein.

During the placement of the mechanism housing 300 into the top housing 100, a piece of temporary tubing 228 is placed over the catheter 202 and introducer needle 222 therein to both protect the needle tip and guide the catheter through the exit hole in the mechanism housing 300 during assembly. Retraction springs 230 are press fit onto the introducer needle hub 224 and the button subassembly is inserted through the hole 104 in the top housing 100 as shown in FIG. 11. The tubing or cannula 220 that connects to the reservoir or pump (not shown) is sealed in a receiving feature in the top housing. The springs 230 can be manufactured using stainless steel, but embodiments are not limited thereto.

The mechanism housing 300 is preferably comprised of three cylinders, guides or barrels, including a center barrel 302 that slidably receives and guides the button subassembly, and two barrels 304, one on each side of the center barrel 302 that constrain the springs 230. During assembly, the springs 230 are captured between bosses 242 of the introducer needle hub 224 and a bottom of the barrels 304 of the mechanism housing 300. In doing so, the springs 230 exert an expansion force between the introducer needle hub 224 and a bottom of the barrels 304 of the mechanism housing 300. In the exemplary embodiment, a plurality of springs 230 and adjacent barrels 304 are shown. However, in this or other embodiments of the present invention, a single spring and adjacent barrel can be provided in substantially the same manner, wherein the unused adjacent barrel can be left empty or can be omitted entirely. Still further, a single spring can be provided in the button top and extended during insertion that, upon completion, retracts to its natural state thereby retracting the introducer needle from the catheter.

The rounded, bosses 242 are provided with a diameter and length to center and align the springs 230 during operation. The springs 230 can be partially preloaded during assembly of the insertion device, and the mechanism housing 300 can be laser welded or glued to the top housing 100. The bottom or base 102 can then be added. In doing so, the full and complete insertion mechanism subassembly can be placed onto the base 102 with all of the other components, as the last assembly step. Having the completed insertion mechanism subassembly allows for easy handling in production, as opposed to trapping all of the parts between the top and bottom housings. In an exemplary production, the mechanism housing 300 would be attached to the top housing 100 using snaps or adhesive (not shown) which holds together the mechanism. In yet two other exemplary embodiments described below in regard to FIGS. 25 and 26, similar subassembly concepts are used to make assembly manageable, but the subassembly is an independent unit in one embodiment and part of the base in the other.

In each embodiment, after finally assembly, the insertion device is hermetically sealed from the remainder of the device. That is, the mechanism housing 300 into which water from a shower or swimming is free to enter through the catheter exit hole or from the button hole in the housing top, is hermetically sealed with the laser welding or gluing step, thereby protecting the remaining content of the device housing 100, such as content of the electronic/pump compartments of the device.

Figure 14:
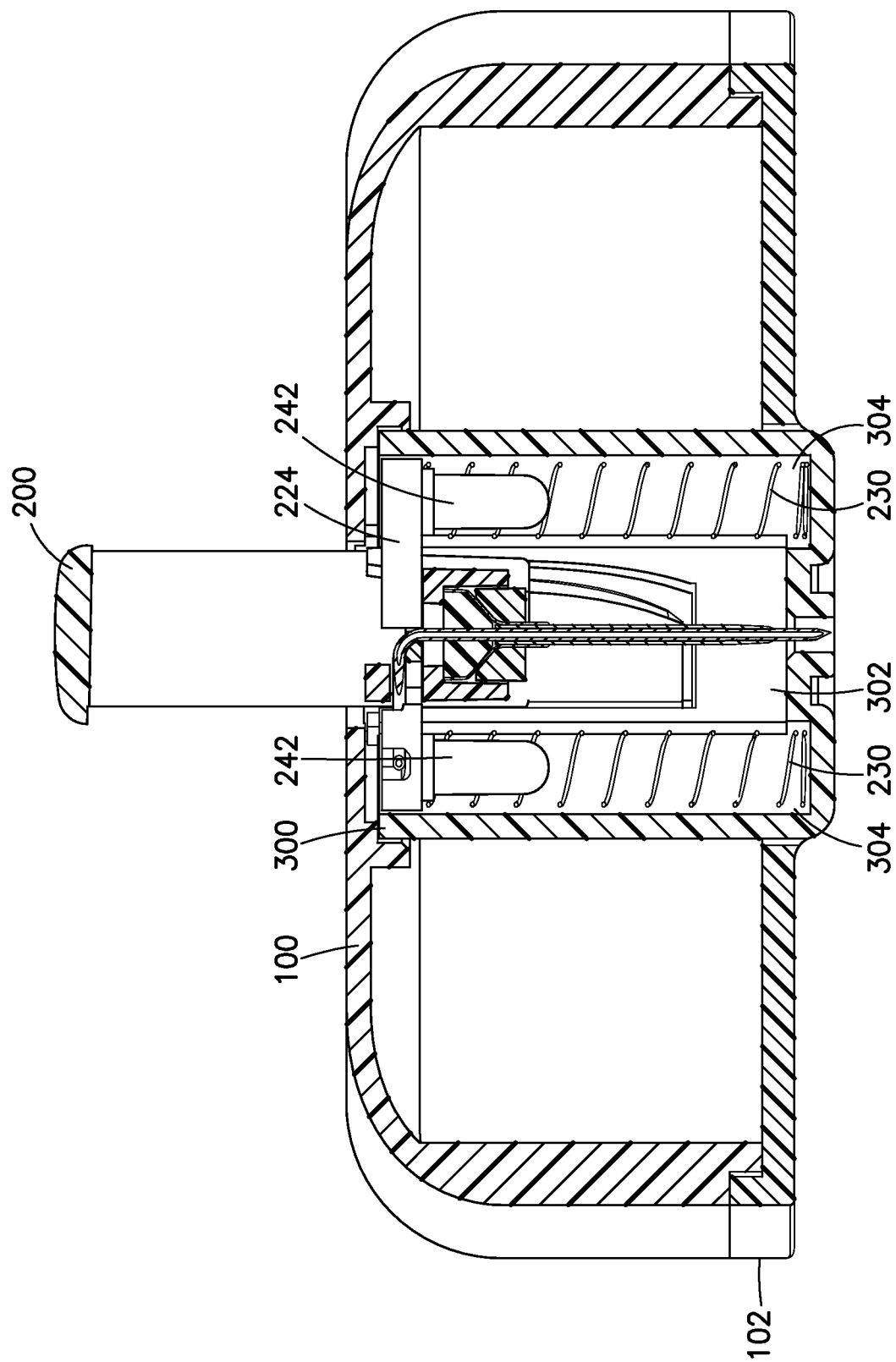
FIG. 14 is another sectional view of the insertion device of FIG. 1 in a pre-activation state in accordance with an embodiment of the present invention.

FIG. 13 is a sectional view of the fully assembled insertion device of FIG. 1 and FIG. 14 is another sectional view perpendicular to the view of FIG. 13 of the fully assembled insertion device of FIG. 1 in a pre-activation state in accordance with an embodiment of the present invention. As shown in FIG. 13, one or more breakable ribs 236 on the activation button 200 are captured by step detents 110 in the top housing 100 to hold the button 200 in the pre-activation position. A safety tab (not shown) could also be positioned in the button slot which would prevent accidental activation during shipping and handling of the device once it is removed from the packaging. The safety tab would be removed just prior to insertion.

To activate the device, the user pushes the button 200 into the top housing 100. Once the ribs 236 break or deformation force threshold is exceeded, the three ribs 236 yield and the button 200 abruptly moves downward inserting the introducer needle 222 and catheter 202, and loading the retraction springs 230. The springs 230 can be partially preloaded during assembly of the insertion device. The minimum break force of the breakable ribs 236 ensures that the user pushes hard enough to fully insert the catheter. Partial activation would result in the catheter not fully inserting, the introducer needle not retracting and the catheter not locking in the post activation position.

The release of the button 200 from the ribs 236 is configured to occur once a desired amount of activation force has been applied to the button 200. Since the button 200 is releasably held in the up and extended position by the engagement between the ribs 236 and the step detents 110, the force applied to the button 200 by the user steadily increases for some period of time prior to release. Upon sudden release, the force upon the button 200 has reached a desired value and therefore, the button 200 is accelerated downward due to the sudden freedom to travel and the desired force applied to the button at the time of release and maintained thereafter. Such release ensures that a desired amount of downward force, speed, smoothness and angle has been applied by the user. Such activation substantially eliminates variations in the user force applied, speed, smoothness and angle thereof, and reduces insertion failure and/or discomfort to the user.

Figure 15:
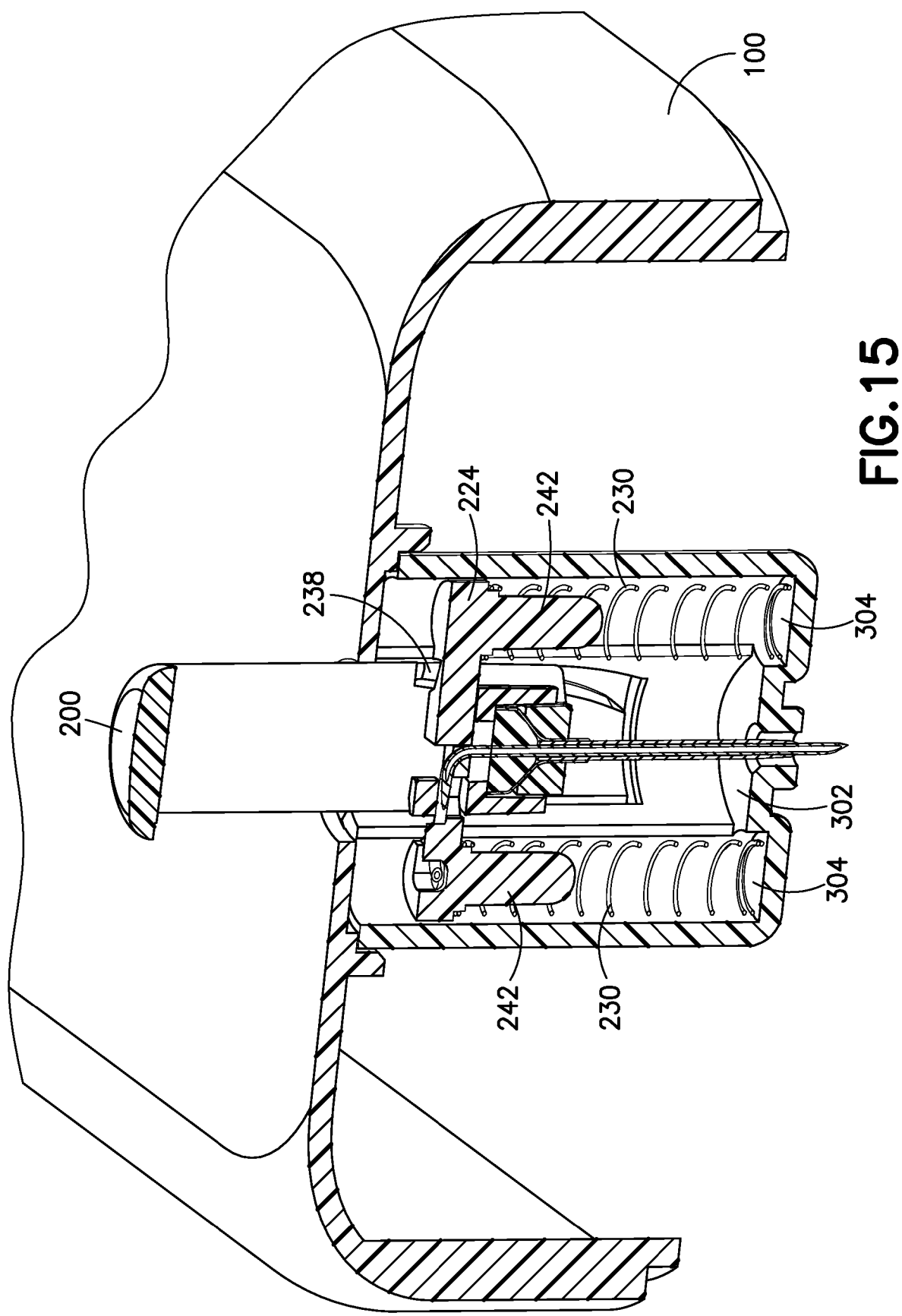
FIG. 15 is a sectional view of the insertion device of FIG. 1 in an intermediate activation state in accordance with an embodiment of the present invention.
Figure 16:
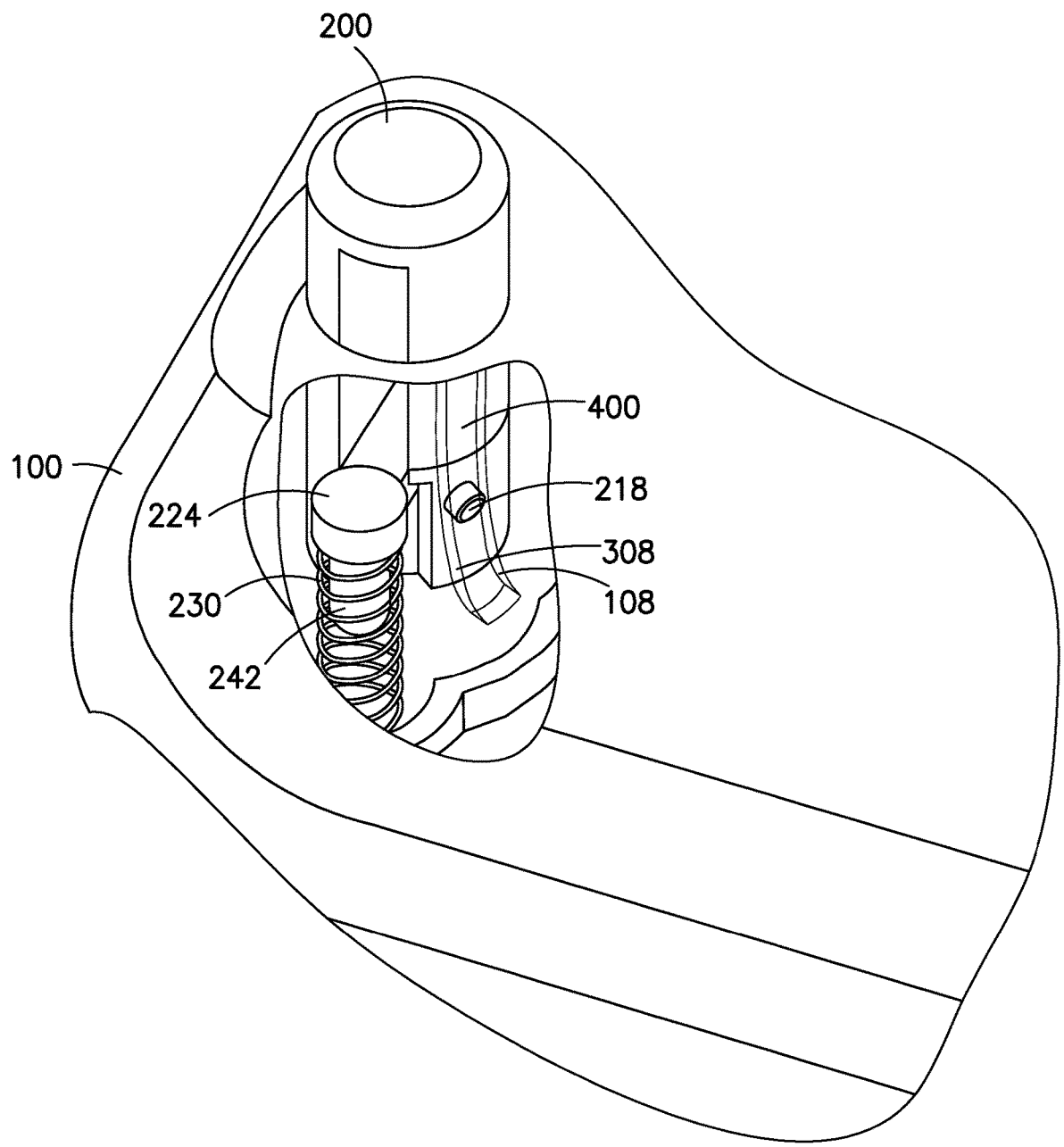
FIG. 16 is a transparent view of the insertion device of FIG. 1 in the intermediate activation state illustrating a position of a radial operation pin within a helical pathway in accordance with an embodiment of the present invention.

After the release of the button 200, the button subassembly and components therein begin to travel through the mechanism housing 300. FIG. 15 shows a view of the insertion device at the beginning of such insertion. FIG. 15 is a sectional view of the fully assembled insertion device of FIG. 1 in an intermediate activation state in accordance with an embodiment of the present invention.

FIG. 15 also illustrates one of the two teeth 238 on the release collar 208 that couples the introducer needle hub 224 and catheter/septum subassemblies. In this position the teeth 238 are locked over the top the introducer needle hub 224 so as the button 200 is pressed down, the introducer needle hub 224 moves down as well. As the button 200 is pressed down, the introducer needle hub 224 moves down as well, which results in the introducer needle 222 and catheter 202 being simultaneously inserted into a user skin surface (not shown), and also results in the introducer needle hub 224 compressing the springs 230. In order to create an insertion device with a small foot print, each of the springs 230 has a small diameter relative to the compression length which, if unsupported, would cause the springs to buckle during compression. The bosses 242 on the introducer needle hub 224 translate through the middle of the springs 230 during compression to prevent the springs 230 from buckling. In the exemplary embodiment, the springs 230 are compressed, and exert an expansion force to retract the introducer needle hub and introducer needle. However, in this or other embodiments of the present invention, one or more extension springs can be used, and exert a retraction force to retract the introducer needle hub and introducer needle.

Figure 17:
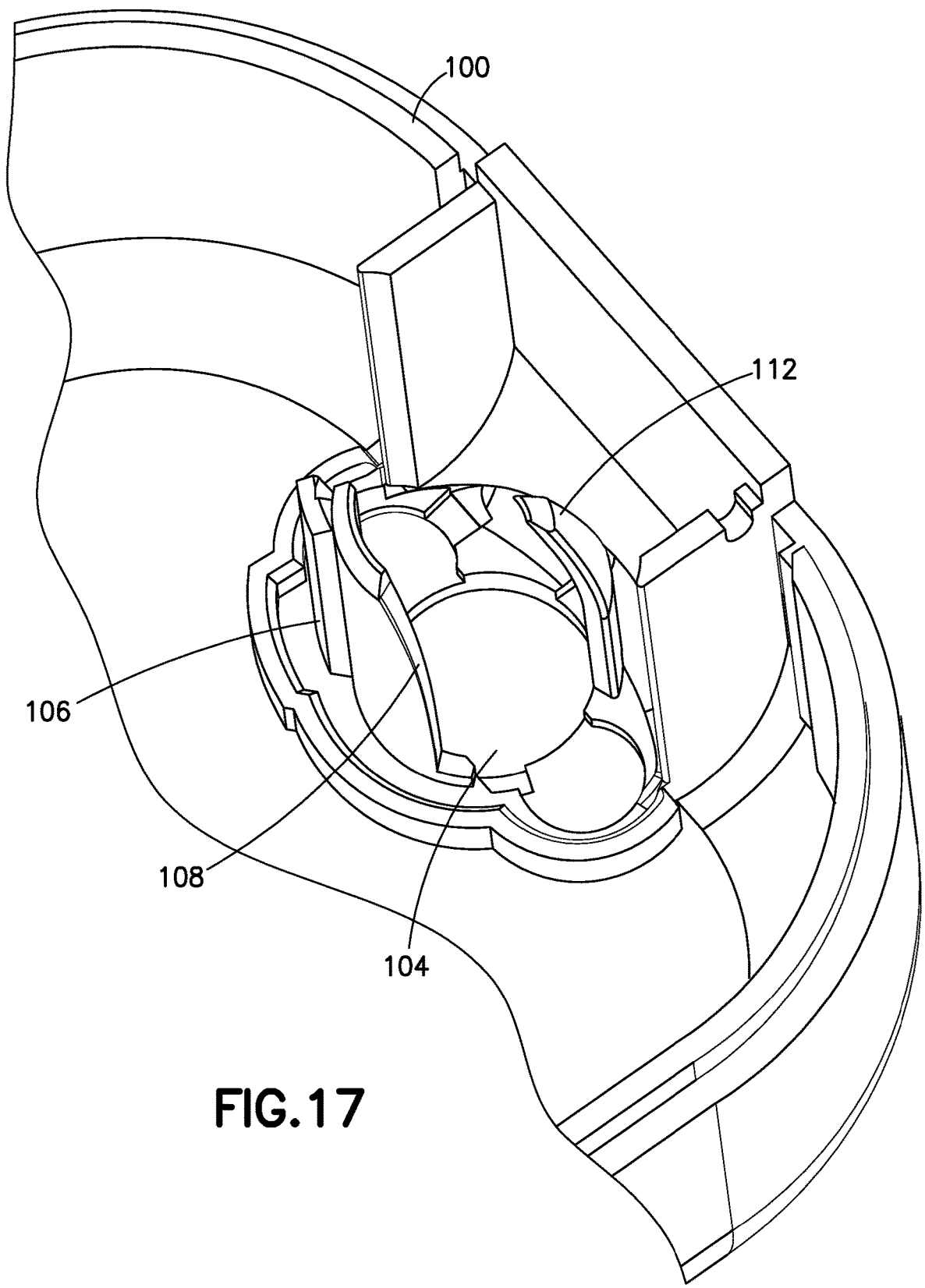
FIG. 17 is a bottom view of the top housing of the insertion device of FIG. 1 illustrating a mating portion of the helical pathway surface for the radial operation pin of FIG. 16 in accordance with an embodiment of the present invention.
Figure 18:
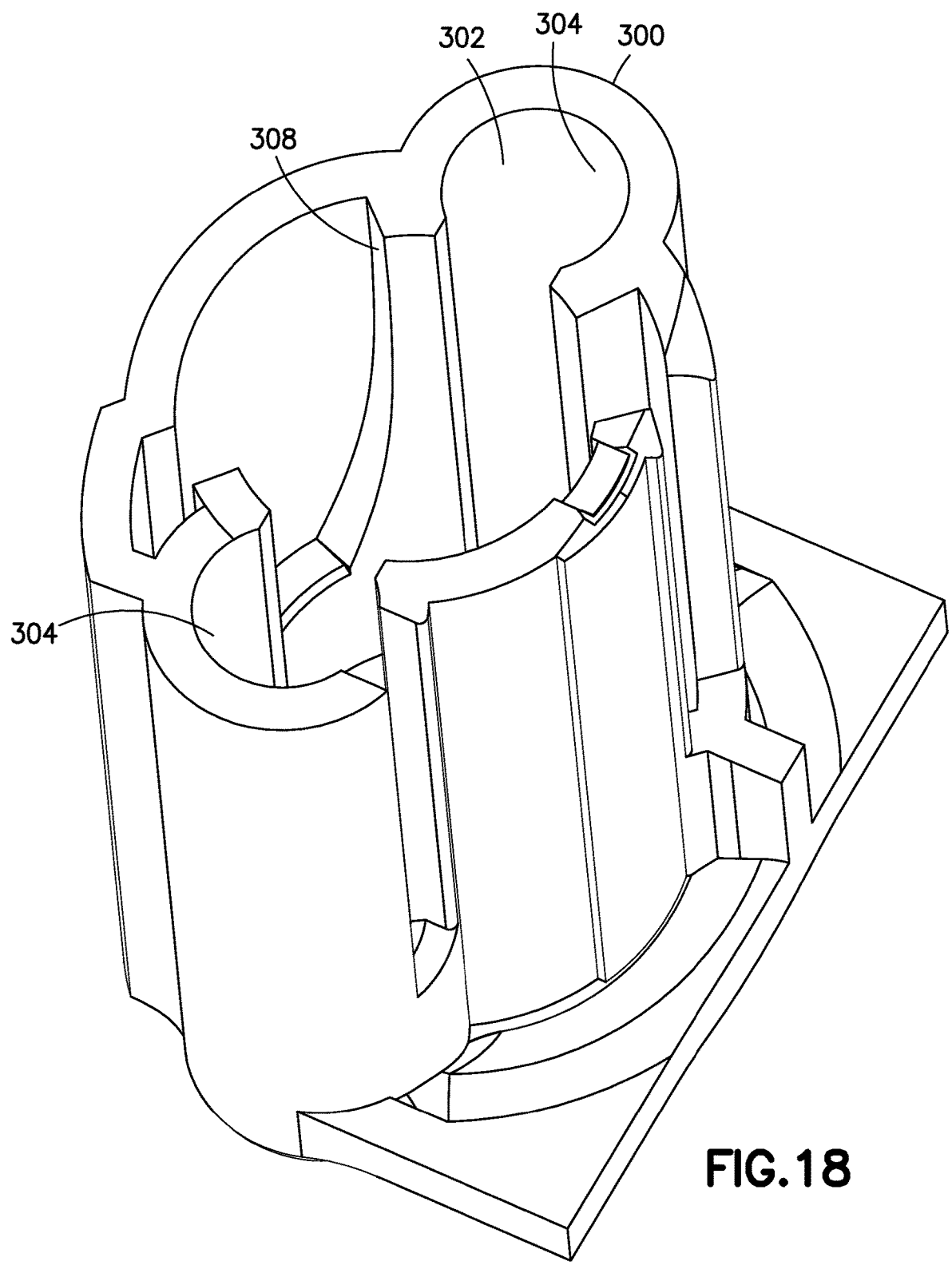
FIG. 18 is a view of the mechanism housing of the insertion device of FIG. 1 illustrating a mating portion of the helical pathway surface for the radial operation pin of FIG. 16 in accordance with an embodiment of the present invention.

As noted above, the catheter/septum subassembly of FIG. 5 is attached to the button 200 and introducer needle hub 224 but is free to rotate up to 20 degrees around the primary axis. In this case, the primary axis is defined as the axis extending along the geometric center of the insertion needle 222. Slots 216 are provided in the button 200 to allow linear travel of the introducer needle hub 224 relative to the button 200, but prohibit rotational movement of the introducer needle hub relative to the button 200. The slots 216 in the button 200 also allow rotational movement of the radial operation pin 218 of the release collar 208 relative to the button 200. The angle of this rotation is controlled by the radial operation pin 218 extending from the release collar 208. During insertion, that is, downward travel of the button subassembly, the radial operation pin 218 travels in a helical pathway 400 created by the combined features in the top housing 100 and mechanism housing 300. During such travel, the radial operation pin 218 of the release collar 208 rotates the release collar 208 to eventually release the introducer needle subassembly from the catheter/septum subassembly. The surfaces 108 in the top housing 100, and 308 in the mechanism housing 300 that create the helical pathway 400 are divided between two parts, so that both parts can be molded without slides. That is, by creating the helical pathway 400 using the coupling of two separately molded parts, a single part having the slide or pathway molded therein is not required, significantly simplifying the manufacture of the insertion device. FIGS. 17 and 18 show the surface 108 in the top housing 100, and 308 in the mechanism housing 300 that create the helical pathway 400 when assembled.

FIG. 17 is an bottom view of the top housing 100 of the insertion device of FIG. 1 illustrating a portion of the pathway surface, and FIG. 18 is a view of the mechanism housing 300 of the insertion device of FIG. 1 illustrating the remaining portion of the pathway surface of the radial operation pin 218 in accordance with an embodiment of the present invention. As shown in FIG. 17, the projection 106 of the top housing 100, into which the button subassembly is slidably disposed, includes an edge that can be provided with a similar curved, contoured, or otherwise configured shape 108 that, upon assembly with the mechanism housing 300, forms one half, side or portion of the helical pathway 400. As shown in FIG. 18, an inner diameter or chamber surface of the mechanism housing 300, into which the button subassembly is slidably disposed, can be provided with a curved, contoured, or otherwise configured shape 308 that, upon assembly with the top housing 100, also forms one half, side or portion of the helical pathway 400. When the top housing 100 and mechanism housing 300 are assembled, the elements 108 and 308 form the helical pathway 400. The pathway is helical to induce a rotational movement of the release collar 208 relative to the button 200 by guiding the radial operation pin 218 therein, as the button 200 and release collar 208 travel in a linear direction.

As noted above, the slots 216 provided in the button 200 allow movement of the radial operation pin 218 of the release collar 208. Further, the catheter/septum subassembly of FIG. 5 is attached to the button 200 and introducer needle hub 224, but is free to rotate up to 20 degrees around the primary axis. Such 20 degrees of rotation permits the travel of the radial operation pin 218 of the release collar 208 in the helical pathway 400. As the button 200 is pressed down, the release collar 208 and radial operation pin 218 of the release collar 208 move down as well through the stationary top housing 100 and mechanism housing 300. The radial operation pin 218 of the release collar 208 therefore, slidably disposed in the helical pathway 400, rotates the release collar when moved down through the stationary top housing 100 and mechanism housing 300 by the button 200.

In the pre-activation state, the radial operation pin 218 angle is constrained to an orientation in which the teeth 238 of the release collar 208 are fully engaged with the introducer needle hub 224. During button 200 movement between the pre-activation state and the post-activation state, the radial operation pin 218 of the release collar 208 rotates the release collar 208 when moved through helical pathway 400 of the stationary top housing 100 and mechanism housing 300.

In the post-activation state, the radial operation pin 218 has been rotated up to 20 degrees, which decouples the introducer needle hub 224 from the teeth 238 of the release collar 208, freeing the introducer needle hub 224 from the release collar 208, to be retracted by the compressed springs 230. The release collar 208 and other elements of the catheter/septum subassembly are left in the down and inserted position.

Figure 19:
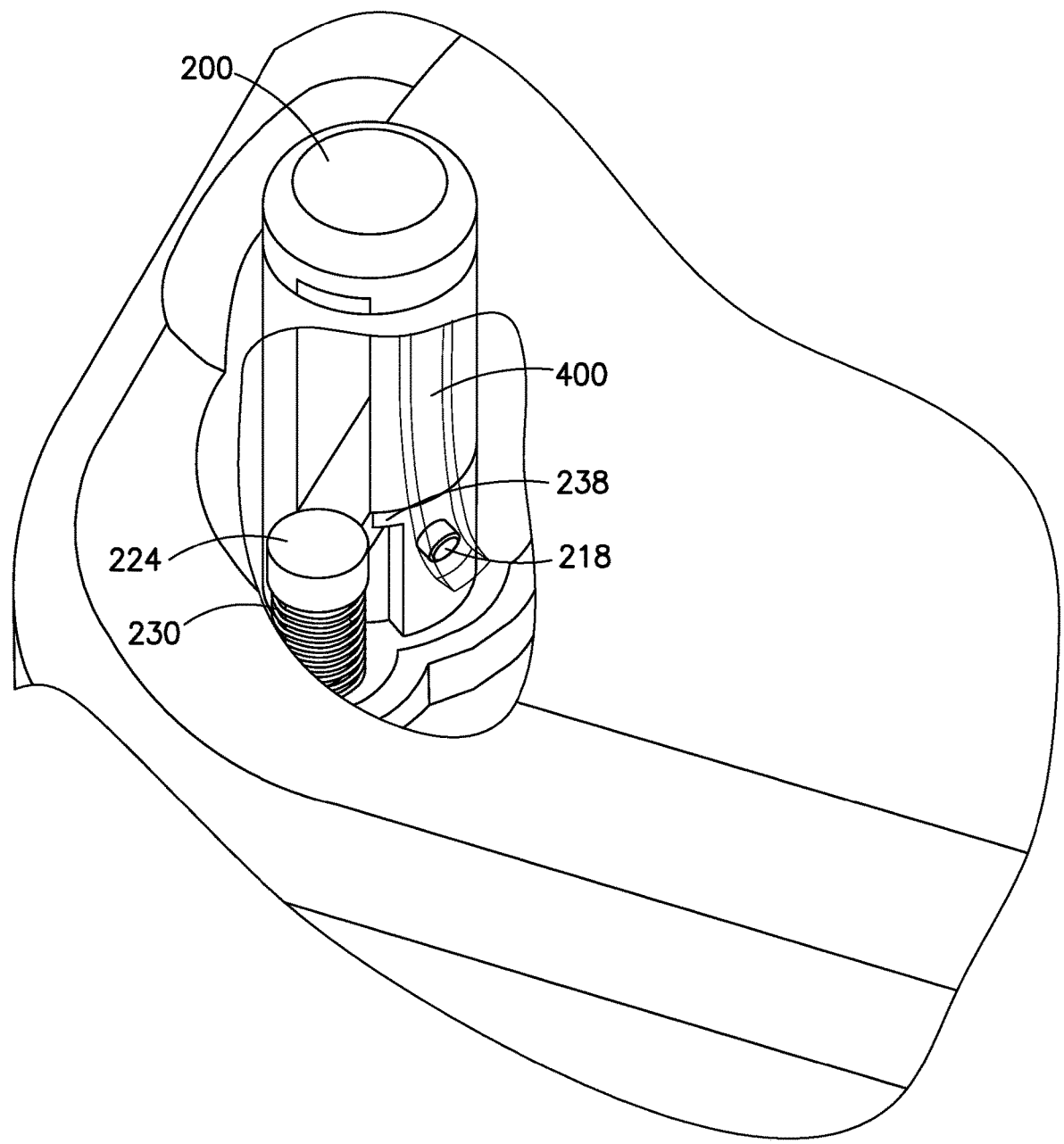
FIG. 19 is a transparent view of the insertion device of FIG. 1 in an intermediate activation state illustrating a position of the radial operation pin in accordance with an embodiment of the present invention.
Figure 22:
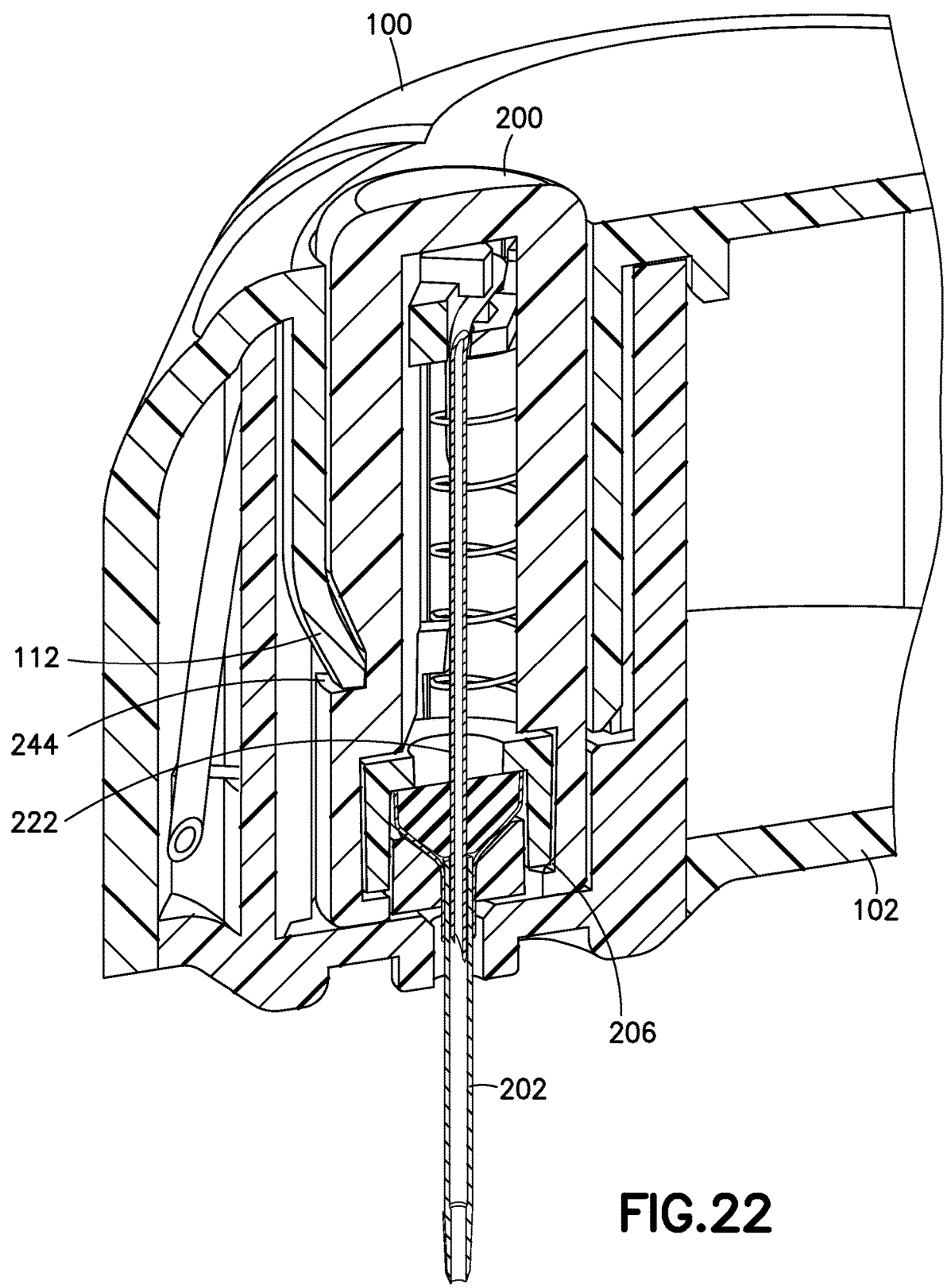
FIG. 22 is a sectional view of the insertion device of FIG. 1 illustrating a lock arm of the top housing in a post-activation state in accordance with an embodiment of the present invention.

FIG. 19 shows the insertion device during insertion of the introducer needle 222 and catheter 202 and at a point just before the introducer needle hub 224 is released by the radial operation pin 218 of the release collar 208 for retraction. The radial operation pin 218 and the release collar 208 is almost fully rotated by engagement with the helical pathway 400 and where, at the end of rotation by the helical pathway 400, the teeth 238 on the release collar 208 are about to move free of the detents 240 of the introducer needle hub 224 and release the introducer needle hub 224 so it can be pushed up and retracted by the springs 230. That is, as the radial operation pin 218 and the release collar 208 are rotated by engagement with the helical pathway 400, the teeth 238 on the release collar 208 simultaneous rotate until free of the detents 240 of the introducer needle hub 224. At this point, the release collar 208 being held down by the button 200, is no longer secured to the introducer needle hub 224, and the springs 230 force the introducer needle hub 224 and introducer needle 222 upward and into the retracted position, leaving the catheter/septum subassembly in the down and inserted position. The button 200 is locked in the down position, thereby holding the catheter/septum subassembly in the down and inserted position. The lock arm 112 that protrudes from the top housing 100 that retains the button subassembly in place during assembly can also be configured to snap into a detent 244 in the button 200 in the post-activation state locking the button subassembly in place keeping the catheter in the skin as shown in FIG. 22.

Figure 20:
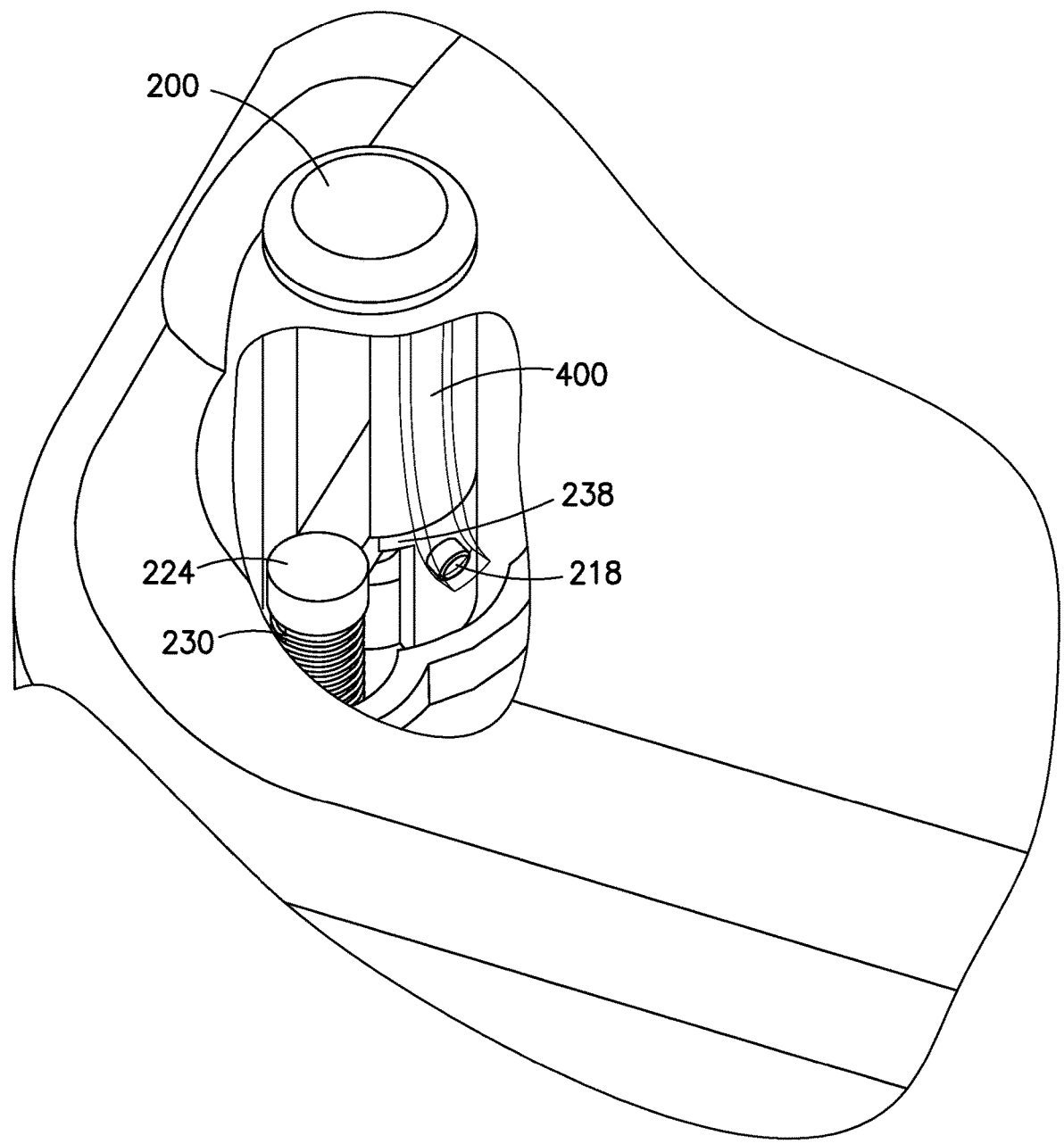
FIG. 20 is a transparent view of the insertion device of FIG. 1 at an activation state illustrating a position of the radial operation pin at full insertion in accordance with an embodiment of the present invention.
Figure 21:
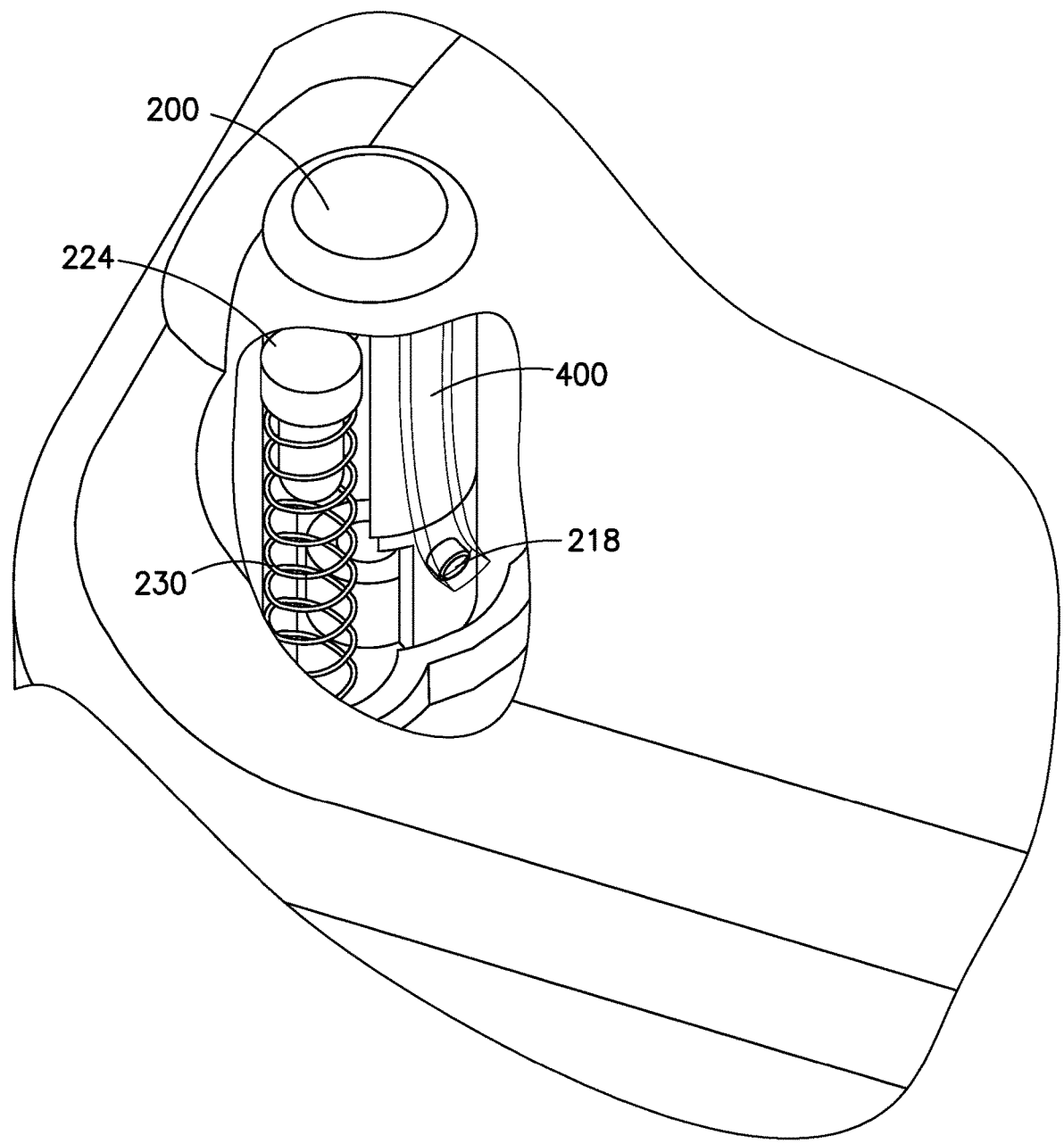
FIG. 21 is a transparent view of the insertion device of FIG. 1 at the post-activation state illustrating a position of the radial operation pin at full retraction in accordance with an embodiment of the present invention.
Figure 23:
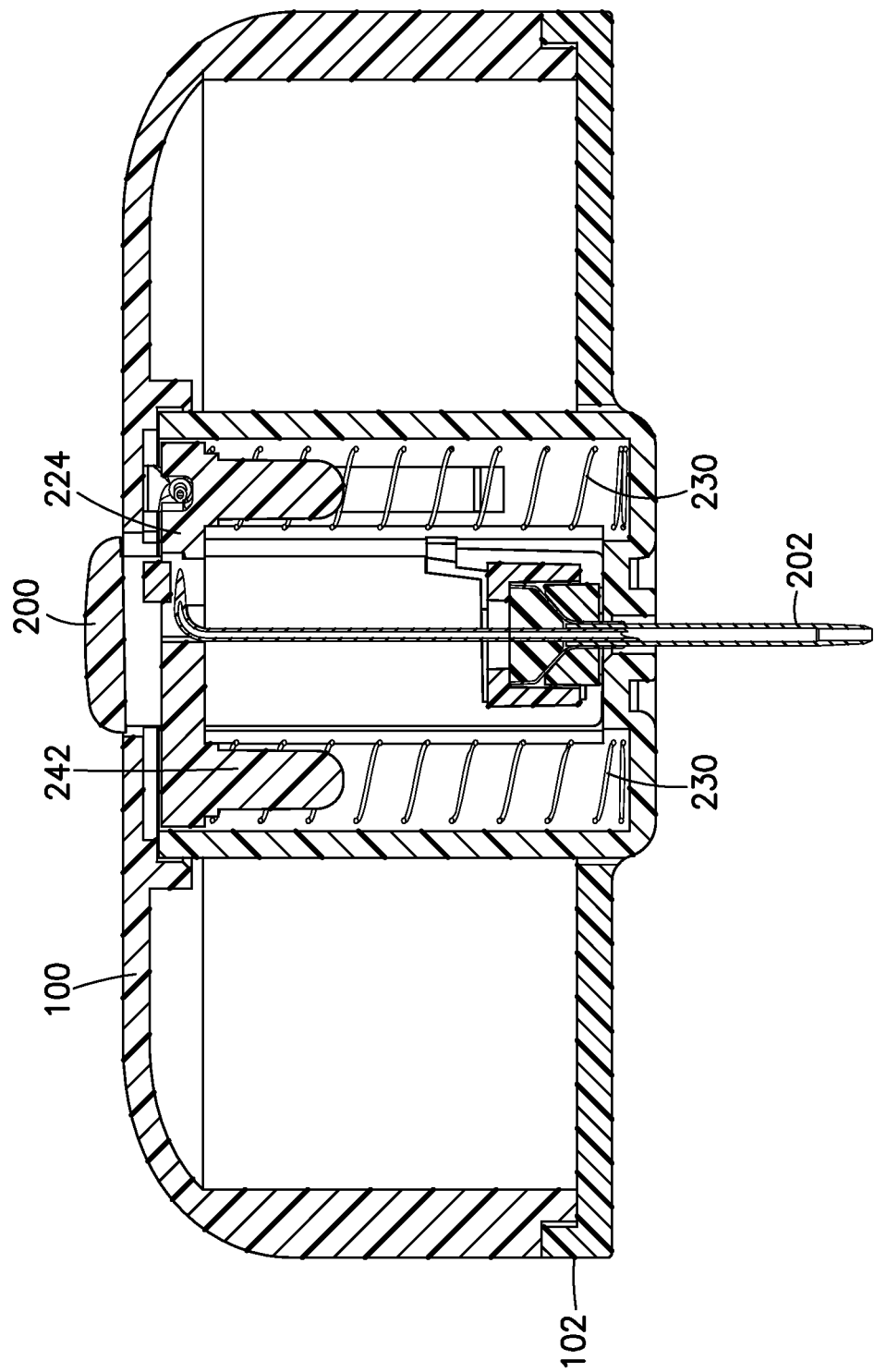
FIG. 23 is a sectional view of the insertion device of FIG. 1 in a post-activation state in accordance with an embodiment of the present invention.
Figure 24:
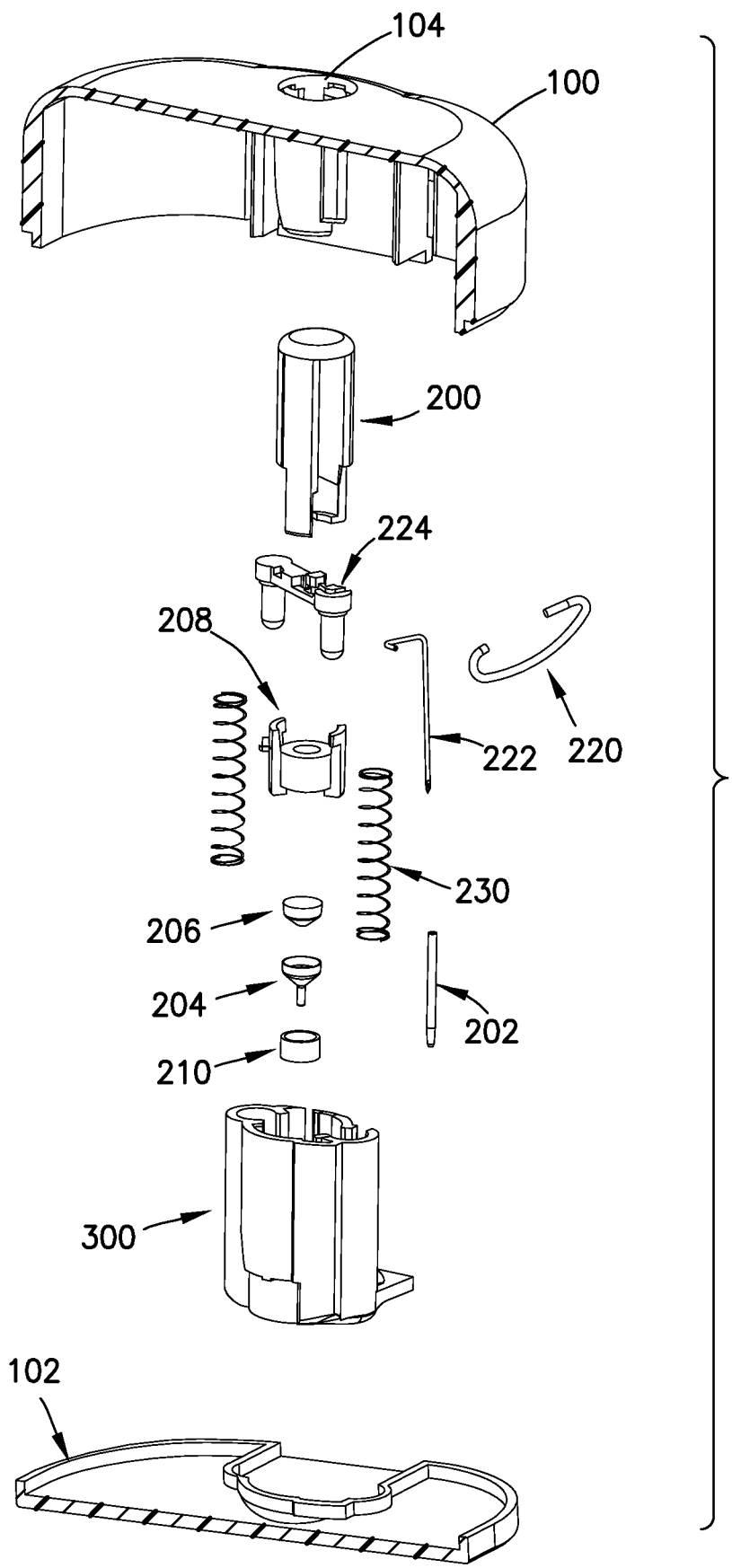
FIG. 24 is another exploded view of the insertion device of FIG. 1 in accordance with an embodiment of the present invention.

FIG. 20 shows the insertion device just at full insertion of the introducer needle 222 and catheter 202. The retraction springs 230 are fully compressed and the radial operation pin 218 and release collar 208 have been rotated to an extent required for decoupling the teeth 238 of the release collar 208 from the introducer needle hub 224 to release the introducer needle hub 224 for retraction as shown in FIGS. 21 and 23. FIGS. 21 and 23 show the insertion device in a post-activation state. At this point, the release collar 208 being held down by the button 200, is no longer secured to the introducer needle hub 224, and the springs 230 force the introducer needle hub 224 and introducer needle 222 upward and into the retracted position, leaving the catheter/septum subassembly in the down and inserted position.

The introducer needle 222 retracts farther into the housing than its pre-activation state position to ensure needle stick shielding and to protect the catheter from damage. The tip of the introducer needle 222 remains sealed by the septum 206 in the fluid path to form an uninterrupted fluid path with the catheter 202. In this or other embodiments, the tip or distal portion of the introducer needle 222 remains within the catheter 202 and sealed by the septum 206 to form an uninterrupted fluid path with the catheter 202.

In the exemplary embodiments, manual insertion of the introducer needle and catheter allows the insertion device to be smaller, simpler and cheaper than insertion devices employing spring assisted insertion. Other patch pump plastic catheter insertion mechanisms use insertion springs which are large relative to the retraction spring because the insertion force is large relative to the retraction force. Fully integrated, spring assisted insertion also requires angled insertion for a low profile device which increases the stroke and greatly increases the wound and mechanism size. The insertion spring serves no purpose after insertion, but simply takes up room in the device wherein size is one of the most important user requirements for the product.

In the exemplary embodiments, the dual retraction spring configuration also allows for a very small size. One barrel of the insertion device housing guides the button and catheter, and the adjacent barrels house the two retraction springs. Having the springs in separate barrels and directed by bosses on the introducer needle hub allows for much smaller springs than a single barrel configuration in which the spring is coaxial with the catheter. A single coaxial spring creates access to the button assembly since spring design limitations require the spring to extend nearly from the bottom of the housing to the top. Access is required for features like the locking arm and if the features are implemented inside the spring, the entire mechanism must grow to accommodate them increasing the mechanism foot print. Passively locking the catheter down and retracting the introducer needle creates the simplest possible manual insertion user interface for a manual insertion mechanism which is a single button push.

As noted, the retraction springs 230 are minimally loaded before use to ensure that the introducer needle 222 retracts into the device completely. The springs 230 load further during insertion. Providing minimally loaded springs and not fully loaded springs in the insertion device, reduces the risk associated with sterilizing and storing loaded springs and simplifies the design.

To operate the insertion device, the user applies the insertion device to a skin surface using an adhesive upon the base 102 of the device. The user then manually pushes the protruding button 200 until breaking or deforming the ribs 236. The button 200, now suddenly free to travel, is rapidly pushed into the top housing 100 and serves to push and insert the plastic catheter 202 and introducer needle 222 into a user skin surface. As the button 200 is being pushed, the release collar 208 is rotated by the radial operation pin 218 of the release collar 208 moving through helical pathway 400. The release collar 208 is rotated to an extent required for decoupling the release collar 208 from the introducer needle hub 224, and the introducer needle hub 224 and introducer needle 222 are then retracted to a retracted position, exceeding that of the original needle position to ensure needle shielding. The plastic catheter 202 now uncoupled from the introducer needle 222 is left in the down and inserted position. The button 200 automatically locks in the down position, flush with the top of the housing, which also locks the catheter at the desired depth in the subcutaneous layer. A sensor (not shown) can be provided to sense the post-activation state and advise other electronics (not shown) that the catheter has been inserted properly which allows the patient to infuse medicament. A pump or reservoir then infuses medicament through the introducer needle, into the catheter and out into the patient's subcutaneous layer.

Figure 48:
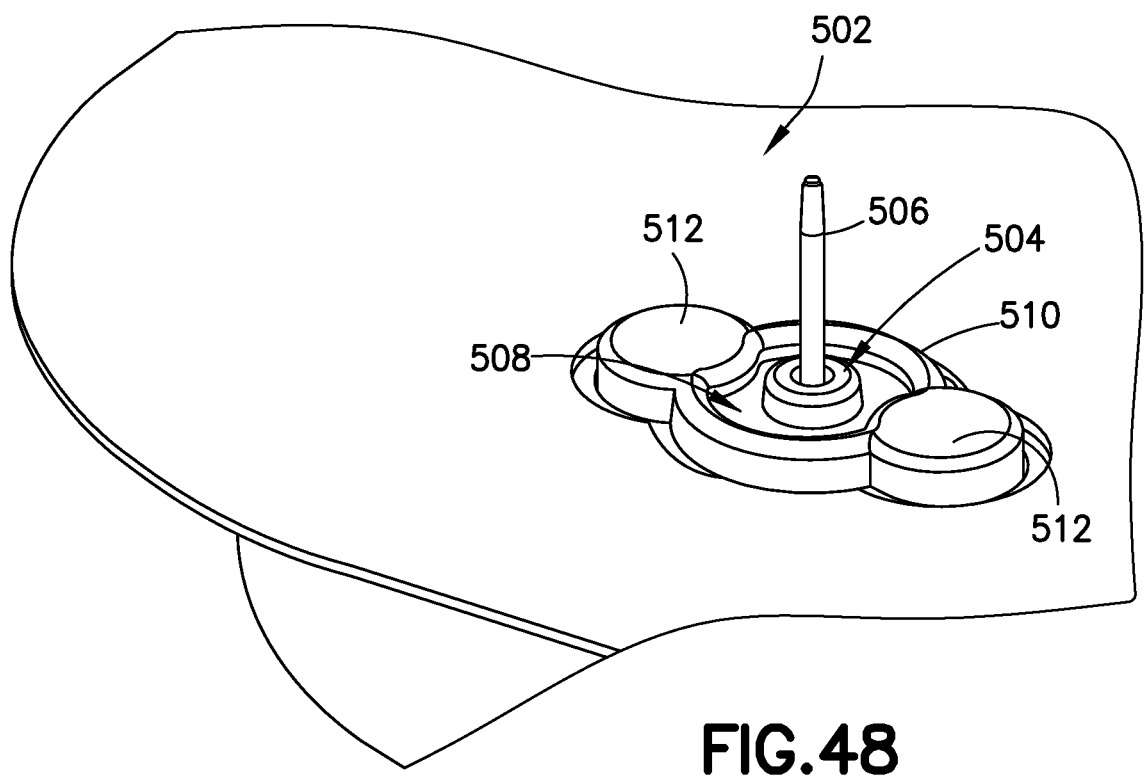
FIG. 48 is a bottom view of the insertion device of FIG. 1, showing a skin-contacting surface in accordance with an embodiment of the present invention.
Figure 49:
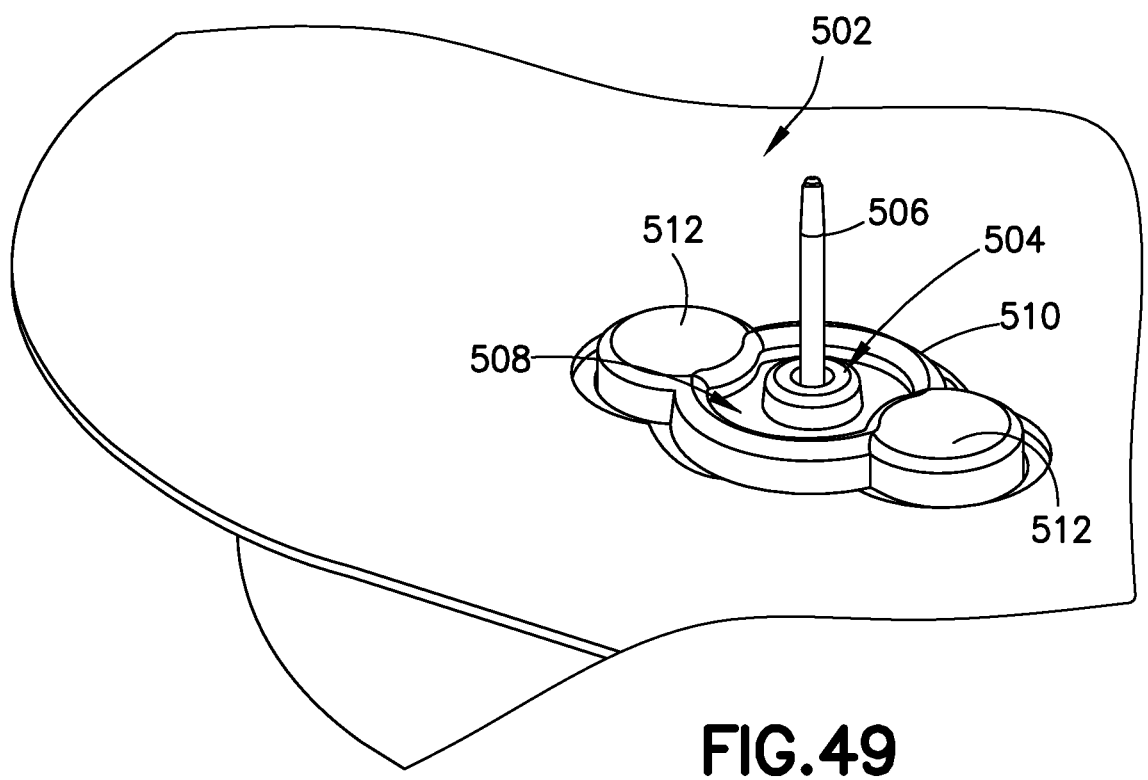
FIG. 49 is another bottom view of the insertion device of FIG. 1, showing the skin-contacting surface in accordance with an embodiment of the present invention.
Figure 50:
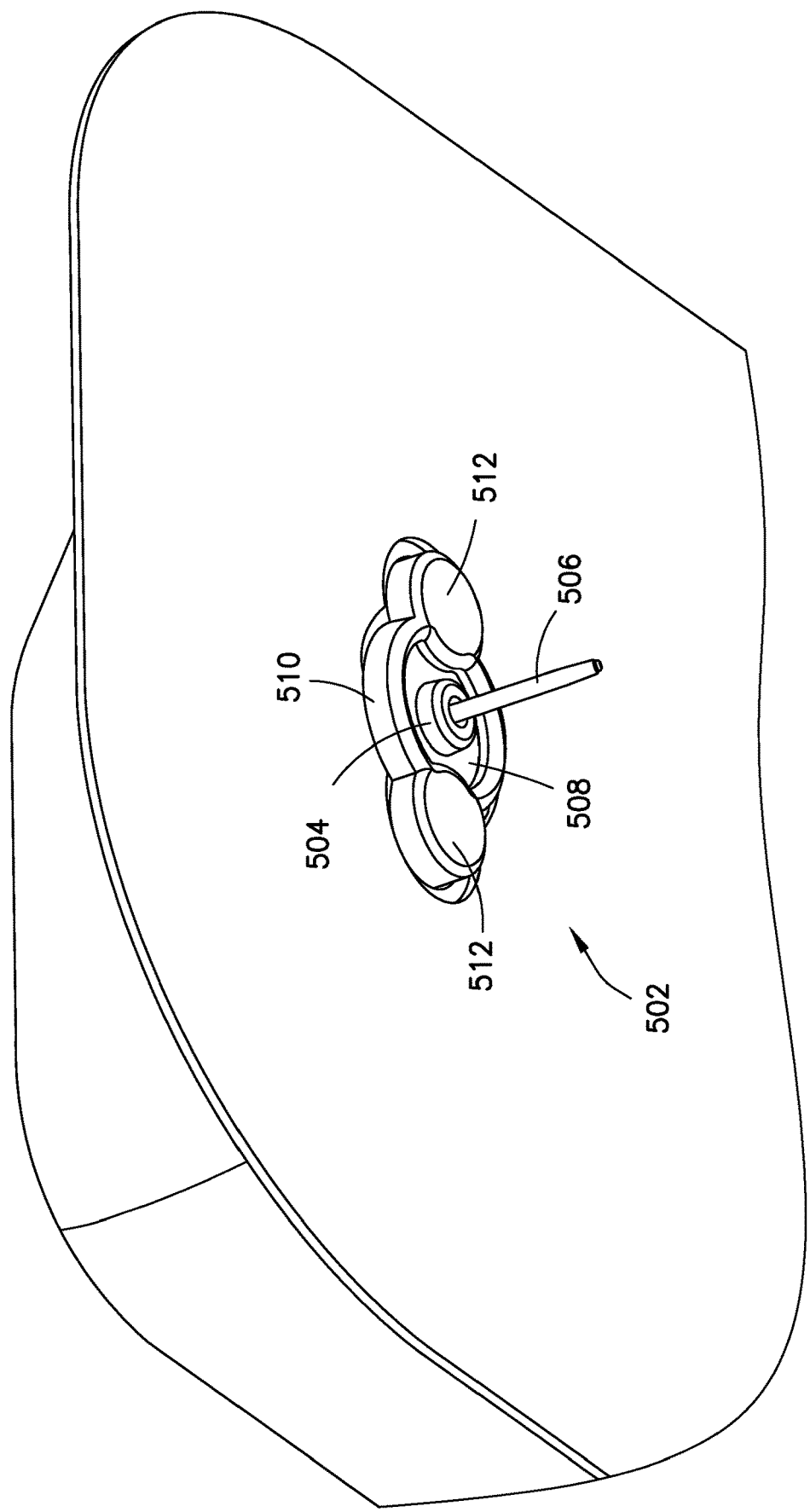
FIG. 50 is another bottom view of the insertion device of FIG. 1, showing the skin-contacting surface in accordance with an embodiment of the present invention.

To best target the desired depth, the base can include skin interface geometry to achieve and maintain a desired insertion depth, avoid skin surface tenting, and/or tension the skin surface at the insertion site. FIGS. 48-50 show examples of such skin interface geometry with a catheter deployed. In the perspective view of the device 502, a post 504 from which the catheter 506 extends during placement, protrudes into the skin surface (not shown) which helps prevent shallow catheter tip insertion in cases where the skin tented. The post 504 can extend from the base surface of the device 502 to any desired length, and can be rounded and/or chamfered at the distal end contacting the skin surface.

A well 508 can be provided surrounding the post 504. The well 508 provides space for the skin that is displaced during insertion and helps the post 504 protrude into the skin surface. A wall 510 surrounds and defines the well 508, and can extend from the base surface of the device 502 to any desired length and can be rounded and/or chamfered at the distal end contacting the skin surface. The round opposing cylinders 512 in FIGS. 48-50 can be provided, or excluded from the geometry as desired.

In the above exemplary embodiment, the insertion mechanism can be created as a subassembly in the top housing 100. This allows the insertion mechanism to be handled easily during production so the other sub systems can be assembled. Alternatively, the insertion mechanism can be created as a subassembly separate from the top housing 100 or base 102 as shown in FIG. 25, or as a subassembly in the base 102 as shown in FIG. 26.

Figure 25:
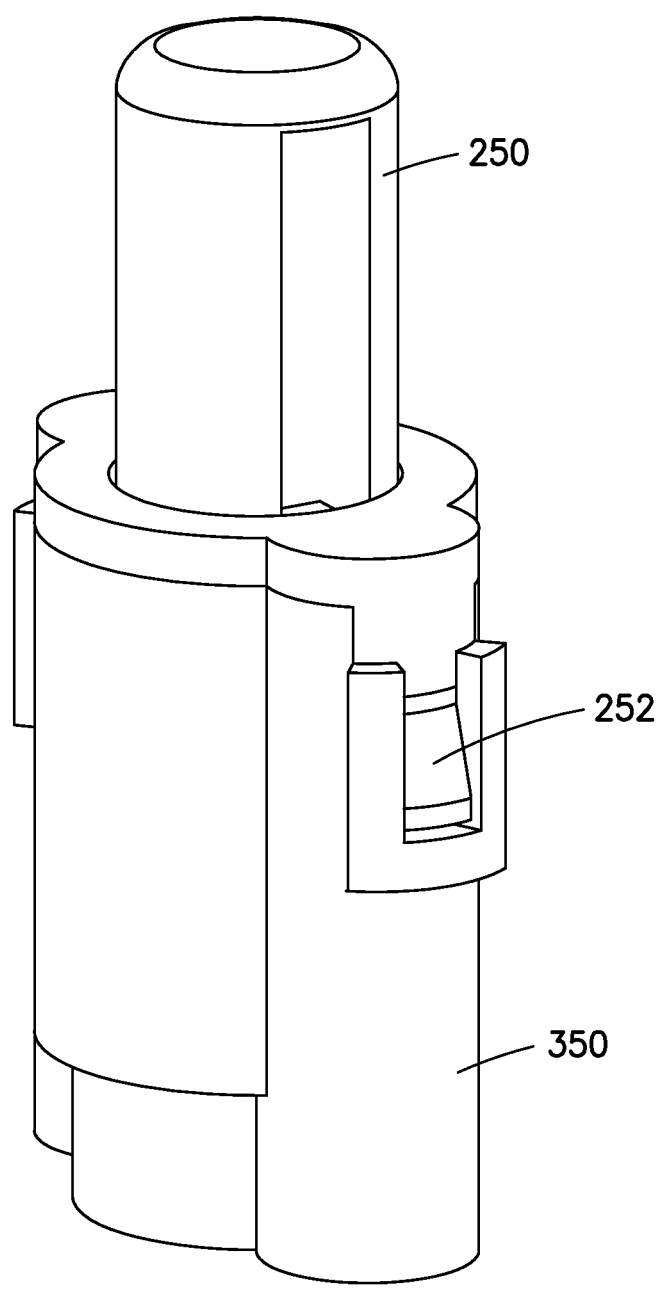
FIG. 25 is a view of another embodiment of the insertion mechanism created as a subassembly separate from the top housing or base in accordance with an embodiment of the present invention.

In FIG. 25, a completed button subassembly 250, substantially the same as described in regard to FIG. 9, is secured within a mechanism housing 350, substantially the same as described in regard to FIG. 4, using, for example, snaps or detents 252. In this case, the insertion mechanism is created as a subassembly separate from the top housing 100 or base 102. Upon completion, the insertion mechanism of FIG. 25 can then be assembled with one or more of the top housing 100 and base 102.

Figure 26:
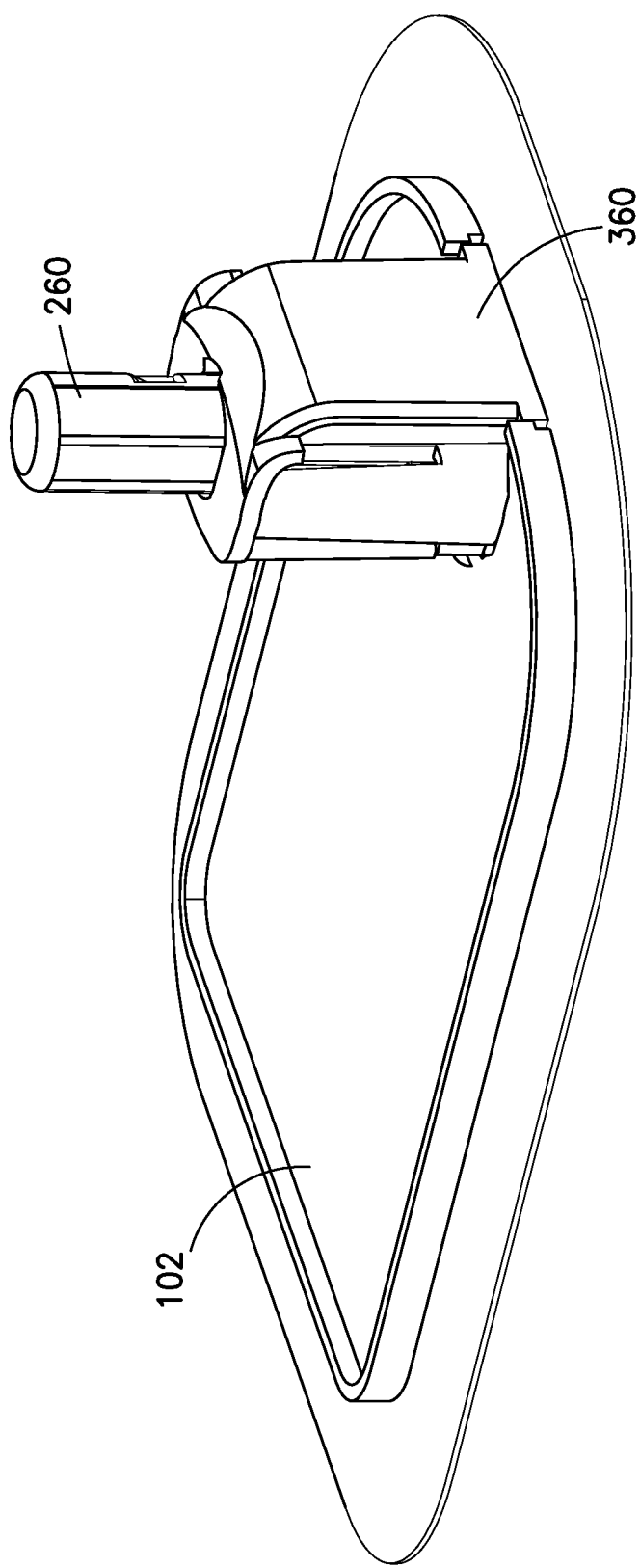
FIG. 26 is a view of another embodiment of the insertion mechanism created as a subassembly in the base in accordance with an embodiment of the present invention.

In FIG. 26, a completed button subassembly 260, substantially the same as described in regard to FIG. 9, is secured within a mechanism housing 360, substantially the same as described in regard to FIG. 4. In this case, the insertion mechanism is created as a subassembly in the base 102. Further, in each embodiment of FIGS. 25 and 26, the surfaces that create the helical pathway as described above in regard to FIGS. 17 and 18, can be provided in the button subassembly 250 and mechanism housing 350, and in the button subassembly 260, mechanism housing 360 and/or base 102, such that the surfaces can again be divided between two parts, so that both parts can be molded without slides.

Figure 27:
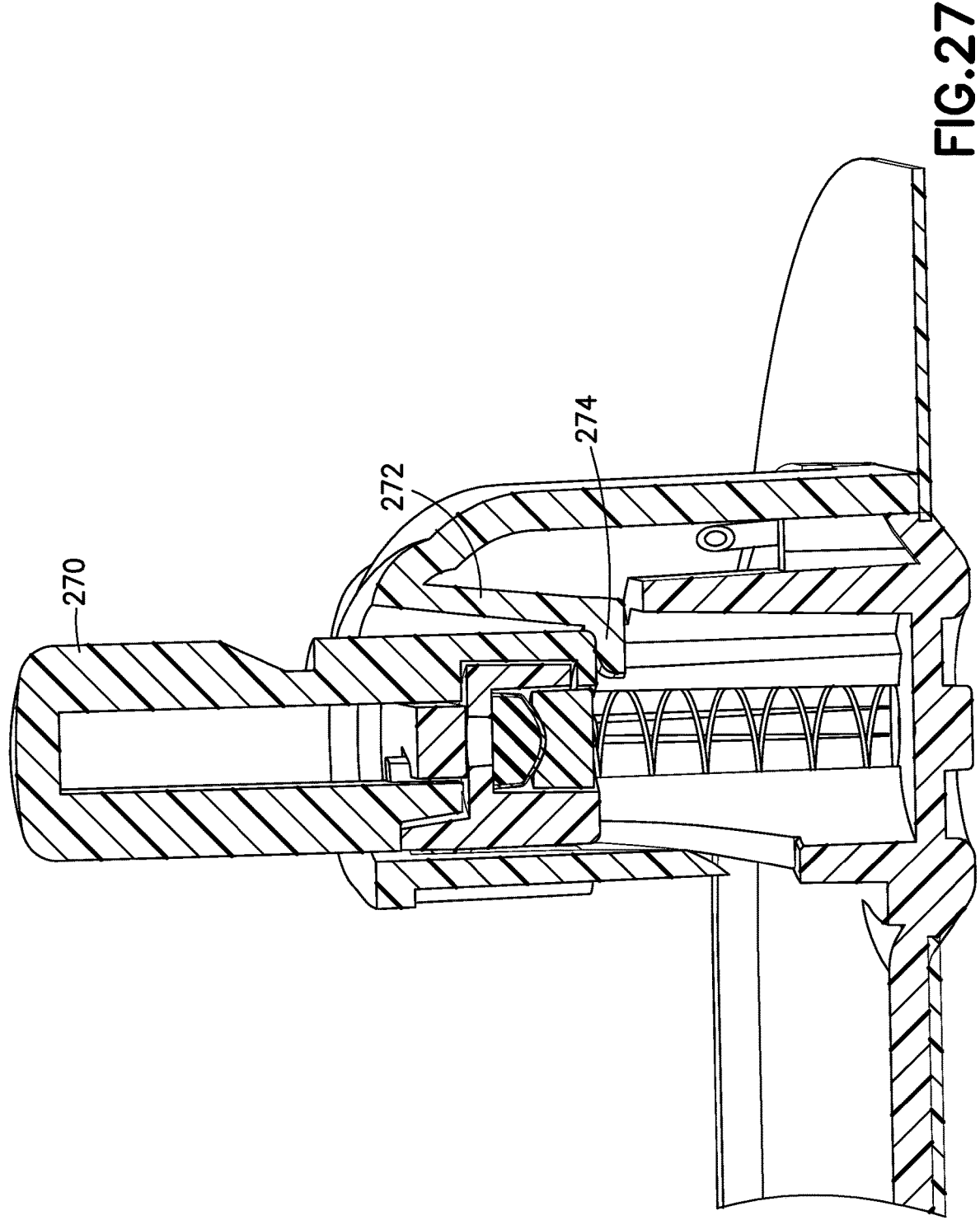
FIG. 27 is a sectional view of another embodiment of a lock arm in a pre-activation state in accordance with an embodiment of the present invention.
Figure 28:
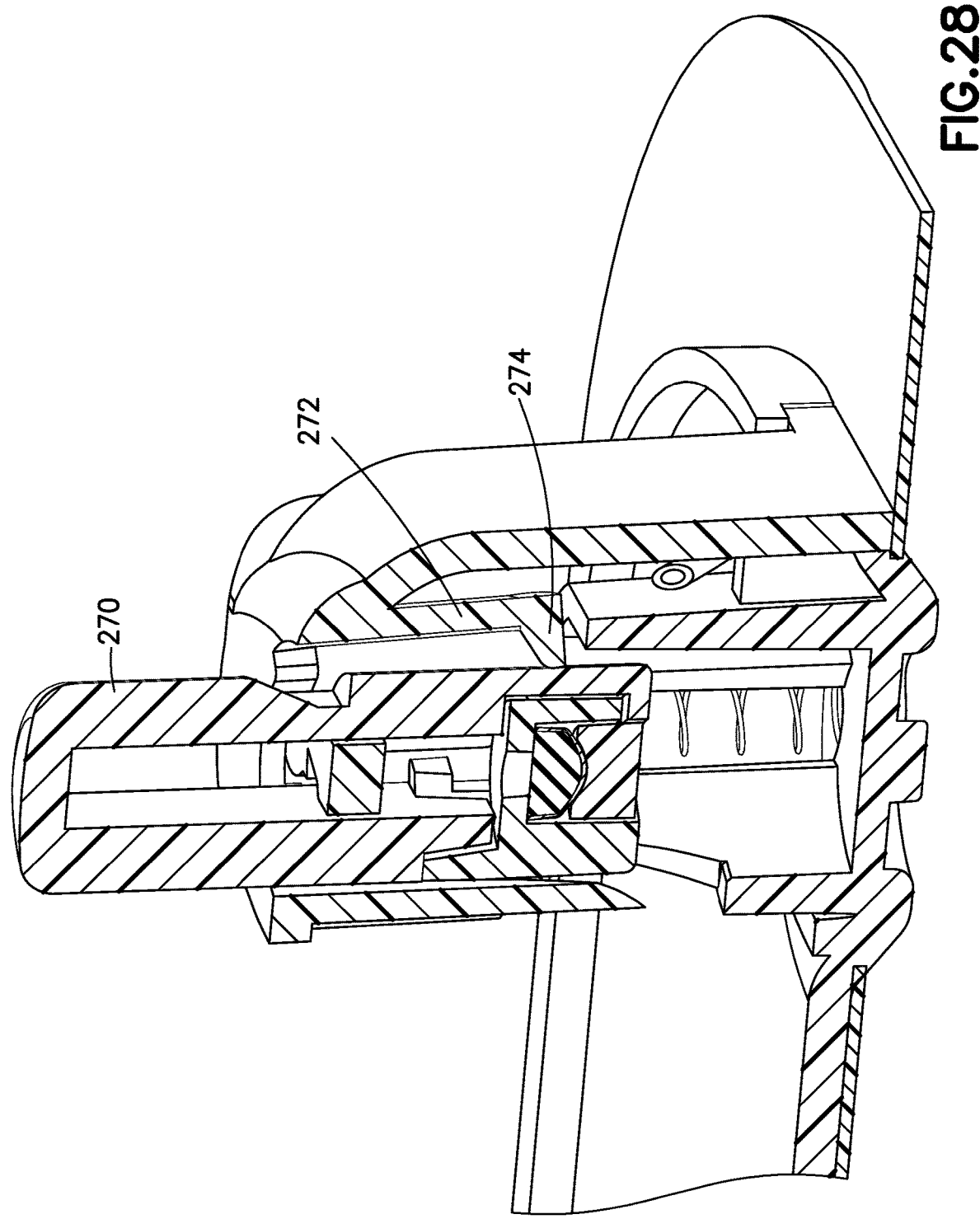
FIG. 28 is a sectional view of the lock arm of FIG. 27 in an intermediate activation state during insertion in accordance with an embodiment of the present invention shows the device.
Figure 29:
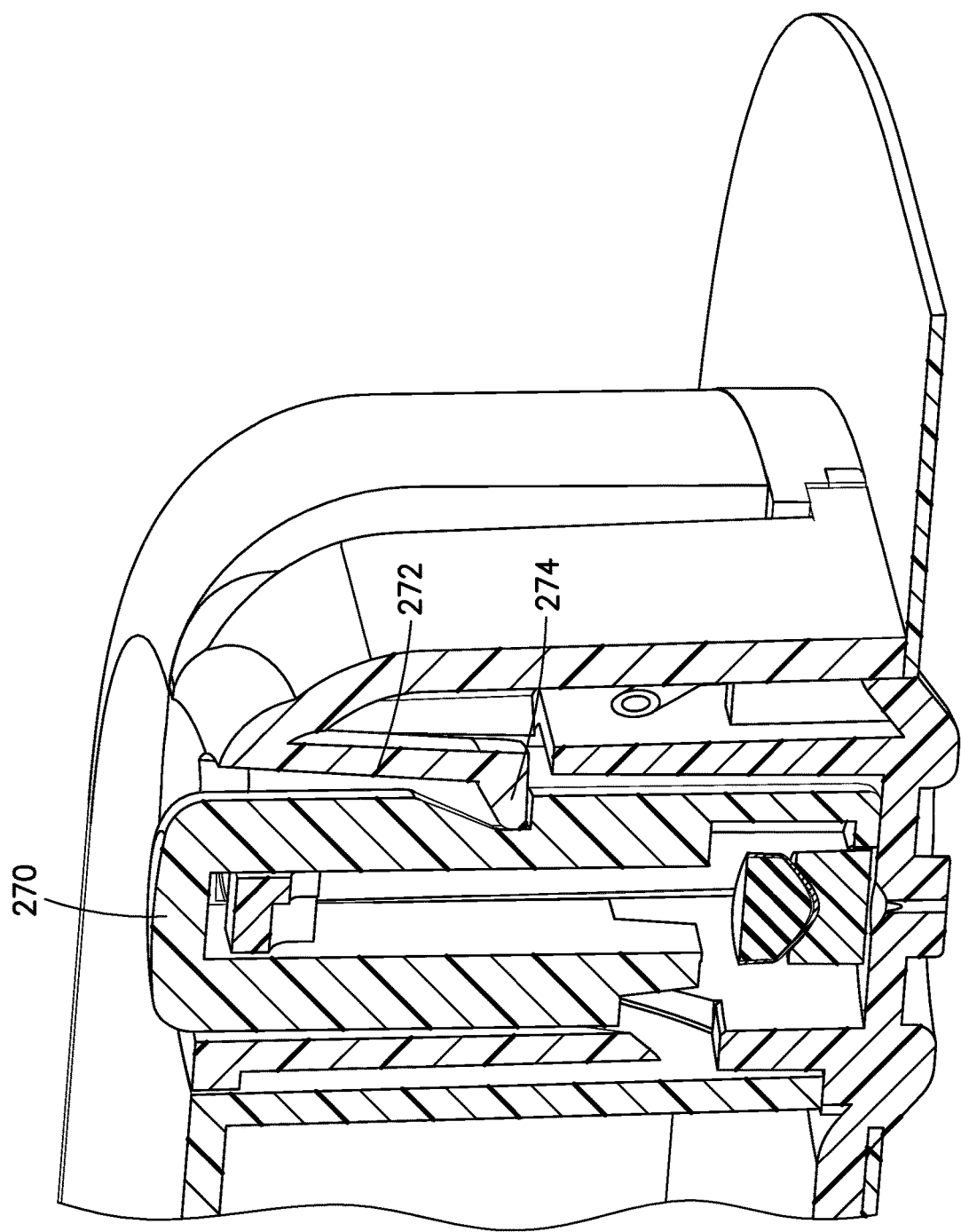
FIG. 29 is a sectional view of the lock arm of FIG. 27 in a post-activation state in accordance with an embodiment of the present invention shows the device.

In the above exemplary embodiment, the ribs 236 determine the minimum insertion force to start activation of the device which ensures full activation. Alternatively, the lock arm 112 can be configured to also determine the minimum activation force. As noted above, the lock arm 112 protrudes from the top housing and snaps into a detent in the button in the post-activation state locking the button subassembly in place keeping the catheter in the skin. FIG. 27 shows another embodiment of the lock arm 272 including a flange 274 on the lock arm that holds the button 270 in the pre-activation position. The contoured flange 274 of the lock arm 272 protrudes and captures a bottom edge of the button 270 in the pre-activation state, holding the button subassembly in place until a sufficient force is applied to the button. Once a sufficient force is applied to the button 270, the flange 274 is deflected clear of the button 270. The lock arm 272 bends out of the path of the insertion button 270 when sufficient force is applied. FIG. 28 shows the device in an intermediate state during insertion. The lock arm 272 would be bent outward instead of interfering as FIG. 28 depicts. The minimum deflection force of the lock arm 272 and flange 274 ensures that the user pushes hard enough to fully insert the catheter. The lock arm 272 and flange 274 then snap into the detent 276 in the button 270 when the button reaches the down most position which locks the button and catheter as shown in FIG. 29.

Figure 30:
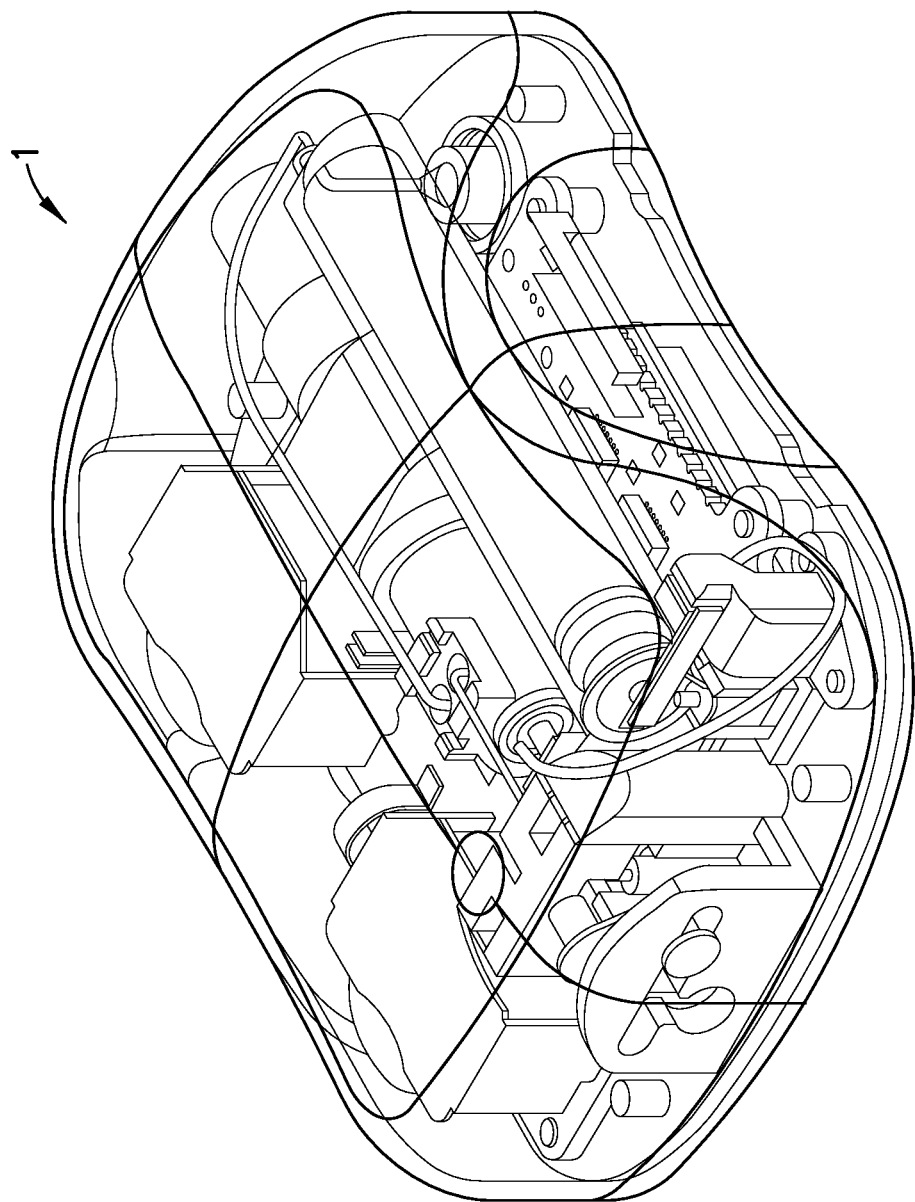
FIG. 30 is a perspective view of a patch pump incorporating a low-profile cannula insertion device, illustrated without a cover for clarity.
Figure 31:
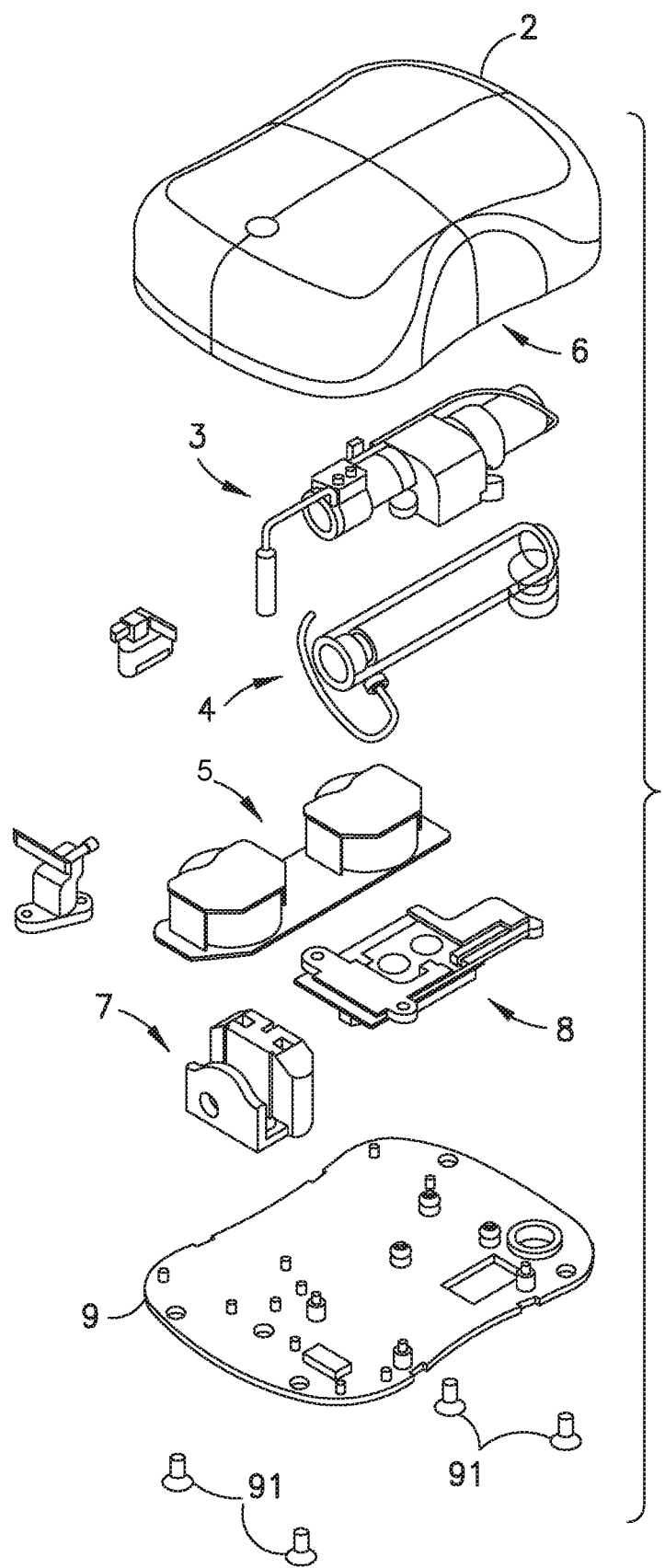
FIG. 31 is an exploded view of the various components of the patch pump of FIG. 30, illustrated with a cover.

In the above embodiments, a patch pump can be provided with one or more of the described features. FIG. 30 is a perspective view of an exemplary embodiment of a patch pump 1 according to an exemplary embodiment of the invention. The patch pump 1 is illustrated with a see-through cover for clarity and illustrates various components that are assembled to form the patch pump 1. FIG. 31 is a view of the various components of the patch pump of FIG. 30, illustrated with a solid cover 2. The various components of the patch pump 1 may include: a reservoir 4 for storing insulin; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a dose button 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

As noted above, it should be understood that inserter mechanisms come in various configurations. In some embodiments, the inserter mechanism inserts a soft catheter into the skin. In these embodiments, typically the soft catheter is supported on a rigid insertion needle. The insertion needle is inserted into the skin along with the soft catheter, and then retracted from the skin, leaving the soft catheter in the skin. In other embodiments, a soft catheter is not provided, and the insertion needle remains in the skin and forms a portion of the insulin flow path to deliver insulin until the infusion is finished. Insertion needles are typically hollow, and need to be hollow if they form part of the insulin flow path. However, insertion needles that support a soft catheter and then retract may be solid or hollow. If the insertion needle deploys a soft catheter, and retracts but remains part of the insulin flow path, then the insertion needle should be hollow. However, if the insertion needle deploys a soft catheter and then retracts but does not form part of the insulin flow path, then the insertion needle may be solid or hollow. In either case, the insertion needle is preferably rigid enough to reliably penetrate the skin, but otherwise may be made flexible enough to provide comfort to the user.

Figure 32:
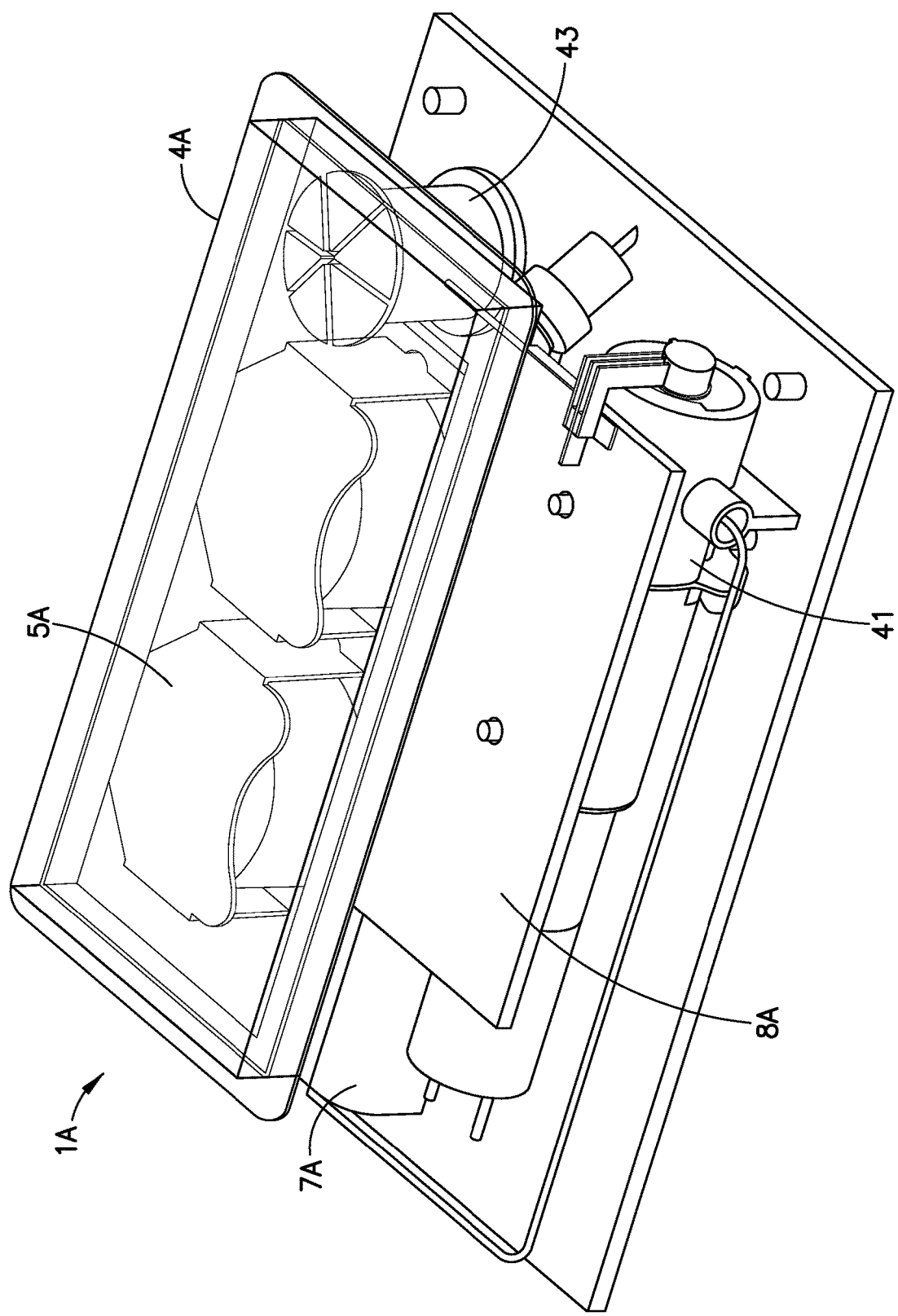
FIG. 32 is a perspective view of an alternative design for a patch pump having a flexible reservoir, illustrated without a cover.

FIG. 32 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

Figure 33:
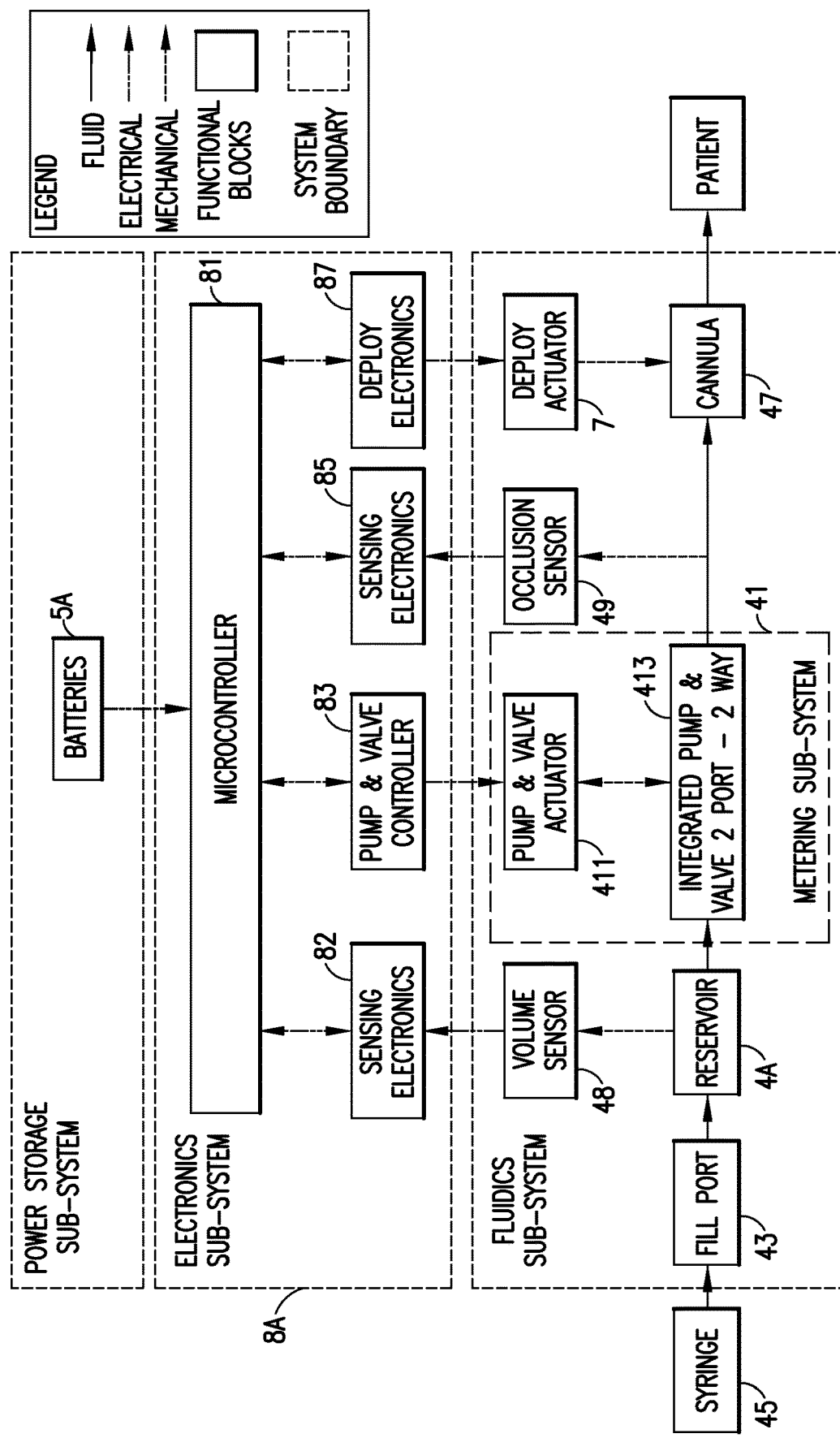
FIG. 33 is a patch-pump fluidic architecture and metering sub-system diagram of the patch pump of FIG. 32.

FIG. 33 is a patch-pump fluidic architecture and metering sub-system diagram of the patch pump 1A of FIG. 32. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87 that control the actuation of the patch pump 1A. The patch pump 1A includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor 49, a deploy actuator 7, as well as the cannula 47 for insertion into an infusion site on the user's skin. The architecture for the patch pumps of FIGS. 30 and 31 is the same or similar to that which is illustrated in FIG. 33.

Figure 51:
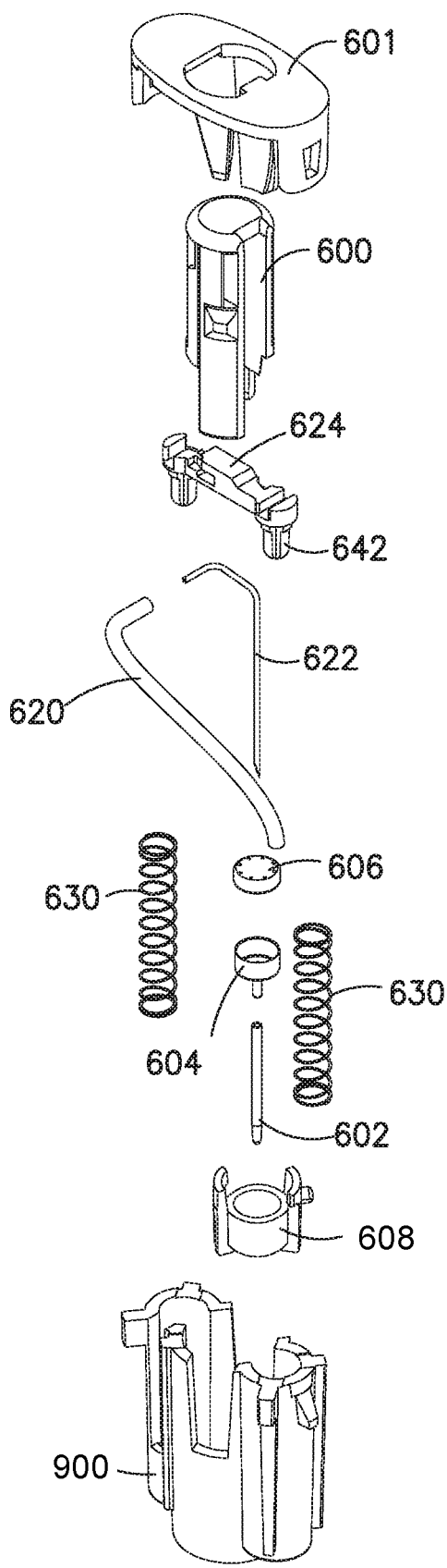
FIG. 51 is an exploded view of an insertion device in accordance with another embodiment of the present invention.

FIG. 51 illustrates another embodiment of the insertion device which is assembled by stacking together a number of subassemblies that can be contained between a top housing 601 and a mechanism housing 900. FIG. 51 is an exploded view of the insertion device. The subassemblies of FIG. 51 include a catheter/septum subassembly, an introducer needle subassembly, and a button subassembly. Other features and functions of the insertion device that are well-known to those skilled in the art are omitted from the figures and discussion for clarity.

The catheter/septum subassembly is assembled by attaching a catheter 602 on a metal wedge 604, then inserting a septum 606 in the wedge and containing it between a release collar 603 and a catheter wedge cap. The septum 606 is radially compressed by the wedge 604 and axially compressed by the release collar 603 to create a seal between the septum 606 and wedge 604.

The introducer needle subassembly is assembled by gluing or press-fitting tubing 620 on the non-patient end of the cannula or introducer needle 622, then placing the introducer needle through an introducer needle hub 624 and snapping it in place using any number of grooves, slots or detents 626 provided on a top surface of the introducer needle hub 624.

The button subassembly is built by inserting the introducer needle 622 of the introducer needle subassembly through the septum 606 and catheter 602 of the catheter/septum subassembly. The introducer needle hub 624 and catheter/septum subassembly are coupled together. This results in the introducer needle 622 and catheter 602 being moved simultaneously for insertion into a user skin surface (not shown). The button subassembly is completed by snapping the release collar 603 into the button 600 to secure the introducer needle subassembly and the catheter/septum subassembly in place. To do so, the button 600 can include detents on deflectable arms 614 to deflect and then capture therebetween the lower edge of the release collar 603.

Figure 52A:
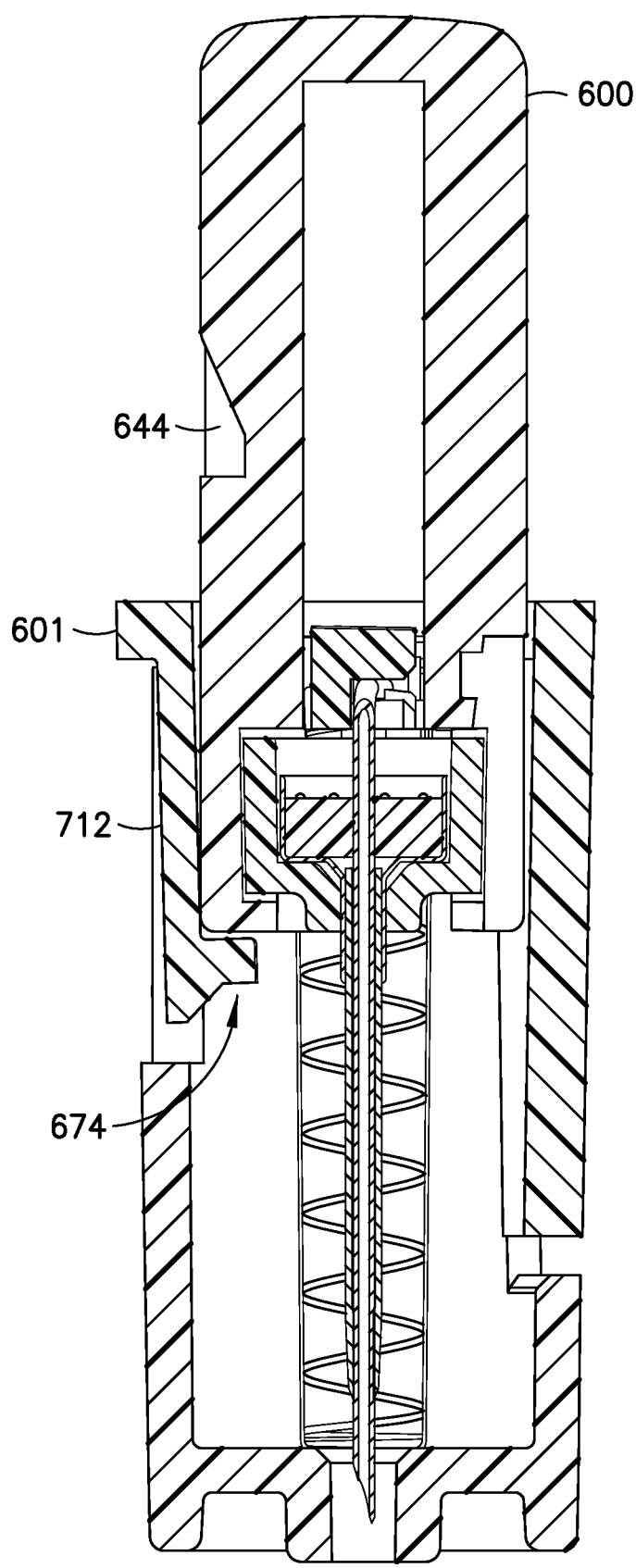
FIG. 52A-52D are cross-sectional views of the embodiment of FIG. 51 illustrating the ramp of the lock arm.
Figure 52B:
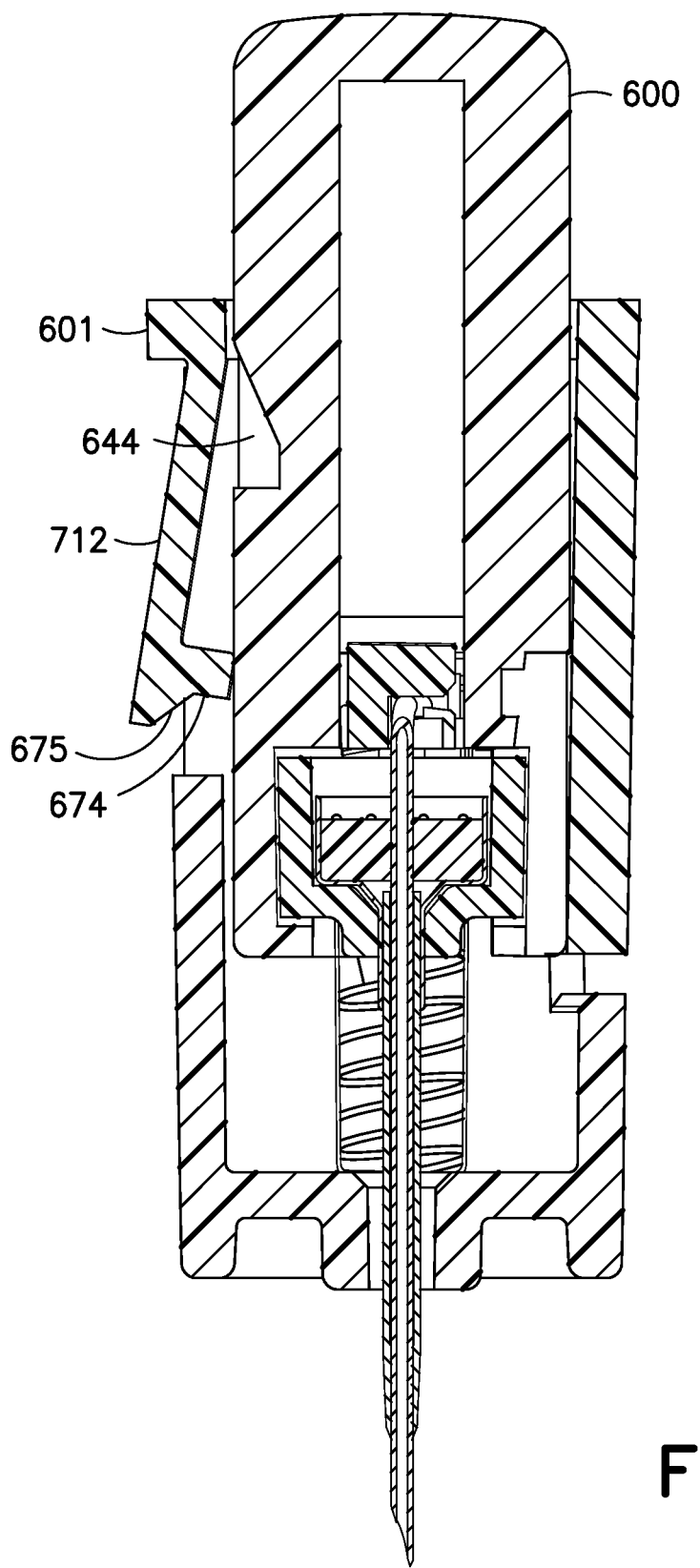
Figure 52C:
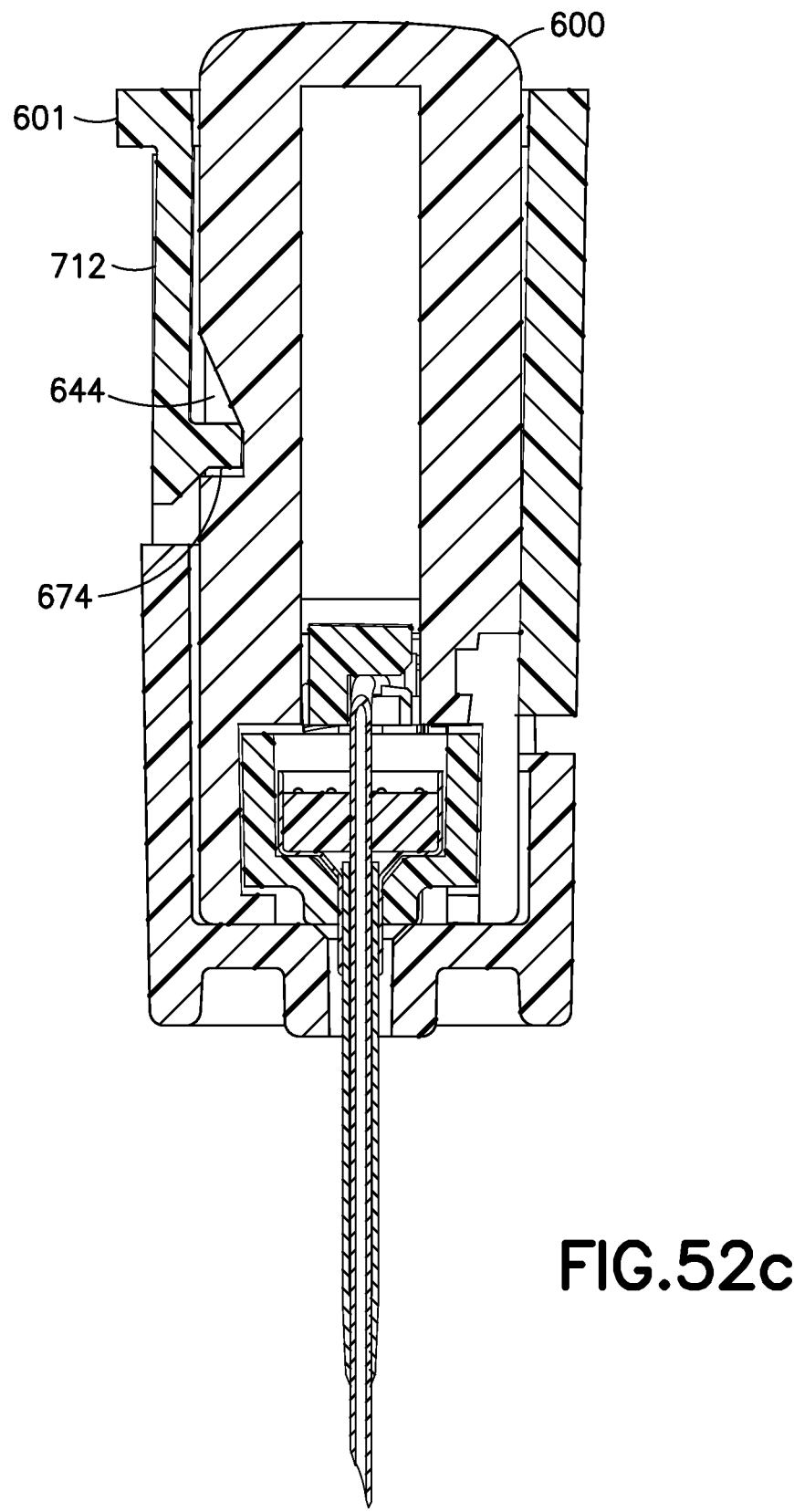
Figure 52D:
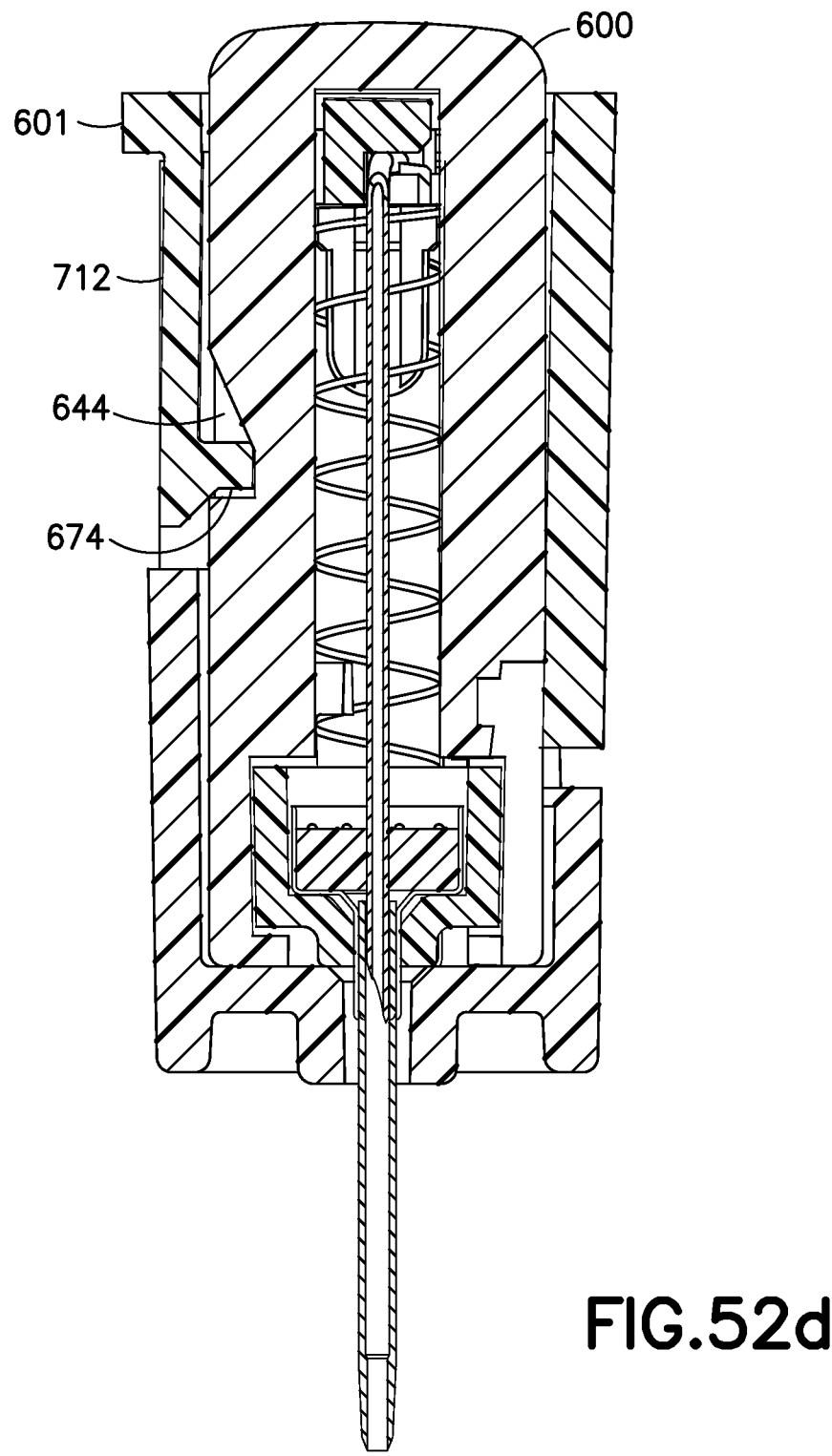

As illustrated in FIG. 51 the insertion device includes a cap 601 to secure the button subassembly within the mechanism housing 900. Cap 601 may consist of, for example, an oval shape. FIG. 52A illustrates that cap 601 has a lock arm 712 including a flange 674 on the lock arm. The flange 674 engages an edge of button 600 to thereby reduce tolerance stack and hold the button 600 in the pre-activation position. Flange 674 includes, for example, a contoured shape. The contoured flange 674 of the lock arm 712 holds the button subassembly in place in the pre-activation state until a sufficient force is applied to the button see FIG. 52A. FIG. 52B shows that once a minimum velocity of the button 600 is reached, the flange 674 deflects clear of the button 600. The lock arm 712 bends out of the path of the insertion button 600 when sufficient force is applied. FIG. 52B shows the device in an intermediate state during insertion. The lock arm 712 can be bent outward as shown in FIG. 52B and the ramp 675 takes up any clearance as button 600 is pushed downward. The minimum velocity of the lock arm 712 and flange 674 ensures that the user pushes hard enough to fully insert the catheter. As illustrated in FIG. 52C, flange 674 then snaps into the detent 644 in the button 600 when the button reaches the down most position which locks the button and catheter as shown in FIG. 52C. FIG. 52D shows the introducer needle 622 retracted into catheter 602.

Figure 53:
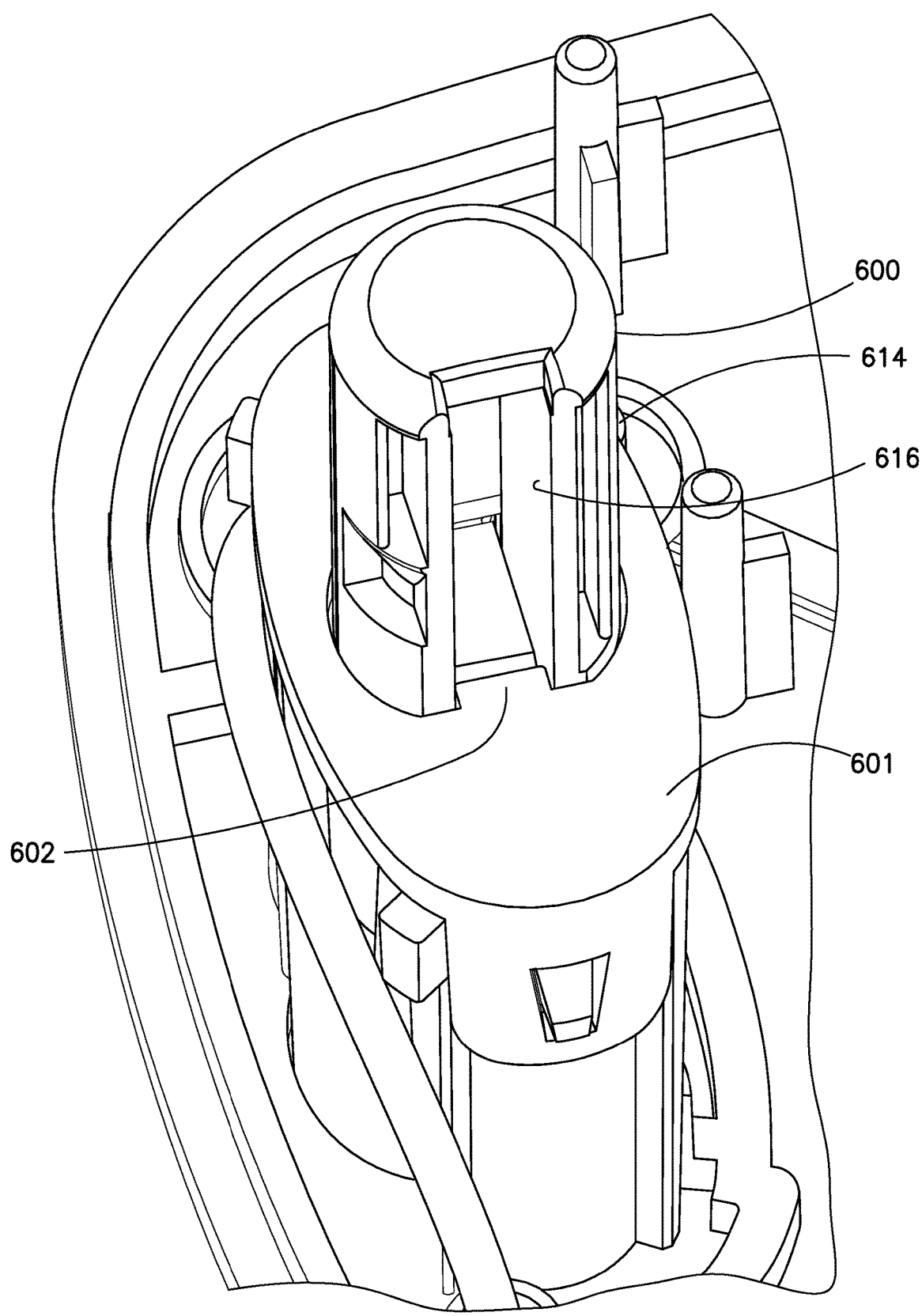
FIG. 53 is an isometric view of the embodiment of FIG. 51 showing the button slot and cap key.
Figure 54:
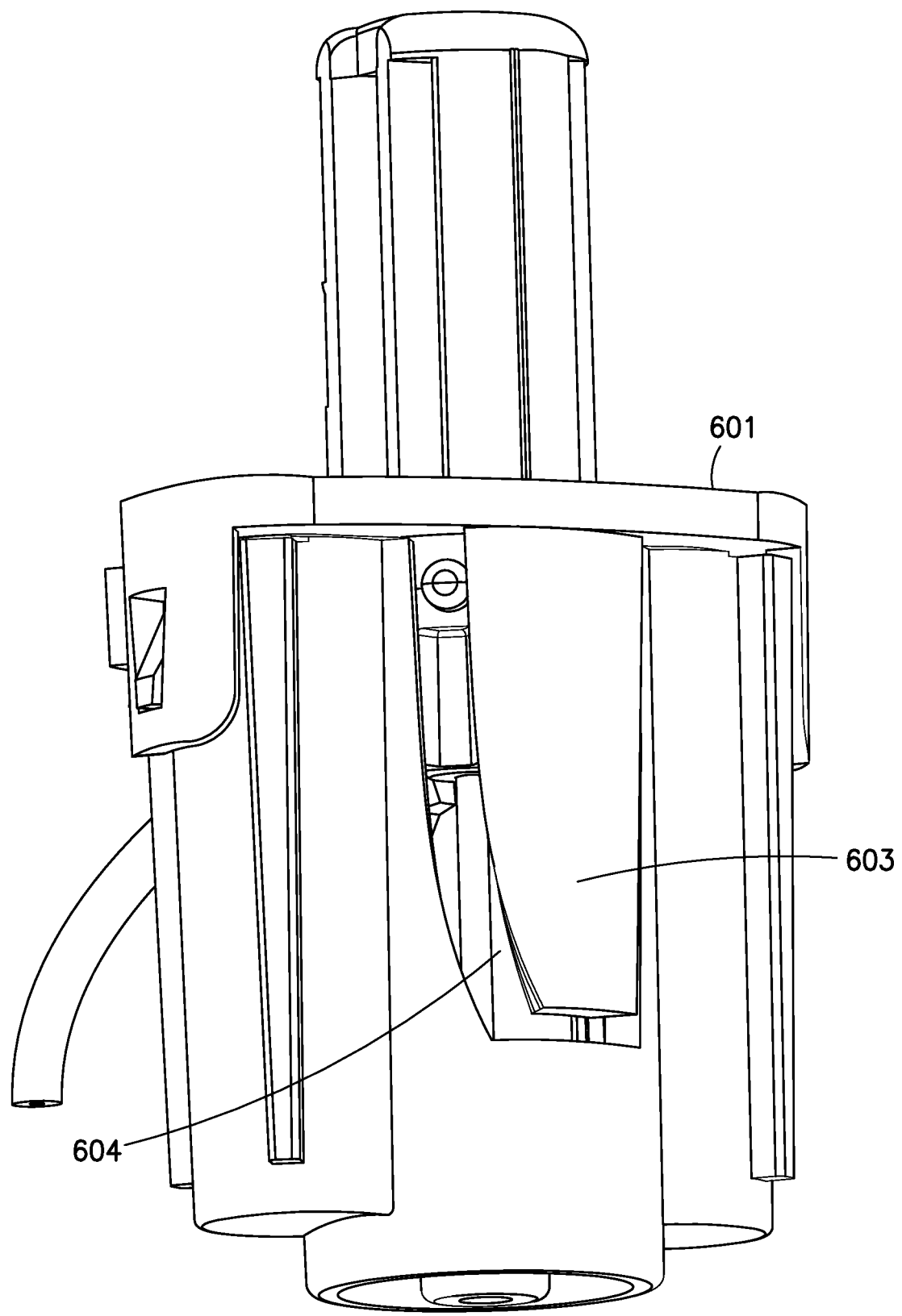
FIG. 54 is another view of the insertion device of FIG. 51 illustrating the track of the cap.

FIG. 53 illustrates that cap 601 includes a key 602. Key 602 fits into button slot 616 to prevent the button from rotating and thereby preventing premature retraction. Cap 601 also has a cap side 603 as illustrated in FIG. 54. Cap side 603 includes a track 604 extending substantially the length of mechanism housing 900 to also prevent accidental premature rotation.

Figure 55:
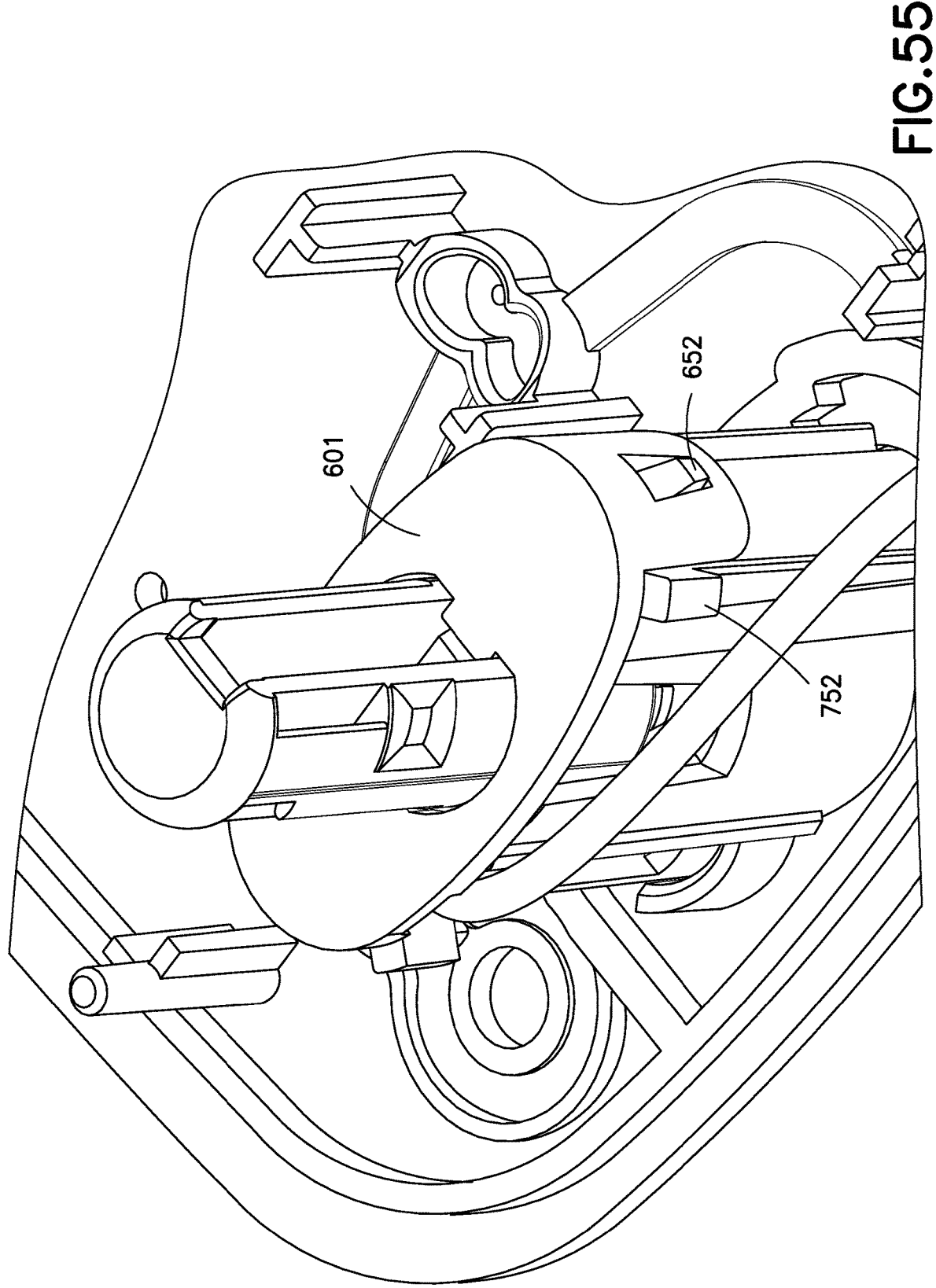
FIG. 55 is another view of the insertion device of FIG. 51 showing the protrusions for retaining the mechanism housing in the top housing.

FIG. 55 illustrates protrusions 752 on mechanism housing 900. Housing mechanism 900 is retained in the housing top 601 by an interference fit between protrusions 752 and housing top 601. Cap 601 is snapped into place and held by retaining member 652.

Figure 56:
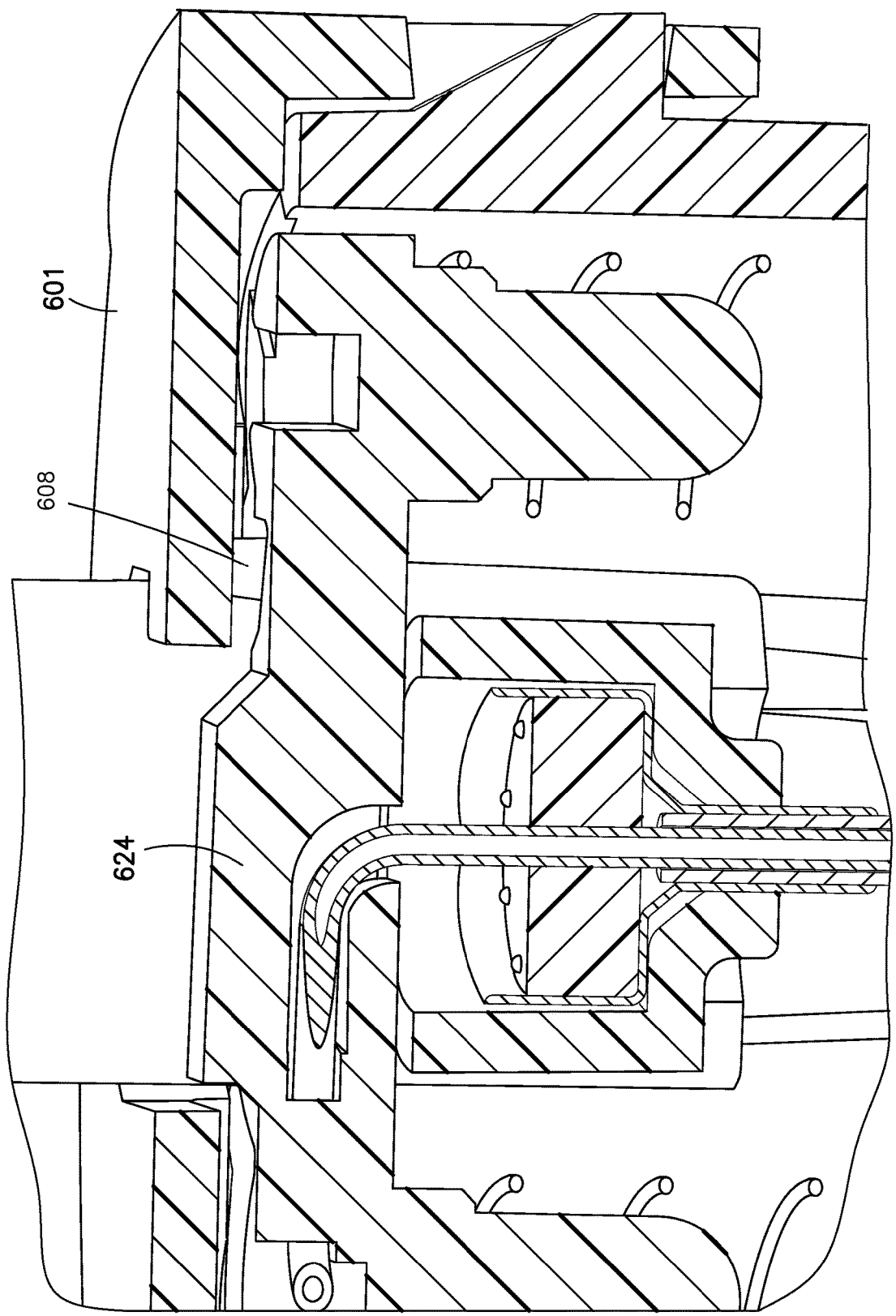
FIG. 56-57 are exploded views of the insertion device of FIG. 51 illustrating the gap between the cap and hub pre and post-activation.
Figure 57:
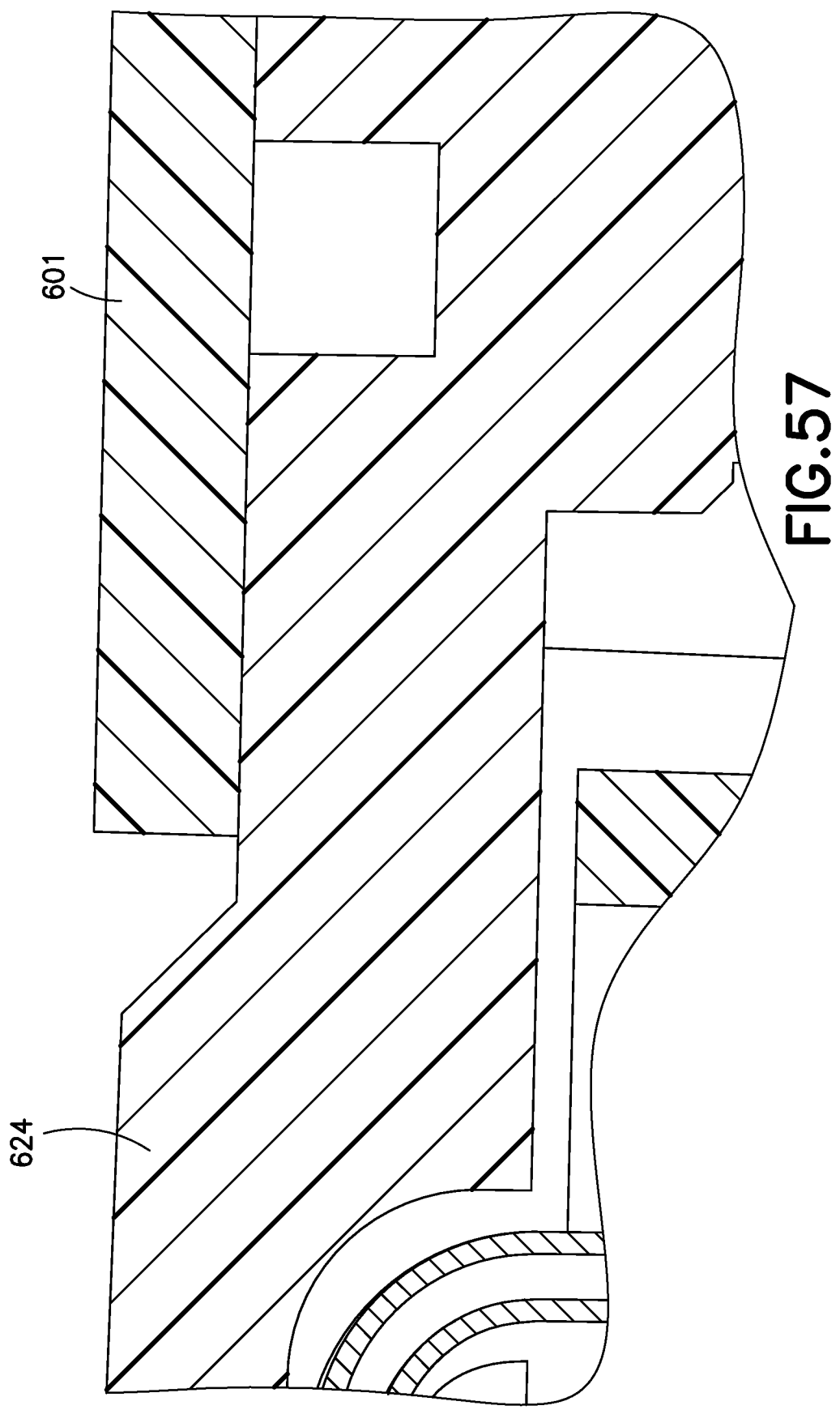
Figure 58A:
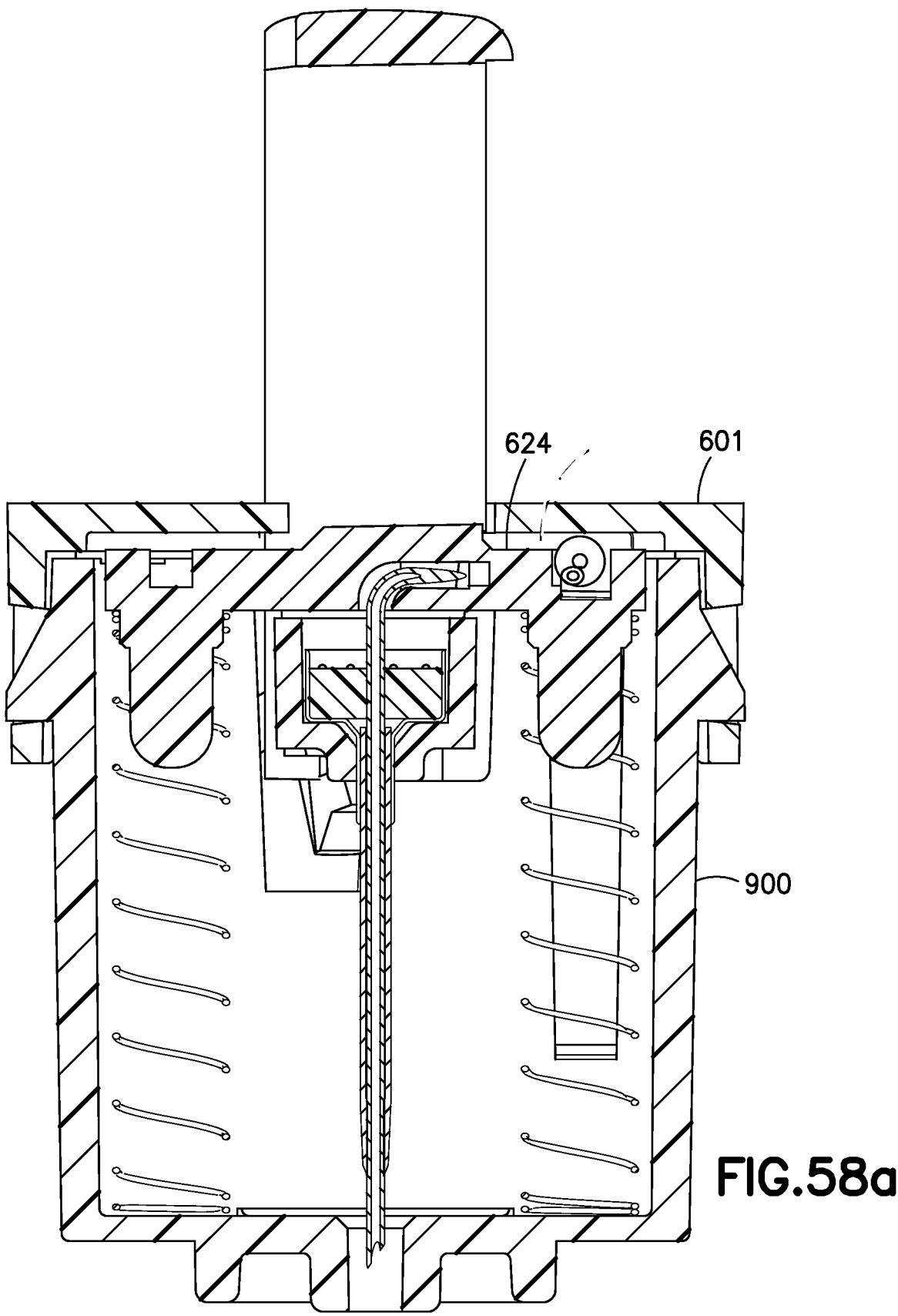
FIG. 58A is a cross-sectional view of the insertion device of FIG. 51 before activation illustrating the gap between the cap and hub.
Figure 58B:
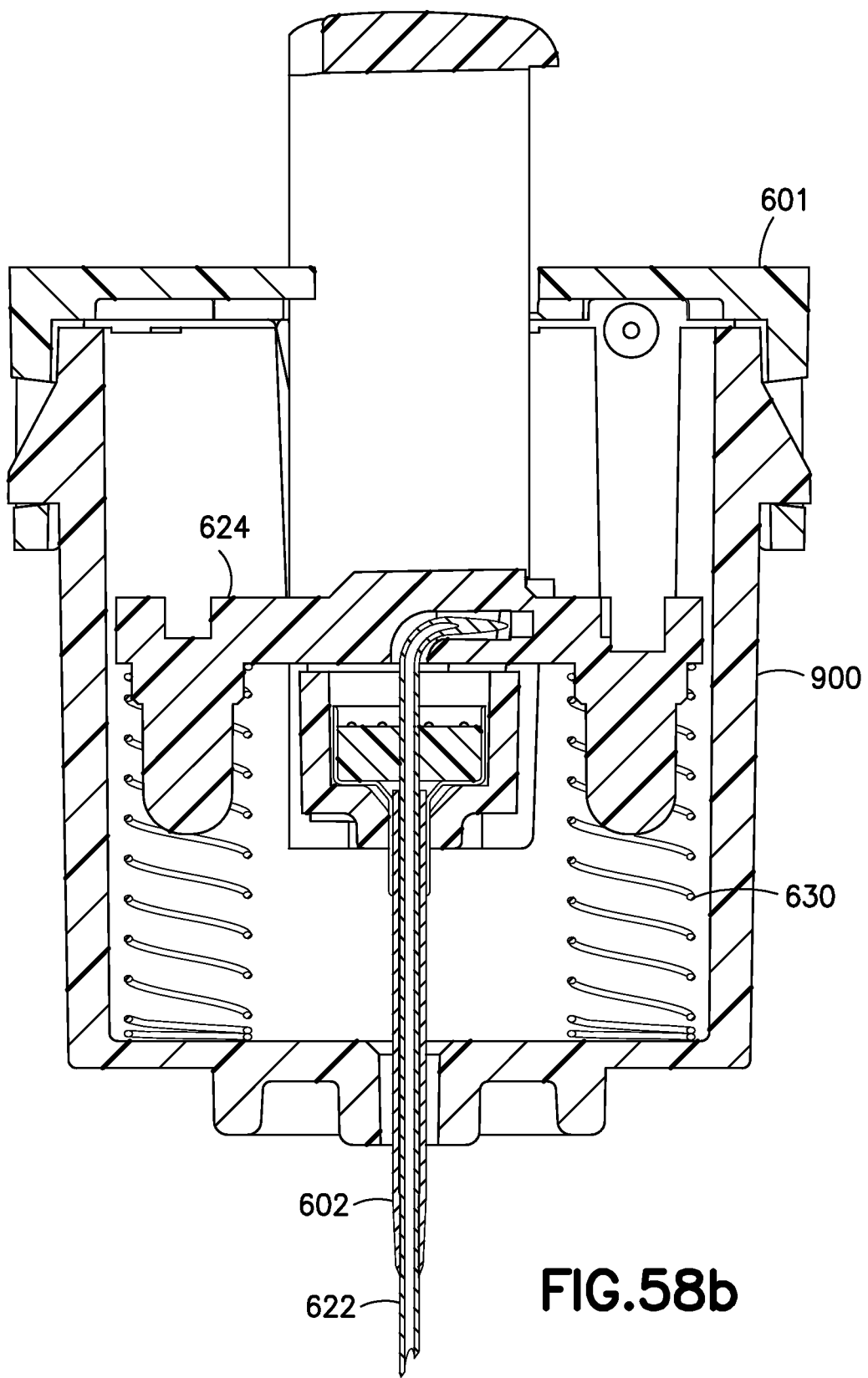
FIG. 58B is a cross-sectional view of the insertion device of FIG. 51 after activation.
Figure 58C:
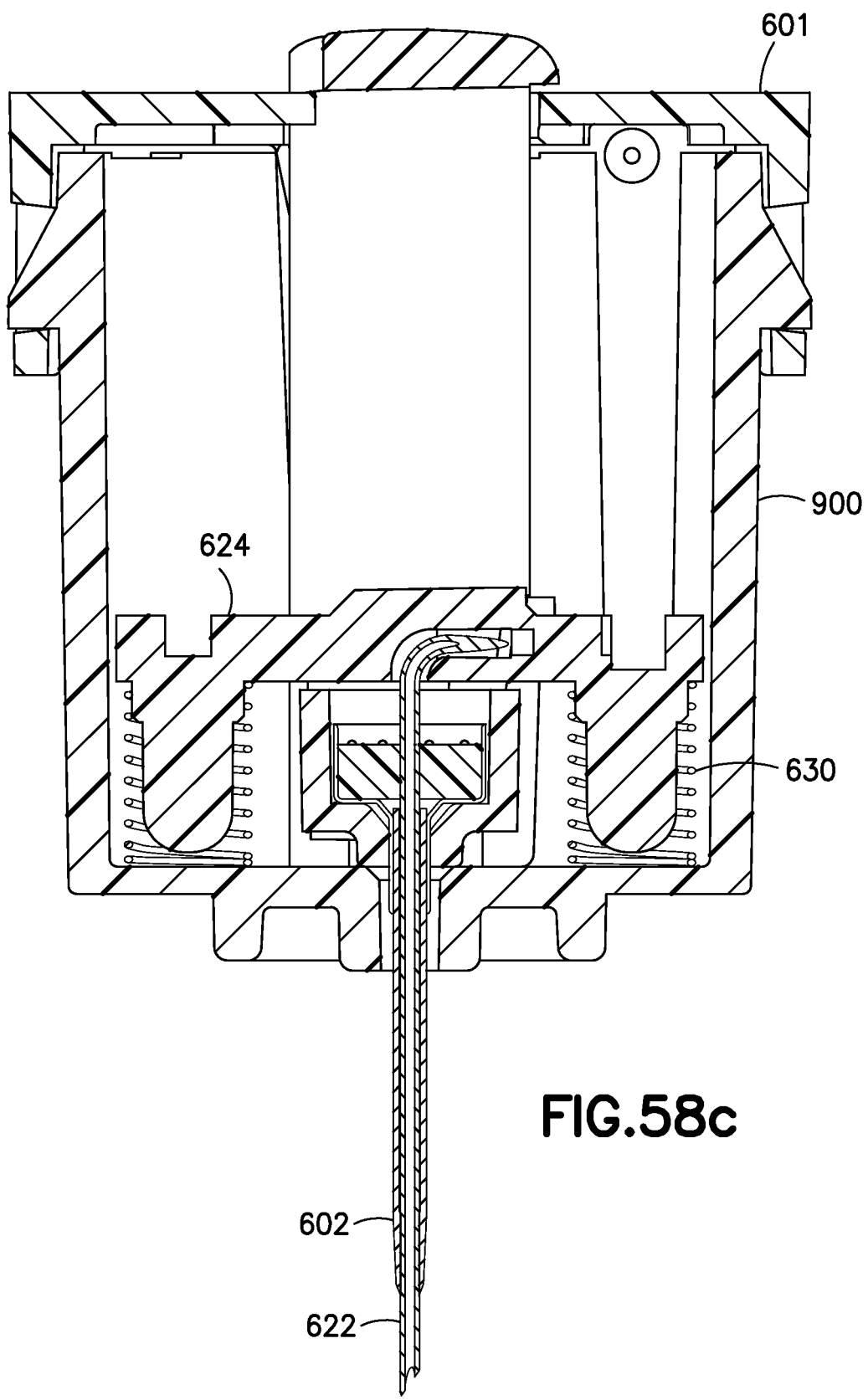
FIG. 58C is a cross-sectional view of the insertion device of FIG. 51 after completion of activation.
Figure 58D:
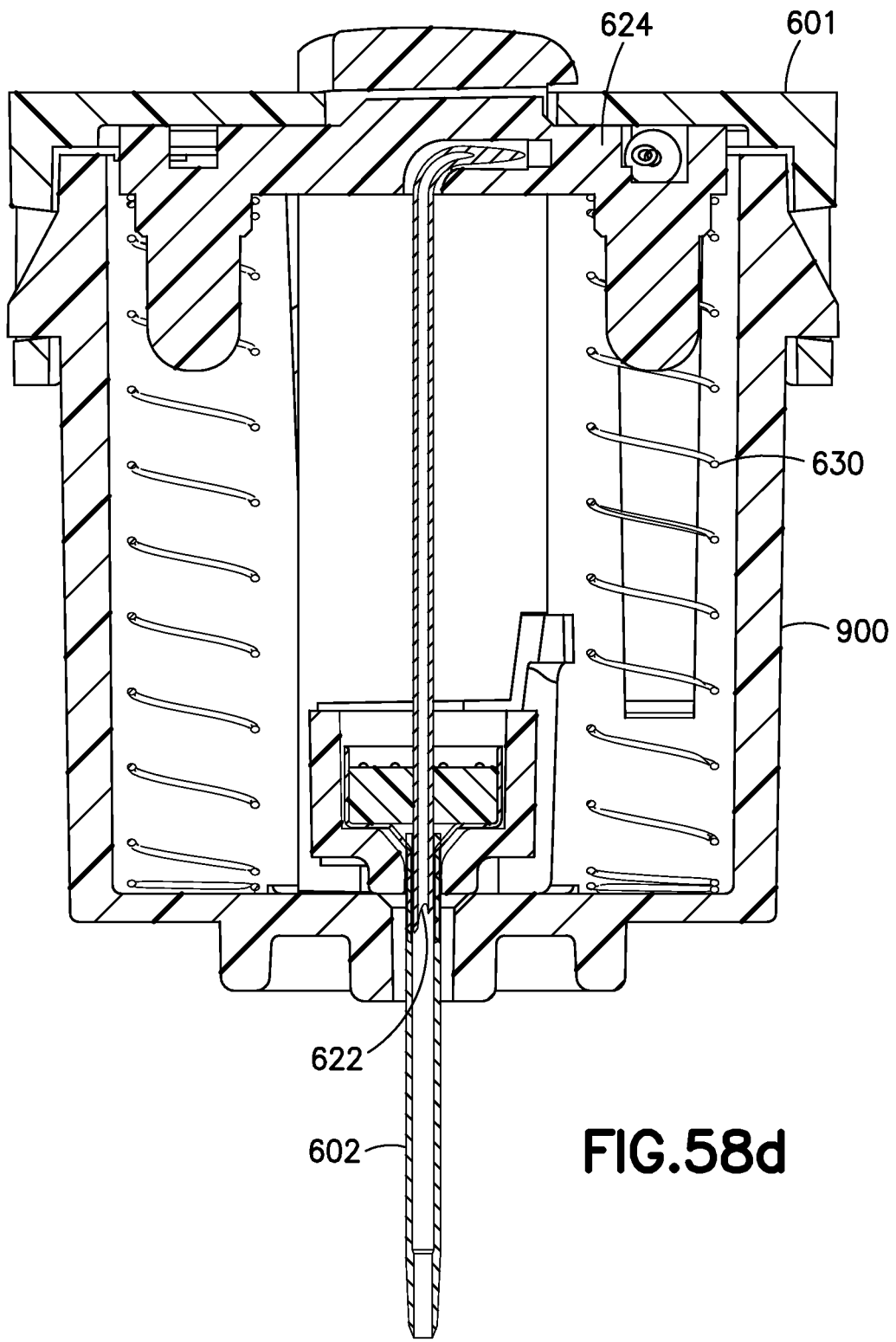
FIG. 58D is a cross-sectional view of the insertion device of FIG. 51 after retraction.

The insertion device of the present embodiment provides improved needle shielding and prevents needle stick hazard after use. As illustrated in FIGS. 56 and 57, in the pre-activation state, the springs 630 are preloaded. Also in the pre-activation state, introducer hub 624 and cap 601 abut release collar 603 forming a gap between cap 601 and introducer hub 624. FIG. 58a shows button 600 extended in the pre-activation state. When button 600 is pressed hub 624 travels downward insertion needle 622 and cannula 602 also travels downward and springs 630 are compressed illustrated in FIG. 58b. FIG. 58c shows the insertion needle 622 and cannula 602 fully extended out of the base 102. After the insertion needle 622 and cannula 602 reach the desired depth, springs 630 force the introducer needle hub 624 and introducer needle 622 upward into the retracted position, leaving the catheter/septum subassembly in the down and inserted position as shown in FIG. 58c. FIG. 58c illustrates the introducer needle 222 retracted farther into mechanism housing 900 in the retracted stated than in the activation state of FIG. 58 as where introducer needle hub 624 abuts against cap 601 eliminating the gap. Further retraction of the introducer needle as shown in FIG. 58d ensures needle stick shielding and to protects the catheter from damage.

Figure 59:
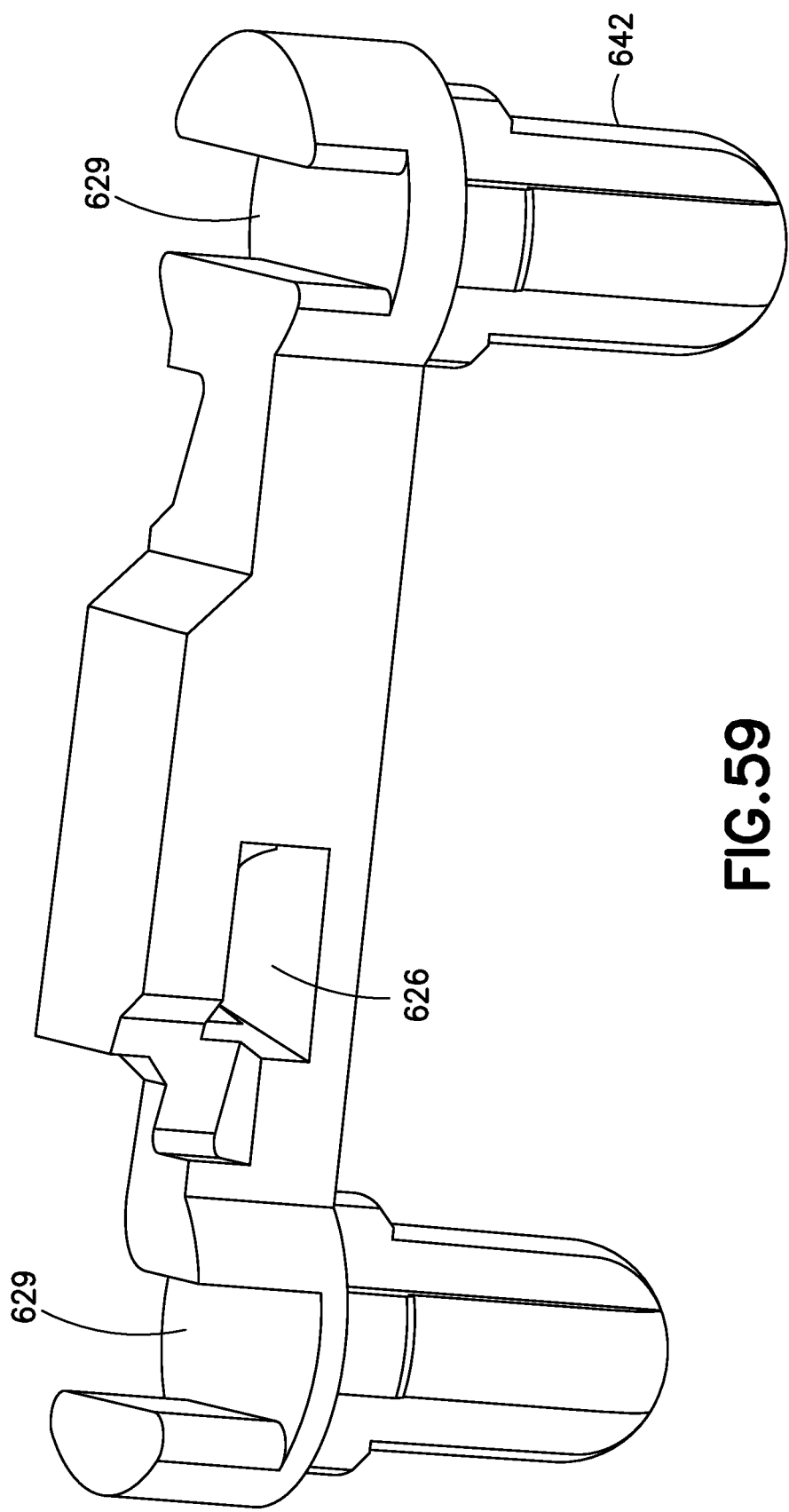
FIG. 59 is a view of the insertion device of FIG. 51 showing the hub with an extra slot.

Additional improvements of the current embodiment include bosses 642 on the introducer hub 624 having a shorter length than the length in previous embodiments. This shorter length enhances centering and alignment of the springs 630 with the introducer hub 624. The introducer hub 624 also includes an extra slot 629 as shown in FIG. 59 to enhance the efficiency of molding.

To best target the desired depth, the base can include skin interface geometry to achieve and maintain a desired insertion depth, avoid skin surface tenting, and/or tension the skin surface at the insertion site. FIG. 60 shows an alternative example of such skin interface geometry with a catheter deployed. In the perspective view of the device 802, a post 804 from which the catheter 602 extends during placement, protrudes into the skin surface (not shown) which helps prevent shallow catheter tip insertion in cases where the skin tented. The post 804 can extend from the base surface of the device 802 to any desired length, and can be rounded and/or chamfered at the distal end contacting the skin surface.

A well 808 can be provided surrounding the post 804. The well 808 provides space for skin that is displaced during insertion and helps the post 804 protrude into the skin surface. A wall 810 surrounds and defines the well 808, and can extend from the base surface of the device 802 to any desired length and can be rounded and/or chamfered at the distal end contacting the skin surface. The round opposing cylinders 812 in FIG. 60 are provided as flush with the base surface of the device 802 the adhesive that retains the base on the skin surface during use extends over the round opposing cylinders 812, which improves functionality of the device and reduces tenting.

Figure 62:
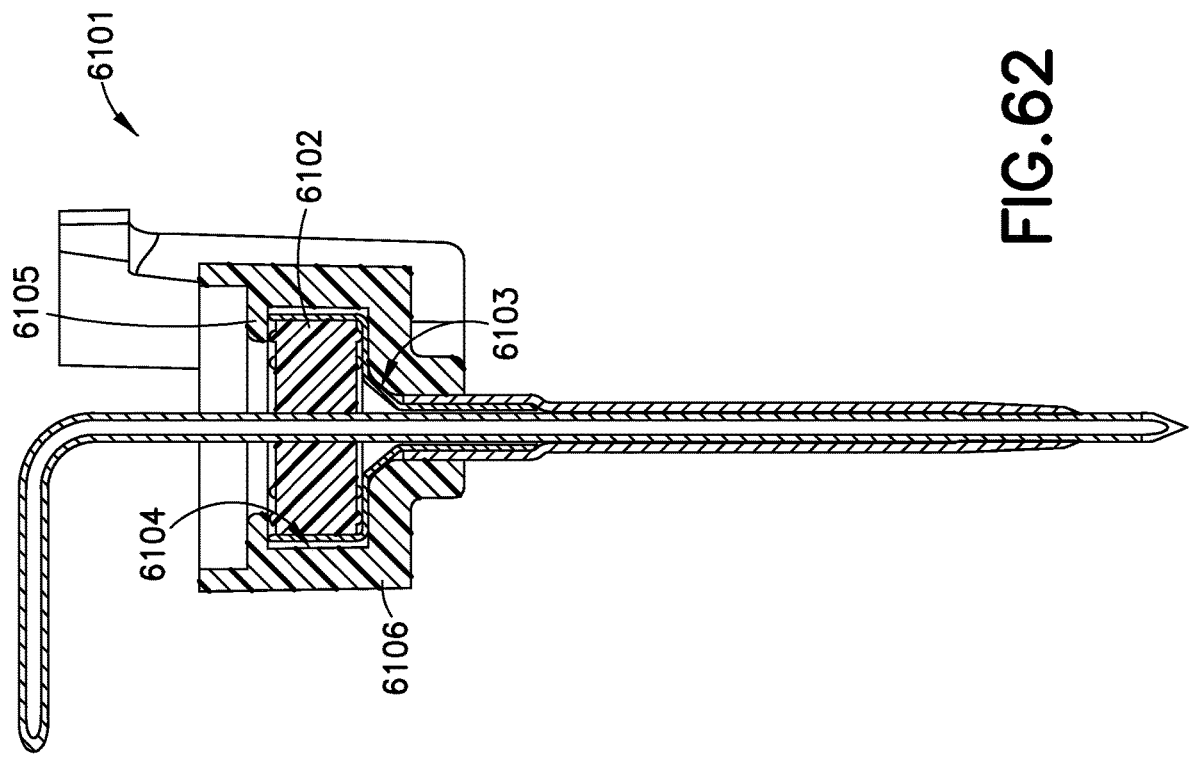
FIG. 62 is a cross-section view of the alternate catheter/septum subassembly of FIG. 61.
Figure 61:
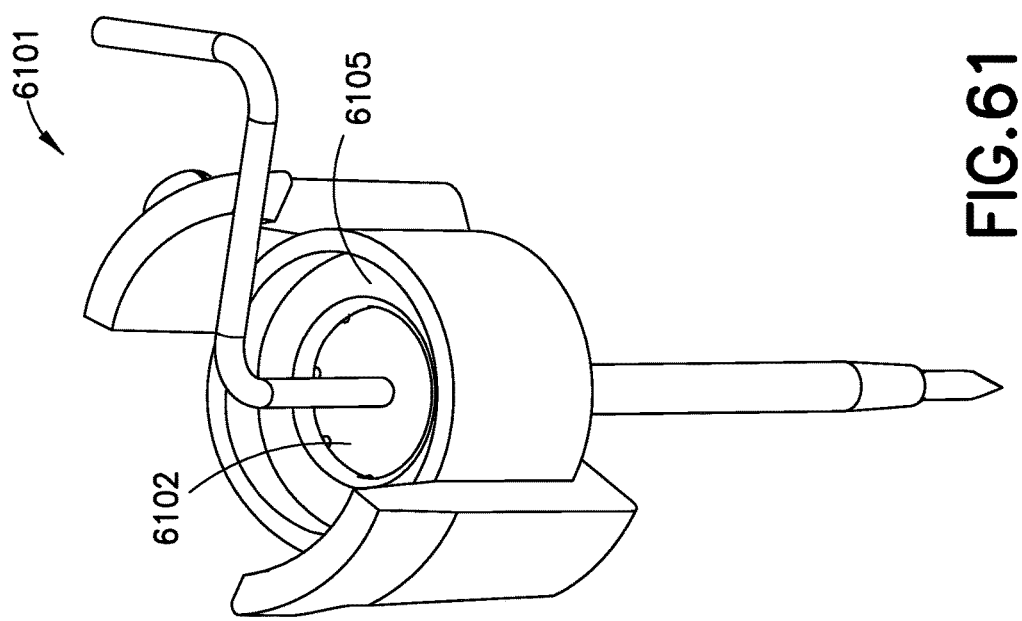
FIG. 61 is an isometric view of an alternate catheter/septum subassembly in accordance with an embodiment of the present invention.

FIGS. 61-62 illustrate an alternate release collar, septum and wedge for use in an embodiment of the present invention. Catheter/septum subassembly 6101 comprises a release collar 6106 that is deformed to retain a septum 6102 and wedge 6103. Septum 6102 is preferably cylindrical in shape. As best seen in FIG. 62, release collar 6106 is heat staked during manufacture to deform the inner surface 6104 of the release collar 6106 to form a lip 6105 that retains the septum 6102 and wedge 6103 within the release collar 6106. This simplifies manufacturing and reduces the number of components required. Heat staking is described in further detail, for example, in U.S. Pat. No. 5,135,489, the entire contents of which are hereby incorporated by reference. It should be appreciated that any suitable septum and wedge retention method may be used with the insertion mechanisms described herein, and the septum and wedge retention structure shown in FIGS. 61-62 is merely exemplary of one such suitable structure. Any other structures of septum, wedge, and related components described herein, or suitable variations thereof are within the scope of the present invention.

Figure 63:
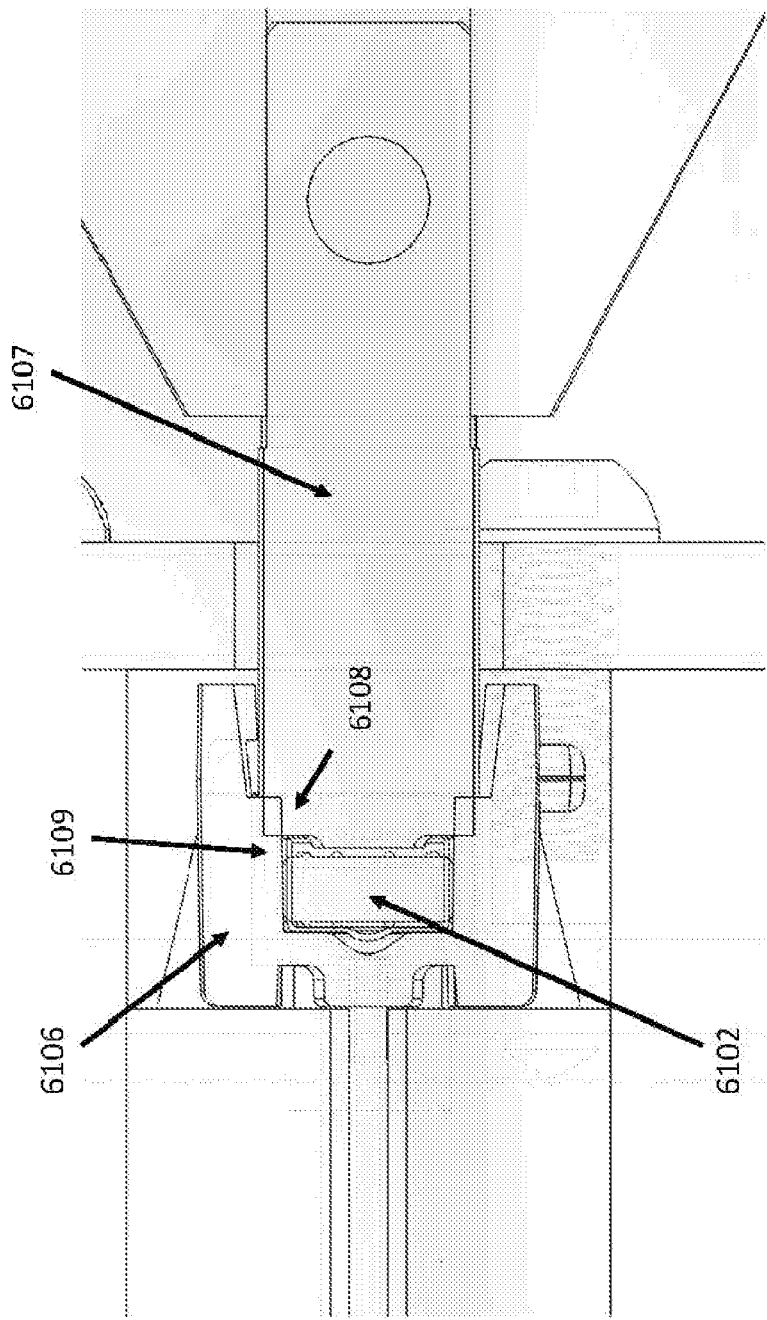
FIG. 63 is a cross-section view of a heat staking tool in accordance with an exemplary embodiment of the invention.

FIG. 63 is a cross sectional view of a staking tool for heat staking the release collar shown in FIGS. 61-62 above. As illustrated, a staking tool 6107 includes a staking geometry 6108 to deform a portion 6109 of the inner surface 6104 of the release collar 6106. The deformation forms the lip 6105 shown in FIGS. 61-62.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and their equivalents.

The invention claimed is:

1. A catheter insertion device, comprising:
   a device housing and a button slidably captured therein;
   a catheter/septum subassembly, rotatably captured by said button; and
   an introducer needle subassembly, releasably secured to said catheter/septum subassembly, wherein said catheter/septum subassembly rotates relative to said button from a first radial position secured to said introducer needle subassembly, to a second radial position released from said introducer needle subassembly, in response to and during a linear movement of said button and an interaction of a portion of the catheter/septum subassembly with a helical pathway, and wherein said button moves said introducer needle subassembly from a first linear position to a second linear position to insert a catheter of said catheter/septum subassembly, and simultaneously rotates said catheter/septum subassembly to said second radial position, thereby releasing said introducer needle subassembly from said catheter/septum subassembly;
   wherein said device housing comprises: a top housing, comprising a first contoured surface; and a mechanism housing, comprising a second contoured surface, wherein said first and second contoured surface comprise the helical pathway.

2. The catheter insertion device of claim 1, further comprising: a spring disposed between said device housing and said introducer needle subassembly, wherein said spring urges said introducer needle subassembly from said second linear position to a third linear position past said first linear position.

3. The catheter insertion device of claim 2, further comprising: a cylindrical opening, wherein said spring is disposed in said cylindrical opening; and a boss disposed on said introducer needle subassembly, wherein said boss is disposed in said cylindrical opening.

4. The catheter insertion device of claim 1, further comprising: a plurality of springs disposed between said device housing and said introducer needle subassembly, wherein said springs urge said introducer needle subassembly from said second linear position to a third linear position past said first linear position.

5. The catheter insertion device of claim 4, further comprising: a plurality of cylindrical openings, wherein each of said springs of said plurality are disposed in a respective cylindrical opening; and a plurality of bosses disposed on said introducer needle subassembly, wherein each of said bosses of said plurality are disposed in a respective cylindrical opening.

6. The catheter insertion device of claim 1, wherein said catheter/septum subassembly comprises: a pin or other structure, slidably captured in said helical pathway, wherein said linear movement of said button is converted into said rotational movement of said catheter/septum subassembly by movement of said pin in said helical pathway.

7. The catheter insertion device of claim 1, wherein said introducer needle subassembly comprises: a hollow cannula, wherein an end of said cannula remains in fluid communication with said catheter to comprise an uninterrupted fluid path.

8. The catheter insertion device of claim 1, further comprising: a rib disposed on said button to engage said housing, wherein said rib is configured to secure said button in said first linear position until an activation force applied to said button exceeds a threshold.

9. The catheter insertion device of claim 1, further comprising: an arm disposed on said housing to engage said button, wherein said arm is configured to secure said button in said second linear position after an activation force has been applied to said button.

10. The catheter insertion device of claim 9, further comprising: said arm disposed on said housing to engage said button, wherein said arm is configured to secure said button in said first linear position until an activation force applied to said button exceeds a threshold.

11. The catheter insertion device of claim 1, wherein said introducer needle subassembly comprises: an introducer needle including a proximal end and a distal end adapted to be inserted into a patient; and an introducer hub including a first end and a second end with a receiving member therebetween, wherein the introducer needle is configured for insertion into the receiving member.

12. The catheter insertion device of claim 11, wherein the introducer needle comprises: a bend portion between the proximal end and the distal end; and an arm portion between the bend portion and the proximal end; the introducer hub includes a retaining member on an upper surface thereof; and the receiving member comprises a receiving slot, wherein the bend portion is adapted to be inserted into the receiving slot and the arm portion is adapted to be secured in the retaining member by a translational motion.

13. The catheter insertion device of claim 12, wherein the translational motion does not require rotation.

14. The catheter insertion device of claim 11, wherein the receiving member comprises a hole and the distal end of the introducer needle is received in the hole and extends a predetermined length from the introducer hub.

15. The catheter insertion device of claim 14, wherein the introducer hub includes a retaining member on an upper surface thereof; and the proximal end of the introducer needle is bent over the upper surface of the introducer hub and secured by the retaining member.

16. The catheter insertion device of claim 14, wherein said receiving member comprises a snap.

17. The catheter insertion device of claim 14, wherein the introducer needle is insert molded with the introducer hub.

18. The catheter insertion device of claim 14, wherein the introducer hub includes: a retaining member on an upper surface thereof the first end; a well on the upper surface between the retaining member and the second end; and a rounded feature within the well and next to the receiving member, wherein the receiving member comprises a hole.

19. The catheter insertion device of claim 18, wherein the proximal end of the introducer needle is bent over the rounded feature of the introducer hub and secured by the retaining member.

20. The catheter insertion device of claim 19, wherein the retaining member is a snap.

21. The catheter insertion device of claim 19, wherein the well includes glue to secure the introducer needle to the introducer hub and prevent the introducer needle from moving relative thereto.

22. The catheter insertion device of claim 18, wherein a radius of the rounded feature is sized such that crimping or reducing an inner diameter of the needle is prevented ensuring that fluid will flow through a bend portion in the needle.

23. The catheter insertion device of claim 1, wherein the device housing includes a skin contacting surface.

24. The catheter insertion device of claim 23, wherein a post extends from the skin contacting surface and a wall surrounds the post forming a well between the wall and the post.

25. The catheter insertion device of claim 24, wherein the wall extends from the skin contacting surface a desired length and the wall and post are both chamfered at a distal end thereof.

26. The catheter insertion device of claim 1, wherein said catheter/septum subassembly comprises a release collar formed with a lip on an inner surface of the release collar to retain a septum and a wedge within the release collar.

27. The catheter insertion device of claim 26, wherein said lip is formed by heat staking said inner surface of said release collar.

28. A catheter insertion device, comprising:
a device housing and a button slidably captured therein;
a catheter/septum subassembly, rotatably captured by said button; and
an introducer needle subassembly, releasably secured to said catheter/septum subassembly, wherein said catheter/septum subassembly rotates relative to said button from a first radial position secured to said introducer needle subassembly, to a second radial position released from said introducer needle subassembly, in response to and during a linear movement of said button and an interaction of a portion of the catheter/septum subassembly with a helical pathway, and wherein said button moves said introducer needle subassembly from a first linear position to a second linear position to insert a catheter of said catheter/septum subassembly, and simultaneously rotates said catheter/septum subassembly to said second radial position, thereby releasing said introducer needle subassembly from said catheter/septum subassembly,
wherein said device housing comprises a first contoured surface, wherein said first contoured surface is configured to comprise a portion of the helical pathway when adjacent to a second contoured surface.

29. The catheter insertion device of claim 28, wherein said catheter/septum subassembly comprises: a pin or other structure, slidably captured in said helical pathway, wherein said linear movement of said button is converted into said rotational movement of said catheter/septum subassembly by movement of said pin in said helical pathway.

30. A catheter insertion device, comprising:
a device housing and a button slidably captured therein;
a catheter/septum subassembly, rotatably captured by said button; and
an introducer needle subassembly, releasably secured to said catheter/septum subassembly at an initial position, wherein said catheter/septum subassembly is rotatable relative to said button from a first radial position secured to said introducer needle subassembly, to a second radial position released from said introducer needle subassembly, in response to and during a linear movement of said button from a first linear position to a second linear position and interaction of a portion of the catheter/septum subassembly with a helical pathway, to insert a catheter of said catheter/septum subassembly, and a spring disposed between said device housing and said introducer needle subassembly, wherein said spring urges said released introducer needle subassembly to a retracted position equal to or exceeding said initial position after the subassembly is released from the button at the second linear position;
wherein said device housing comprises: a top housing, comprising a first contoured surface; a mechanism housing, comprising a second contoured surface, wherein said first and second contoured surface comprise the helical pathway; and a pin or other structure, slidably captured in said helical pathway, wherein said linear movement of said button is converted into said rotational movement of said catheter/septum subassembly by movement of said pin in said helical pathway.

* * * * *